(12) United States Patent
Regan et al.

(10) Patent No.: US 8,461,389 B2
(45) Date of Patent: Jun. 11, 2013

(54) PSYCHO-PHARMACEUTICALS

(75) Inventors: Ciaran Regan, Dublin (IE); Lisa Conboy, Dublin (IE); Shane Gannon, Galway (IE)

(73) Assignee: University College Dublin, National University of Ireland, Dublin, Dublin (IE)

( * ) Notice: Subject to any disclaimer, the term of this patent is extended or adjusted under 35 U.S.C. 154(b) by 202 days.

(21) Appl. No.: 12/937,826

(22) PCT Filed: Apr. 20, 2009

(86) PCT No.: PCT/IE2009/000020
§ 371 (c)(1),
(2), (4) Date: Oct. 14, 2010

(87) PCT Pub. No.: WO2009/128057
PCT Pub. Date: Oct. 22, 2009

(65) Prior Publication Data
US 2011/0034562 A1    Feb. 10, 2011

(30) Foreign Application Priority Data
Apr. 18, 2008  (IE) .................................. S2008/0297

(51) Int. Cl.
*C07C 211/26* (2006.01)
*A61K 31/10* (2006.01)

(52) U.S. Cl.
USPC ......................................... 564/317; 514/648

(58) Field of Classification Search
None
See application file for complete search history.

(56) References Cited

FOREIGN PATENT DOCUMENTS

| EP | 0 711 763 | 5/1996 |
|----|-----------|--------|
| WO | 00/02551 | 1/2000 |

OTHER PUBLICATIONS

Database CAPLUS on STN, Acc. No. 2004:1006803, Mercier-Guyon et al., Current Medical Research and Opinion (2004), 20 (9), p. 1347-1355 (abstract).*

Protiva et al., "Basic Benzhydryl Sulfides," Chemical Abstracts, vol. 61, No. 322201, pp. 1-2, XP-002536369(1964).
Kopf et al., "Pharmacology and Toxicology of Captodiamine (p-butylmercaptobenzhydryl 1-[beta]-dimethylaminoethyl sulphide)," Arzneiimittel-Forschung, vol. 8, No. 3, pp. 154-159, XP009119818 (1958).
Takebayashi et al., "A Perspective on the New Mechanism of Antidepressants: Neuritogenesis Through Sigma-1 Receptors," Pharmacopsychiatry, vol. 37, Suppl. 3, pp. S208-S213, XP009119764 (2004).
Takebayashi et al., "Nerve Growth Factor-Induced Neurite Sprouting in PC12 Cells Involves Sigma-1 Receptors: Implications for Antidepressants," The Journal of Pharmacology and Experimental Therapeutics, vol. 303, No. 3, pp. 1227-1237 XP002536365 (2002).
Yagasaki et al., "Chronic Antidepressants Potentiate via Sigma-1 Receptors the Brain-Derived Neurotrophic Factor-Induced Signaling for Glutamate Release," The Journal of Biological Chemistry, vol. 281, No. 18, pp. 12941-12949, XP002536366 (2006).
Hisaoka et al., "Antidepressants Increaes Glial Cell Line-Derived Neurotrophic Factor Production through Monoamine-Independent Activation of Protein Tyrosine Kinase and Extrcellular Signal-Regulated Kinase in Glial Cells," The Journal of Pharmacology and Experimental Therapeutics, vol. 321, No. 1, pp. 148-157, XP002536367 (2007).
Werling et al., "A Comparison of the Binding Profiles of Dextromethorphan, Memantine, Fluoxentine and Amitriptyline: Treatment of Involuntary Emotional Expression Disorder," Experimental Neurology, vol. 207, No. 2, pp. 248-257, XP022265525 (2007).
Kikuchi-Utsumi et al., "Effects of Acute and Chronic Administrations of SA4503, A Sigma 1 Receptor Ligand, on BDNJ Expression in the Rat Brain," Journal of Pharmacological Society, vol. 106, No. Suppl. 1, p. 92, XP009119778 (2008).
International Search Report for International Application No. PCT/IE2009/000020, mailed Oct. 16, 2009.
Written Opinion for International Application No. PCT/IE2009/000020, mailed Oct. 16, 2009.

* cited by examiner

*Primary Examiner* — Brian J Davis
(74) *Attorney, Agent, or Firm* — Hunton & Williams LLP

(57) ABSTRACT

The invention provides a selective Sigma 1 or Dopamine D3 receptor agonist or a 5HT2c receptor ligand for use in the treatment of symptoms of anxiety and/or depression associated with an affective disorder and/or symptoms associated with cognitive impairment disorder. Particularly useful are diphenhydramine derivatives of Formula (I) and particularly (2-[(4-butylsulfanylphenyl)-phenyl-methyl]sulfanyl-N,N-dimethyl-ethanamin) (Captodiamine).

4 Claims, 14 Drawing Sheets

Target 1 Route

Formula II (captodiamine)

Formula I

PSYCHO-PHARMACEUTICALS

CROSS REFERENCE TO RELATED APPLICATIONS

This application is the National Phase application of International Application No. PCT/IE2009/000020, filed Apr. 20, 2009, which claims the benefit of priority to Ireland Patent Application No. S2008/0297, filed Apr. 18, 2008, the disclosures of each of which are herein incorporated by reference in their entireties.

TECHNICAL FIELD

The present invention relates to novel therapeutic uses of a growth factor modulating selective Sigma 1 or Dopamine D3 receptor agonist or a $5HT_{2c}$ receptor ligand, its derivatives, pharmaceutically acceptable salts thereof and mixtures thereof. In particular, the present invention relates to a growth factor modulating selective Sigma 1 or Dopamine D3 receptor agonist or a $5HT_{2c}$ receptor ligand, its derivatives, pharmaceutically acceptable salts thereof and mixtures thereof for use in the treatment of symptoms of anxiety and/or depression associated with an "affective" disorder in a subject in need of same.

BACKGROUND OF THE INVENTION

Depression is a serious illness associated with a high morbidity resulting from physical disorders and an increased mortality resulting from accidents and suicide. Major depression recurs in about half the patients diagnosed with depression. Major depression is characterized by feelings of intense sadness and despair, mental slowing and loss of concentration, pessimistic worry, agitation, and self-deprecation. Physical changes also occur, especially in severe or "melancholic" depression. These include insomnia or hypersomnia, anorexia and weight loss (or sometimes overeating), decreased energy and libido, and disruption of normal circadian rhythms of activity, body temperature, and many endocrine functions.

Treatment regimens commonly include the use of tricyclic antidepressants, monoamine oxidase inhibitors, some psychotropic drugs, lithium carbonate, and electroconvulsive therapy (ECT) (see, for example, R. J. Baldessarini in Goodman & Gilman's The Pharmacological Basis of Therapeutics, 9th Edition, Chapter 19, McGraw-Hill, 1996 for a review). More recently, new classes of antidepressant drugs are being developed including selective serotonin reuptake inhibitors (SSRIs), specific monoamine reuptake inhibitors and 5-HT1A receptor agonists, antagonists and partial agonists.

Thus, depressed patients may be treated with antidepressants continuously for years. There are, however, important drawbacks to the use of available drugs. Twenty-five % to thirty-five % of patients show only minimal improvement, and side effects and toxicity can occur. By way of example, tricyclic antidepressants (TCAs) are especially bothersome in elderly patients, with postural hypotension being a particularly severe problem and selective serotonin reuptake inhibitors (SSRIs) may induce nausea, vomiting, diarrhea, headache and sexual dysfunctions. Severe drug interactions can also result from the co-administration of monoamine oxidase inhibitors and either TCAs or SSRIs.

As a consequence, there is a need for antidepressant drugs that would be active at doses intended to be as low as possible in order to minimize the risk of side effects and drug interactions, especially in elderly patients, often exposed to several drugs concurrently.

Anxiety is an emotional condition characterized by feelings such as apprehension and fear accompanied by physical symptoms such as tachycardia, increased respiration, sweating and tremor. It is a normal emotion but when it is severe and disabling it becomes pathological. Anxiety-related impairments are frequent medical conditions, and include generalized anxiety disorders (GAD), panic anxiety, posttraumatic stress disorder, phobias, anxious depression, anxiety associated with schizophrenia, restlessness and general excitation states.

The main anxiolytic drugs used at present are benzodiazepines. Potent benzodiazepines are effective in panic disorder as well as in generalized anxiety disorder (GAD). In addition to their tranquillizing action, benzodiazepines also exert a variety of unwanted side effects, including sedative, anterograde amnesia and ethanol potentiation. However, the major factor limiting the therapeutic use of benzodiazepines are sequelae following their chronic use, in particular dependence liability. For a general review of benzodiazepines and their use in the treatment of anxiety-related disorders, see, for example, Schader and Greenblatt, 1993, N. Engl. J. Med. 328 (19): 1398-1405; and R. J. Baldessarini in Goodman & Gilman's Tite Pharmacological Basis of Therapeutics, 9th Edition, Chapter 18, McGraw-Hill, 1996.

Thus, there is a need for agents useful in treating the symptoms of anxiety-related disorders without, or with a decreased severity of, side effects, such as dependence liability and sedation. There is also a need for agents useful in the treatment of emotional, behavioural, neurological, and mental disorders, collectively referred to herein as "affective" all of which include anxiety and/or depression as a symptom.

Cognitive brain disorders are characterized clinically by progressive loss of memory, cognition, reasoning, executive functioning, planning, judgment and emotional stability, gradually leading to profound mental deterioration. A wide range of disorders can lead to disturbances of cognition. In particular, the increase of medical screening for dementia, has led to an increasing number of patients which are being identified who do not meet the diagnostic criteria for dementia but nonetheless have significant memory or cognitive impairment, defined as Mild Cognitive Impairment.

Mild Cognitive Impairment (MCI) is a condition characterized by mild recent memory loss without dementia or significant impairment of other cognitive functions to an extent that is beyond that expected for age or educational background. Criteria for diagnosis of MCI are: memory complaint; abnormal activities of daily living; abnormal general cognitive functioning; abnormal memory for age; not demented.

The number of patients falling in the categories of MCI, Age-Associated Memory Impairment, Age-Related Cognitive Decline or similar diagnostic categories is staggering. For example, according to the estimates of Barker et al. Br J Psychiatry, 1995 No 167(5):642-8, there are more than 16 million people with Age Associated Memory Impairment in the U.S. alone. An advisory panel to the US Food and Drug Administration ruled on Mar. 13, 2001, that MCI, "a condition separate from dementia in Alzheimer's Disease (AD)," is a valid target for new drug therapies, regardless of whether a particular drug also slows the progression to dementia. Only a few drugs are commercially available to improve cognitive function. Current therapies can cause unpleasant side-effects and lead to difficulties in maintaining patient compliance. In particular in some neuropsychological disease states, some interventions, often worsen cognitive functions. Thus, the need of new drugs that ameliorate cognition without worsening other side effects, is very high.

A variety of medications (including nonsteroidal anti-inflammatory drugs) hormones (especially estrogen), vitamins (such as, for example, vitamin E) and herbal preparations (especially Gingko biloba) have been advocated as treatments for cognitive impairment. Acetylcholinesterase inhibitors, labelled for use in Alzheimer's disease, are also being tested for MCI. Examples of acetylcholinesterase inhibitors tested for the treatment of MCI include but are not limited to Donepezil hydrochloride, or Aricept® described in U.S. Pat. No. 4,895,841, WO2001/066114 and EP1311272B1. While some of these agents hold promise, robust effects from carefully executed, well-controlled clinical trials are still nonexistent. For all these reasons the unmet medical need in cognitive impairment and, in particular, MCI, is still very high.

More recently, the sigma receptors have emerged as possible therapeutic targets for various diseases such neuropsychiatric disorders and cancer (Casellas et al., 2004; Hayashi and Su, 2004). The sigma receptors are widely distributed in the mammalian brain; and these receptors recognize a diverse array of centrally acting substances including opiates, antipsychotics, antidepressants, phencyclidine (PCP)-related compounds, and neurosteroids (Walker et al., 1990; Bowen, 2000). Moreover, the observation that several sigma receptor ligands are neuroprotective in both in vivo and in vitro models of ischemia has generated great interest in targeting these receptors to enhance neuronal survival following stroke (Takahashi et al., 1996; Lockhart et al., 1995). Dysregulation of intracellular calcium homeostasis greatly contributes to the demise of neurons following an ischemic insult in the central nervous system. The sigma receptors have also been implicated in numerous physiological and pathophysiological processes such as learning and memory (Senda et al., 1996; Hiramatsu et al., 2006), movement disorders (Matsumoto et al., 1990), and drug addiction (McCracken et al., 1999).

So far, two sigma receptor subtypes have been identified on the basis of their pharmacological profile. Only the sigma-1 receptor has been cloned (Hanner et al., 1996). However, the sigma-2 receptor has been shown to be a separate molecular entity (Langa et al., 2003). The sigma-1 receptor has high affinity for positive isomer of bezomorphas such as (+)-pentazocine and (+)-SKF-10,047 while the sigma-2 receptor has a high affinity for ibogaine (Vilner and Bowen, 2000). In particular, sigma 1 receptor agonists have also been shown to have antidepressant effects. In this regard, Sigma 1 receptor ligands show clear antidepressant effects in several animal models. By way of example, the selective sigma 1 receptor agonists (+)-pentazocine, (+)-SKF-10,047, igmesine, OPC14523, DTG or SA4503 reduce the immobility time in the forced swim test or are active in the tail suspension test (Ukai et al. 1998, Matsuno et al., 1996, Tottori et al. 1997, Kinsora et al. 1998). U.S. Pat. No. 5,034,419 describes N-cycloalkylalkylamines, which are also sigma 1 receptor agonist.

The function and mechanism of action of the sigma receptors is not well understood. Accordingly, studies of sigma receptor modulation of biological processes have resulted in considerable controversy in the literature. There are conflicting reports as to whether sigma receptor ligands, such as sigma 1 receptor agonists/antagonists, exert their effects via actions on sigma receptors (Hayashi et al., 1995; Monnet et al., 2003) or non-specific interaction with other targets, in particular, NMDA receptors (Nishikawa et al., 2000; Kume et al., 2002). To some extent, analysis and interpretation of the results has been confounded by limitations in the pharmacological approaches used. For example, sigma receptors and NMDA receptors both bind PCP and related compounds (eg. MK-801) with high affinity (Sircar et al., 1987), and thus, such drugs cannot be used to discriminate between direct and indirect effects. Also, previous studies have not effectively used specific sigma receptor antagonists to confirm results.

Captodiamine (Covatine) has been known as an anxiolytic agent for several decades. Azoulay, Le Bezu and Leyritz (Ann. Med. Psychol. (Paris), 1956 December 114 (5); 856-861 reported a study on the treatment with Covatine of "depressive states" resistant to largactil. Covatine was found to be useful in only one patient (observation 1), a patient in a depressive state with suicidal ideation who was subsequently diagnosed to have a major anxiety behavior and to be "depressed". The most appropriate interpretation of the terms "depressed" and "depressive state" used in this paper is in relation to an emotional and/or deflated state. In 1956, depression and schizophrenia were classified as psychotic states and anxiety, along with "depressive reactions", were referred to as neuroses (Bowman and Rand, 1980). This is consistent with the diagnosis of the patent Observation 1 as being a case of neurosis. Secondly, the effects of Covatine in this study were concluded to be ineffective in the treatment of individuals with psychosis (Grebe, 1959).

From the discussion above, it is clear that the treatment of: (a) symptoms of anxiety and/or depression associated with an "affective" disorder; and/or (b) symptoms associated with a cognitive impairment disorder is still an area of high unmet medical need with no effective drugs. Despite intensive research into the mechanism of the pathogenesis of these diseases and the development of new drugs for effective treatment of this disease, there also remains a significant interest in and need for additional or alternative therapies for treating, preventing and/or delaying the onset and/or development of symptoms associated with cognitive impairment disorders, and/or symptoms of anxiety and/or depression associated with "affective" disorders. The moderate and inconsistent effect observed with some drugs leave space to identify more effective and safe treatments. In particular, there is a need for additional or alternative therapies which have efficacy in managing the core symptoms associated with cognitive impairment disorders, and/or symptoms of anxiety and/or depression associated with "affective" disorders. In particular, there is a need for new therapeutic agents which can improve the quality of life for patients with symptoms associated with these disorders.

SUMMARY OF THE INVENTION

The invention relates to growth factor modulating selective Sigma 1 or Dopamine D3 receptor agonist or a $5HT_{2c}$ receptor ligand for use in the treatment of emotional, behavioral, neurological, and mental disorders, collectively referred to herein as "affective" disorders, all of which include anxiety and/or depression as a symptom. In this regard, anxiety may be present with or without other disorders such as depression. Mixed anxiety/depressive disorders include anxiety in the presence of depressive symptoms or exclude anxiety in the absence of depressive symptoms. The compounds and/or the compositions of the present invention are therefore useful in the treatment of symptoms of anxiety with or without the accompanying symptoms of depression. The present invention also relates to the use of growth factor modulating selective Sigma 1 or Dopamine D3 receptor agonist or a $5HT_{2c}$ receptor ligand as cognitive enhancers, for example, to enhance learning and memory.

The prior art is replete with reference, discussed below, which demonstrate that growth factors, such as neurotrophic growth factors, regulate the proliferation and survival of neurons. To the Applicants knowledge, there is no example in the literature that a selective Sigma 1 receptor agonist could have a positive effect in the treatment of symptoms of anxiety and/or depression associated with "affective" disorders, and/or symptoms associated with a cognitive impairment disorder by modulating the expression levels and/or functional activity of a growth factor biological mediator, such as GDNF. In particular, to the Applicants knowledge, there is no example in the literature that a selective Sigma 1 receptor agonist could have a positive effect in the treatment of symptoms of anxiety and/or depression associated with "affective" disorders, and/or symptoms associated with a cognitive impairment disorder by modulating the expression levels and/or functional activity of a growth factor biological mediator, such as GDNF, in a region specific area of the brain, such as the pre-frontal cortex of the brain.

Given the lack of previous demonstration that a selective Sigma 1 receptor agonist has anti-depressive properties, anxiolytic enhancing properties and cognitive enhancing properties as well as growth factor modulating properties, in particular, GDNF modulating properties in the pre-frontal cortex of the brain, the present findings are unexpected. The advantages derived from the uses and the methods and the compositions of the present invention as defined below are many, and include the possibility to treat all types of symptoms of anxiety and/or depression associated with an affective disorder and/or symptoms associated with a cognitive impairment disorder using a growth factor modulating selective Sigma 1 or Dopamine D3 receptor agonist or a 5HT$_{2c}$ receptor ligand with a surprisingly favourable profile of safety. The fact that growth factor modulating selective sigma 1 receptor agonists, may have a different mechanism of action from that of serotonin reuptake inhibitors (or other monoamine transporter inhibitors), may also be of benefit in subjects with symptoms of anxiety and/or depression which are not responsive to monoamine transporter inhibitors. Other advantages are discussed and are made apparent in the following commentary.

Accordingly, the present invention in a first aspect provides a compound comprising a growth factor modulating selective Sigma 1 or Dopamine D3 receptor agonist or a 5HT$_{2c}$ receptor ligand or a pharmaceutically acceptable salt thereof or a mixture thereof for use in the treatment of: (a) symptoms of anxiety and/or depression associated with an "affective" disorder; and/or (b) symptoms associated with a cognitive impairment disorder in a subject in need of same. In the case where the compound is a Sigma 1 receptor agonist, the compound selectively or preferentially binds to or activates the Sigma 1 receptor as compared to the Sigma 2 receptor. The compound of the invention ideally modulates GDNF expression and/or functional activity, preferably in the pre-frontal cortex of the brain, and in one embodiment it decreases GDNF expression levels and/or functional activity, preferably in the pre-frontal cortex of the brain. The "affective disorder" may comprise symptoms of anxiety and/or depression.

In a preferred aspect, the compound according to the invention has the structure of Formula I below;

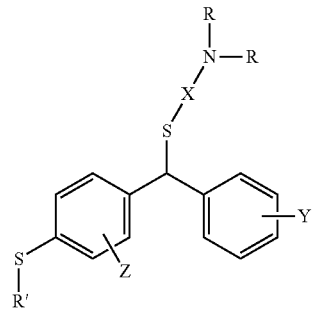

FORMULA I wherein
X is an ethylene, propylene, butylene or pentylene group;
R is C$_{1-9}$ alkyl, preferably C$_{1-5}$ alkyl;
R' is C$_{1-9}$ alkyl, alkenyl or alkynyl;
Y is hydrogen, halide such as chloro, fluoro, iodo or bromo, hydroxyC$_{1-4}$alkyl, amino, C$_{1-4}$alkylamino, acetylamino or thio; and
Z is hydrogen, halide such as chloro, fluoro, iodo or bromo, hydroxyC$_{1-4}$alkyl, amino, C$_{1-4}$alkylamino, acetylamino or thio, or a pharmaceutically acceptable salt thereof.

X may be an ethylene, propylene, butylene, or pentylene group and R is methyl, R' is butyl, Y is hydrogen and Z is hydrogen; or R is C$_{1-9}$ alkyl, preferably C$_{1-5}$ alkyl, and R' is butyl, X is ethylene, Y is hydrogen and Z is hydrogen.

Y may be hydrogen, halide such as chloro, fluoro, iodo or bromo, hydroxyC$_{1-4}$alkyl, amino, C$_{1-4}$alkylamino, acetylamino, thio and R is methyl, R' is butyl, X is ethylene and Z is hydrogen.

Z may be hydrogen, halide such as chloro, fluoro, iodo or bromo, hydroxyC$_{1-4}$alkyl, amino, C$_{1-4}$alkylamino, acetylamino, thio and R is methyl, R' is butyl, X is ethylene and Y is hydrogen.

R' may be C$_{1-9}$ alkyl, alkenyl or alkynyl and R is methyl, X is ethylene, Y is hydrogen and Z is hydrogen.

In a preferred arrangement, the compound is 2-[(4-butylsulfanylphenyl)-phenylmethyl]sulfanyl-N,N-dimethylethanamine (Captodiamine).

In another aspect, the invention provides a pharmaceutical composition comprising a pharmaceutically acceptable carrier and, as an active ingredient, an effective amount of the compound described above for use in the treatment of symptoms of anxiety and/or depression associated with an "affective" disorder and/or (b) symptoms associated with a cognitive impairment disorder in a subject in need of same. The composition may include one or more agents selected the group consisting of: (i) an anti-depressant agent; (ii) an anxiolytic agent; and (iii) a cognitive enhancing agent, and the treatment may comprise the simultaneous or sequential administration of a compound as defined above and one or more agents selected the group consisting of: (i) an anti-depressant agent; (ii) an anxiolytic agent; and (iii) a cognitive enhancing agent.

Also provided is a process for preparing a pharmaceutical composition as described above wherein the process comprises mixing a compound as defined above and one or more agents selected from the group consisting of: (i) an anti-depressant agent; (ii) an anxiolytic agent; and (iii) a cognitive enhancing agent In another aspect, there is provided a diphenhydramine derivative or a pharmaceutically acceptable salt thereof or a mixture thereof for use in the treatment of symptoms of anxiety and/or depression associated with an "affective" disorder; and/or (b) symptoms associated with a cognitive impairment disorder; in a subject in need of same. The diphenhydramine derivative or a pharmaceutically acceptable salt thereof or a mixture thereof has use in the treatment of symptoms of depression associated with an "affective-related" disorder in a subject in need of same, or for use in the treatment of symptoms of anxiety and depression associated with an "affective-related" disorder in a subject in need of same, or for use in the treatment of symptoms associated with a cognitive impairment disorder; in a subject in need of same. Ideally, the derivative is 2-[(4-butylsulfanylphenyl)-phenyl-methyl]sulfanyl-N,N-dimethylethanamine (Captodiamine).

Further, the invention provides a pharmaceutical composition comprising Captodiamine and an agomelatin (Valdoxan). Such a composition has use in the treatment of symptoms of anxiety and/or depression associated with an "affective" disorder; and/or (b) symptoms associated with a cognitive impairment disorder.

In another aspect, there is provided a process for identifying a compound capable of modulating the expression levels and/or functional activity of a Sigma 1 or Dopamine D3 receptor agonist or a $5HT_{2c}$ receptor ligand comprising assaying for the ability of the compound to modulate the activity of GDNF. Also provided is a compound that modulates the expression levels and/or functional activity of GDNF as identified by the process.

Yet further, the invention provides a compound that modulates the expression levels and/or functional activity of a selective Sigma 1 or Dopamine D3 receptor agonist or a $5HT_{2c}$ receptor ligand by modulating the expression levels and/or functional activity of GDNF for use in the treatment of symptoms of anxiety and/or depression associated with an "affective" disorder; and/or (b) symptoms associated with a cognitive impairment disorder. Also provided is a compound comprising a growth factor modulating selective Sigma 1 or Dopamine D3 receptor agonist or a $5HT_{2c}$ receptor ligand or a pharmaceutically acceptable salt thereof or a mixture thereof for use in the treatment of (a) symptoms of anxiety and/or depression and/or cognitive impairment associated with a derangement of GDNF signaling in the brain pre-frontal cortex of a subject wherein the treatment comprise administering an effective amount of a GDNF modulating selective Sigma 1 or Dopamine D3 receptor agonist or a 5HT2c receptor ligand or a pharmaceutically acceptable salt thereof or a mixture thereof to decrease GDNF expression levels in the pre-frontal cortex of the subject's brain.

The compound of Formula I as defined above or a pharmaceutically acceptable salt thereof has use in the treatment of symptoms of anxiety and/or depression associated with an "affective" disorder; and/or (b) symptoms associated with a cognitive impairment disorder; in a subject in need of same.

ASPECTS OF THE INVENTION

Thus, the invention provides a growth factor modulating selective Sigma 1 and/or Dopamine D3 receptor agonist and/or a $5HT_{2c}$ receptor ligand for use in the treatment of:
(a) symptoms of anxiety and/or depression associated with an "affective" disorder; and/or
(b) symptoms associated with a cognitive impairment disorder in a subject in need of same.

The invention is based, at least in part, on the discovery that a growth factor modulating selective Sigma 1 or Dopamine D3 receptor agonist or a $5HT_{2c}$ receptor ligand, such as Captodiamine, is a potent anti-depressive and/or anti-anxiety agent which can modify behaviour, and enhance cognitive performance. Thus, the growth factor modulating selective Sigma 1 or Dopamine D3 receptor agonist or a $5HT_{2c}$ receptor ligand can thus be used to treat (by, for example, reducing symptoms of) affective disorders which include anxiety and/or depression as a symptom as described herein and/or cognitive impairment disorders.

In addition, a growth factor modulating selective Sigma 1 or Dopamine D3 receptor agonist or a $5HT_{2c}$ receptor ligand may be used more generally to reduce anxiety in both humans and animals.

Thus, the invention also provides a growth factor modulating selective Sigma 1 or Dopamine D3 receptor agonist or a $5HT_{2c}$ receptor ligand for use in the treatment of anxiety in a subject in need of same wherein the growth factor modulating selective Sigma 1 or Dopamine D3 receptor agonist or a $5HT_{2c}$ receptor ligand is administered in an amount effective to reduce anxiety.

Growth factor modulating selective Sigma 1 or Dopamine D3 receptor agonist or a $5HT_{2c}$ receptor ligand may also be used to enhance cognition, including learning and memory.

The invention also provides a growth factor modulating selective Sigma 1 or Dopamine D3 receptor agonist or a $5HT_{2c}$ receptor ligand for use in enhancing cognition in a subject in need of same wherein the growth factor modulating selective Sigma 1 or Dopamine D3 receptor agonist or a $5HT_{2c}$ receptor ligand is administered in an amount effective to enhance learning and memory (such as, for example, where enhancement of learning and/or memory is measured by improvement on a Wisconsin Card Sort Test as discussed below) or measured by an improvement in memory or an improvement in both learning and memory in the subject without, for example, causing adverse side effects.

An important advantage of the growth factor modulating selective sigma receptor agonists is their efficacy without adverse side-effects in a subject. In contrast, conventional antidepressants and antianxiety drugs typically lead to adverse side-effects that can include sedation, cognitive impairment, appetite stimulation, tardive dyskinesia (irreversible, involuntary movement disorder), extrapyramidal symptoms, and akathesia symptoms. Side effects are one of the major reasons for medical noncompliance in the outpatient treatment of affective disorders, such as anxiety disorders. Because they lack significant side effects, growth factor modulating selective Sigma 1 or Dopamine D3 receptor agonist or a $5HT_{2c}$ receptor ligand represents an improvement over those drugs that cause side effects.

Also encompassed by the invention are pharmaceutical compositions for use as medicaments for use in the treatment of: (a) symptoms of anxiety and/or depression associated with an "affective" disorder; and/or (b) symptoms associated with a cognitive impairment disorder in a subject in need of same wherein the composition comprises a pharmaceutically acceptable carrier and, as an active ingredient, an effective amount of a growth factor modulating selective Sigma 1 or Dopamine D3 receptor agonist or a $5HT_{2c}$ receptor ligand.

The invention additionally includes uses of pharmaceutical compositions for the manufacture of medicaments for treating (a) symptoms of anxiety and/or depression associated with an "affective" disorder; and/or (b) symptoms associated with a cognitive impairment disorder in a subject in need of same wherein the composition comprises a pharmaceutically acceptable carrier and, as an active ingredient, an effective amount of a growth factor modulating selective Sigma 1 or Dopamine D3 receptor agonist or a $5HT_{2c}$ receptor ligand.

In addition, the invention includes kits that include a pharmaceutical composition comprising a growth factor modulating selective sigma 1 agonist and instructions for its use in treating (a) symptoms of anxiety and/or depression associated with an "affective" disorder; and/or (b) symptoms associated with a cognitive impairment disorder in a subject in need of same.

The growth factor modulating selective Sigma 1 or Dopamine D3 receptor agonist or a $5HT_{2c}$ receptor ligand of the present invention may be used alone or in conjunction with other agents, including other anti-depressant agents, anxiolytic agents and/or cognitive enhancing agents.

Preferred growth factor modulating selective Sigma 1 or Dopamine D3 receptor agonist or a $5HT_{2c}$ receptor ligand for use according to the present invention include but are not limited to compounds such as diphenhydramine derivative compounds. Even more preferred compounds include but are not limited to the compounds represented by Formula I or Formula II and variants, derivatives and mimetics thereof. The most preferred compound is 2-[(4-butylsulfanylphenyl)-phenylmethyl]sulfanyl-N,N-dimethylethanamine (Captodiamine).

Captodiamine is disclosed in U.S. Pat. Nos. 3,947,579, 4,084,000, 4,129,652 and 4,138,484 for use in the treatment of schizophrenia. A process for preparing Captodiamine is also disclosed in U.S. Pat. No. 2,830,088. Captodiamine may be prepared using the process disclosed in U.S. Pat. No. 2,830,088. Alternatively, Captodiamine may be custom synthesized using the process disclosed in FIG. 13. Known properties in the published literature for Captodiamine include its sedative properties (see, for example, Dobkin, A B, Can Anaes Soc J (1958) 5(2) 177-208). There is no disclosure or suggestion in any of the above references that growth factor modulating selective Sigma 1 or Dopamine D3 receptor agonist or a $5HT_{2c}$ receptor ligand, such as Captodiamine, could be used for the treatment of symptoms of anxiety and/or depression associated with an "affective" disorder; and/or (b) symptoms associated with a cognitive impairment disorder in a subject in need of same.

The advantages of using growth factor modulating selective Sigma 1 or Dopamine D3 receptor agonist or a $5HT_{2c}$ receptor ligand, such as Captodiamine, in the instant invention include the relatively nontoxic nature of the compound, the ease of preparation, the fact that the compound is well tolerated, and the ease of oral administration of the drug.

The present invention thus provides a diphenhydramine derivative, or a compound of Formula I, such as Captodiamine, or a pharmaceutically acceptable salt thereof or a mixture thereof for use in the treatment of symptoms of anxiety and/or depression associated with an "affective" disorder; and/or (b) symptoms associated with a cognitive impairment disorder; in a subject in need of same.

The subject invention also provides for a pharmaceutical composition comprising a pharmaceutically acceptable carrier and, as an active ingredient, a diphenhydramine derivative, or a compound of Formula I, such as Captodiamine, or a pharmaceutically acceptable salt thereof or a mixture thereof for the treatment of symptoms of anxiety and/or depression associated with an "affective" disorder; and/or (b) symptoms associated with a cognitive impairment disorder; in a subject in need of same.

There is also provided a growth factor modulating selective Sigma 1 or Dopamine D3 receptor agonist or a $5HT_{2c}$ receptor ligand or a pharmaceutically acceptable salt thereof or a mixture thereof for use in the treatment of: (a) symptoms of anxiety and/or depression and/or cognitive impairment associated with a derangement of GDNF signaling in the pre-frontal cortex of the brain of a subject wherein the treatment comprise administering an effective amount of a GDNF modulating selective Sigma 1 or Dopamine D3 receptor agonist or a $5HT_{2c}$ receptor ligand or a pharmaceutically acceptable salt thereof or a mixture thereof to decrease GDNF expression levels in the pre-frontal cortex of the subject's brain.

Other features and advantages of the invention will be apparent from the following detailed description, and from the claims.

DETAILED DESCRIPTION OF THE INVENTION

Various terms that will be used throughout the specification have meanings that will be well understood by the skilled addressee. However, for ease of reference, some of these terms will now be defined.

Growth Factor

As used herein, the term "growth factor" refers to a naturally occurring protein capable of stimulating cellular proliferation and cellular differentiation. Growth factors are important for regulating a variety of cellular processes. Growth factors typically act as signaling molecules between cells. Examples include but are not limited to cytokines and hormones that bind to specific receptors on the surface of their target cells. They often promote cell differentiation and maturation, which varies between growth factors. By way of example, bone morphogenic proteins stimulate bone cell differentiation, while fibroblast growth factors and vascular endothelial growth factors stimulate blood vessel differentiation (angiogenesis). The term "growth factor" is sometimes used interchangeably among scientists with the term cytokine. Historically, cytokines were associated with hematopoietic (blood forming) cells and immune system cells (such as, for example, lymphocytes and tissue cells from spleen, thymus, and lymph nodes). In relation to the circulatory system and bone marrow, in which cells can occur in a liquid suspension and not bound up in solid tissue, it makes sense for them to communicate by soluble, circulating protein molecules. However, as different lines of research converged, it became clear that some of the same signaling proteins which the hematopoietic and immune systems used were also being used by all sorts of other cells and tissues, during development and in the mature organism.

Several well known growth factors include but are not limited to Transforming growth factor beta (TGF-β), Granulocyte-colony stimulating factor (G-CSF), Granulocyte-macrophage colony stimulating factor (GM-CSF), Nerve growth factor (NGF), Neurotrophins, Platelet-derived growth factor (PDGF), Erythropoietin (EPO), Thrombopoietin (TPO), Myostatin (GDF-8), Growth differentiation factor-9 (GDF9), Acidic fibroblast growth factor (aFGF or FGF-1), Basic fibroblast growth factor (bFGF or FGF-2), Epidermal growth factor (EGF), and Hepatocyte growth factor (HGF). Individual growth factor proteins tend to occur as members of larger families of structurally and evolutionarily related proteins. In this respect, there are dozens and dozens of growth factor families such as TGF-beta (transforming growth factor-beta), BMP (bone morphogenic protein), fibroblast growth factor (FGF), neurotrophins (NGF, BDNF, and NT3), and the like.

The Neurotrophins, are a family of proteins, which induce the survival of neurons. They belong to a class of growth factors, secreted proteins, which are capable of signaling particular cells to survive, differentiate, or grow. Growth factors, such as neurotrophins, that promote the survival of neurons are known as neurotrophic factors. Neurotrophic factors are secreted by target tissue and act by preventing the associated neuron from initiating programmed cell death—thus allowing the neurons to survive. Neurotrophins also induce differentiation of progenitor cells, to form neurons. Some scientists employ the term "neurotrophin" as a synonym for "neurotrophic factor", while most reserve the term "neurotrophin" for four structurally related factors-nerve growth factor (NGF), brain-derived neurotrophic factor (BDNF), neurotrophin-3 (NT-3), and neurotrophin-4 (NT-4). Another neurotrophic factor, known as novel neurotrophin-1 (NNT1) is structurally unrelated to NGF, BDNF, NT-3 and NT-4. Other neurotrophins include but are not limited to the GDNF family of ligands (GFL) which consists of four neurotrophic factors: glial cell line-derived neurotrophic factor (GDNF) neurturin (NRTN), artemin (ARTN) and persephin (PSPN). GFLs have been shown to play a role in a number of biological processes including cell survival, neurite outgrowth, cell differentiation and cell migration. In particular signalling by GDNF promotes the survival of dopaminergic neurons.

GDNF

As used herein, the term "GDNF" means Glial cell Derived Neurotrophic Factor, also known as GDNF, is a small protein that potently promotes the survival of many types of neurons. The most prominent feature of GDNF is its ability to support the survival of dopaminergic and motorneurons.

By way of background information, GDNF was first described as a stimulant of survival of dopaminergic neurons in-vitro (Lin, et al. (1993) Science 260: (5111), 1130-1132) and was found to belong to the transforming growth factor-beta superfamily (also known as the TGF beta family). In this regard, structural motifs including six cysteine residues suggested that GDNF is a distant member of the TGF-β superfamily of growth and differentiation factors (Lin et al. 1993). Shortly after its discovery, GDNF was demonstrated to have protective effects in in-vivo models of Parkinson's Disease (Kaddis, et al. (1996) Cell Tissue Res. 286: (2), 241-247; Gash, et al. (1996) Nature 380: (6571), 252-255; Choi-Lundberg, et al. (1997) Science 275: (5301), 838-841), on dorsal root ganglion neurons (Matheson, et al. (1997) J Neurobiol. 32: (1), 22-32), and on motor neurons during development (Oppenheim, et al. (1995) Nature 373: (6512), 344-346).

GDNF interacts with a specific cell-surface receptor, GFRA1 (Jing, et al. (1996) Cell 85: (7), 1113-1124; Treanor, et al. (1996) Nature 382: (6586), 80-83), and its biological effects are mediated through the interaction of GDNF, GFRA1, and a tyrosine kinase receptor, RET (Takahashi, et al. (1987) Mol Cell Biol 7: (4), 1378-1385). Both GDNF and its receptors are synthesized in the retina (Jing, et al. (1996) Cell 85: (7), 1113-1124; Nosrat, et al. (1996) Cell Tissue Res. 286: (2), 191-207; Pachnis, et al (1993) Development 119: (4), 1005-1017). U.S. Pat. No. 5,733,875 discloses the use of GDNF as a neuroprotective agent in connection with seizures and U.S. Pat. Nos. 5,736,516 and 5,641,750 relates to methods for treating photoreceptors using GDNF protein. A method for treating Alzheimer's disease using GDNF is disclosed in U.S. Pat. No. 5,731,284.

The complete GDNF coding sequence and deduced amino acid sequence is deposited as GenBank Accession Nos. L19063 and L15306. The protein is synthesised as a prepropeptide that is cleaved to a predicted active mature protein of 134 amino acid residues. GDNF mRNA is widely expressed at low levels in neurons in many areas of the brain, such as cortex, hippocampus, striatum, substantia nigra, thalamus, cerebellum, and of the spinal cord (Pochon et al. Eur. J. Neurosci. 9: 463-471, 1997) and is upregulated upon excitation (Humpel et al., Neuroscience 59: 791-795, 1994; Schmidt-Kastner et al., Mol. Brain Res. 26: 325-330, 1994).

BDNF

Brain-derived neurotrophic factor (BDNF) is a neurotrophic factor found in the brain and the periphery. It is a protein that acts on certain neurons of the central nervous system and the peripheral nervous system that helps to support the survival of existing neurons and encourage the growth and differentiation of new neurons and synapses. In the brain, it is active in the hippocampus, cortex, and basal forebrain, which are areas vital to learning, memory, and higher thinking. BDNF was the second neurotrophic factor to be characterized after nerve growth factor (NGF).

Although the vast majority of neurons in the mammalian brain are formed prenatally, parts of the adult brain retain the ability to grow new neurons from neural stem cells in a process known as neurogenesis. Neurotrophins are chemicals that help to stimulate and control neurogenesis, BDNF being one of the most active. Mice born without the ability to make BDNF suffer developmental defects in the brain and sensory nervous system, and usually die soon after birth, suggesting that BDNF plays an important role in normal neural development.

Despite its name, BDNF is actually found in a range of tissue and cell types, not just in the brain. It is also expressed in the retina, the CNS, motor neurons, the kidneys, and the prostate. Exposure to stress and the stress hormone corticosterone has been shown to decrease the expression of BDNF in rats, and leads to an eventual atrophy of the hippocampus if exposure is persistent. Similar atrophy has been shown to take place in humans suffering from chronic depression. In addition, rats bred to be heterozygous for BDNF, therefore reducing its expression, have been observed to exhibit similar hippocampal atrophy, suggesting that an etiological link between the development of depressive illness and regulation of BDNF exists. On the other hand, the excitatory neurotransmitter glutamate, voluntary exercise, caloric restriction, intellectual stimulation, and various treatments for depression (such as antidepressants and electroconvulsive therapy) strongly increase expression of BDNF in the brain, and have been shown to protect against this atrophy.

BDNF binds at least two receptors on the surface of cells which are capable of responding to this growth factor, TrkB (pronounced "Track B") and the LNGFR (for "low affinity nerve growth factor receptor", also known as p75). TrkB is a receptor tyrosine kinase (meaning it mediates its actions by causing the addition of phosphate molecules on certain tyrosines in the cell, activating cellular signaling). There are other related Trk receptors, TrkA and TrkC. Also, there are other neurotrophic factors structurally related to BDNF: NGF (for Nerve Growth Factor), NT-3 (for Neurotrophin-3) and NT-4 (for Neurotrophin-4). While TrkB mediates the effects of BDNF and NT-4, TrkA binds and is activated by NGF, and TrkC binds and is activated by NT-3. NT-3 binds to TrkA and TrkB as well, but with less affinity. The other BDNF receptor, the LNGFR, plays a somewhat less clear role. Some researchers have shown the LNGFR binds and serves as a "sink" for neurotrophins. Cells which express both the LNGFR and the Trk receptors might therefore have a greater activity—since they have a higher "microconcentration" of the neurotrophin. It has also been shown, however, that the LNGFR may signal a cell to die via apoptosis—so therefore cells expressing the LNGFR in the absence of Trk receptors may die rather than live in the presence of a neurotrophin.

Various studies have shown possible links between low levels of BDNF and conditions such as depression, schizophrenia, Obsessive-compulsive disorder (OCD), Alzheimer's disease, Huntington's disease, Rett syndrome, and dementia, as well as anorexia nervosa and bulimia nervosa, though it is still not known whether these levels represent a cause or a symptom. By way of example, epilepsy has also been linked with polymorphisms in BDNF. Given BDNF's vital role in the development of the landscape of the brain, there is quite a lot of room for influence on the development of neuropathologies from BDNF.

Levels of both BDNF mRNA and BDNF protein are known to be up-regulated in epilepsy (Gall C, et. al. 1991 Gall C, Lauterborn J, Bundman M, Murray K, Isackson P (1991). "Seizures and the regulation of neurotrophic factor and neuropeptide gene expression in brain". *Epilepsy Res. Suppl.* 4: 225-45. PMID 1815605.). BDNF modulates excitatory and inhibitory synaptic transmission by inhibiting GABAA-receptor mediated post-synaptic currents. This provides a potential reason for the observed up-regulation.

Modulator

The term "modulator" as used herein refers to an agent capable of changing, for example, a pharmacological functional activity and/or an expression level and/or a behavioural response relative to a normal or reference level of a pharmacological functional activity and/or an expression level and/or a behavioural response under the same conditions. For example, a pharmacological functional activity and/or an expression level and/or a behavioural response may be greater or lesser than that of a reference entity. The term "modulator" includes, but is not limited to, agonists and antagonists. The term "modulators" also includes analogs, mimetics and the like. Modulators can work in concert or in opposition to other agents.

As used herein, the term "modulate" or "modulating" or "modulation" refers to any change in, for example, a pharmacological functional activity and/or an expression level and/or a behavioural response relative to a normal or reference level of a pharmacological functional activity and/or an expression level and/or a behavioural response under the same conditions. For example, a pharmacological functional activity and/or an expression level and/or a behavioural response may be greater or lesser than that of a reference entity.

As used herein, the various forms of the term "modulate" include potentiating (such as, for example, increasing or upregulating or improving or enhancing a particular behavioural response and/or pharmacological function activity and/or an expression level) and inhibiting (such as, for example, decreasing or downregulating a particular behavioural response and/or pharmacological function activity and/or an expression level). The potentiating and/or inhibiting can take place directly or indirectly and/or competitively and/or non-competitively (such as, for example, working at a site which is distal to receptor rather than at a receptor site itself). By way of example, the behavioural response and/or pharmacological function activity and/or an expression level of an entity may be modulated indirectly, such as, for example, by modulating the activity of a molecule, such as an effector molecule, that is upstream or downstream of the entity in a signal transduction pathway involving that entity.

By way of example, modulating a cognitive function by improving or enhancing a cognitive function includes "promoting" a cognitive function (affecting impaired cognitive function in the subject so that it more closely resembles the function of an aged-matched normal, unimpaired subject, including affecting states in which cognitive function is reduced compared to a normal subject) and "preserving" cognitive function (affecting normal or impaired cognitive function such that it does not decline or does not fall below that observed in the subject upon first presentation or diagnosis, such as, for example, to the extent of expected decline in the absence of treatment).

Growth Factor Modulating

As used herein, the term "Growth Factor modulation" means any change of, for example, a growth factor functional activity and/or a growth factor expression level and/or a growth factor associated behavioural response relative to a normal or reference level of a functional activity and/or an expression level and/or a behavioural response under the same conditions. For example, a growth factor functional activity and/or a growth factor expression level and/or a growth factor associated behavioural response may be greater or lesser than that of a reference entity. The term "growth factor modulator" includes, but is not limited to growth factor agonists and antagonists. The term "growth factor modulator" also includes analogs, mimetics and the like. Modulators can work in concert or in opposition to other agents. Growth Factor modulation may be Growth Factor Specific and/or Receptor Specific and/or Region Specific. As demonstrated in the Examples, the modulation of a BDNF growth factor appears to be specific for the hypothalamus region of the brain while the modulation of GDNF growth factor appears to be specific for the prefrontal cortex of the brain. Thus, Growth Factor modulation may "region specific" in the sense that Growth Factor modulation may be specific for a particular region of the brain.

As used herein, the term "GDNF modulating" means any change of, for example, a GDNF functional activity and/or a GDNF expression level and/or a growth factor associated behavioural response relative to a normal or reference level of a functional activity and/or an expression level and/or a behavioural response under the same conditions. For example, a GDNF functional activity and/or a GDNF expression level and/or a GDNF associated behavioural response may be greater or lesser than that of a reference entity. The term "GDNF modulator" includes, but is not limited to a GDNF agonists and antagonists. The term "GDNF modulator" also includes analogs, mimetics and the like. GDNF modulators can work in concert or in opposition to other agents. GDNF modulation may be Factor Specific and/or Receptor Specific and/or Region Specific. As demonstrated in the Examples, the modulation of GDNF growth factor appears to be specific for the prefrontal cortex of the brain.

As used herein, the term "BDNF modulating" means any change of, for example, a BDNF functional activity and/or a BDNF expression level and/or a growth factor associated behavioural response relative to a normal or reference level of a functional activity and/or an expression level and/or a behavioural response under the same conditions. For example, a BDNF functional activity and/or a BDNF expression level and/or a BDNF associated behavioural response may be greater or lesser than that of a reference entity. The term "BDNF modulator" includes, but is not limited to BDNF agonists and antagonists. The term "BDNF modulator" also includes analogs, mimetics and the like. BDNF modulators can work in concert or in opposition to other agents. BDNF modulation may be Factor Specific and/or Receptor Specific and/or Region Specific. As demonstrated in the Examples, the modulation of BDNF growth factor appears to be specific for the hypothalamic region of the brain.

Region Specific Areas of the Brain

Regardless of the animal, brains have the following parts: Brain stem, Cerebellum, Hypothalamus and pituitary gland, Cerebrum (also called the cerebral cortex or just the cortex).

The brain stem consists of the medulla (an enlarged portion of the upper spinal cord), pons and midbrain (lower animals have only a medulla). The brain stem controls the reflexes and automatic functions (heart rate, blood pressure), limb movements and visceral functions (digestion, urination). The cerebellum integrates information from the vestibular system that indicates position and movement and uses this information to coordinate limb movements. These control visceral functions, body temperature and behavioural responses such as feeding, drinking, sexual response, aggression and pleasure. The cerebrum consists of the cortex, large fiber tracts (corpus callosum) and some deeper structures (basal ganglia, amygdala, hippocampus). It integrates information from all of the sense organs, initiates motor functions, controls emotions and holds memory and thought processes (emotional expression and thinking are more prevalent in higher mammals).

Prefrontal Cortex

The pre-frontal cortex of the brain is associated with the sensory processing function of the brain, including its "plasticity" function as synaptic plasticity is relevant for cognitive function. The Prefrontal Cortex is located in the anterior part of the frontal lobes of the brain, lying in front of the motor and premotor areas. Cytoarchitectonically, it is defined by the presence of an internal granular layer IV (in contrast to the agranular premotor cortex). Divided into the lateral, orbitofrontal and medial prefrontal areas, this brain region has been implicated in planning complex cognitive behaviors, personality expression and moderating correct social behavior. The basic activity of this brain region is considered to be the orchestration of thoughts and actions in accordance with internal goals. The most typical neurologic term for functions carried out by the pre-frontal cortex area is Executive Function. Executive Function relates to abilities to differentiate between conflicting thoughts, determine good and bad, better and best, same and different, future consequences of current activities, working toward a defined goal, prediction of outcomes, expectation based on actions, and social "control" (the ability to suppress urges that, if not suppressed, could lead to socially unacceptable or illegal outcomes). Many authors have indicated an integral link between a person's personality and the functions of the prefrontal cortex.

Hippocampus

The hippocampus is the principle structure for forming long-term memories, including emotional memory. The crescent shaped hippocampus is found deep in the temporal lobe, in the front of the limbic system. The hippocampus forms and stores your memories and is involved in learning. The hippocampus appears to be one of the most important parts of the brain. People with Alzheimer's Disease loose the functioning of their hippocampus.

The Hippocampus is a part of the brain located inside the temporal lobe (humans have two hippocampi, one in each side of the brain). It forms a part of the limbic system and plays a part in memory and navigation. The name derives from its curved shape in coronal sections of the brain, which to some resembles a seahorse (Greek: hippokampos). In Alzheimer's disease, the hippocampus becomes one of the first regions of the brain to suffer damage; memory problems and disorientation appear amongst the first symptoms. Damage to the hippocampus can also result from oxygen starvation (anoxia) and encephalitis. Psychologists and neuroscientists dispute the precise role of the hippocampus, but, in general, agree that it has an essential role in the formation of new memories about experienced events (episodic or autobiographical memory). Some researchers prefer to consider the hippocampus as part of a larger medial temporal lobe memory system responsible for general declarative memory (such as, for example, memories that can be explicitly verbalized which would include, for example, memory for facts in addition to episodic memory).

Some evidence supports the idea that, although these forms of memory often last a lifetime, the hippocampus ceases to play a crucial role in the retention of the memory after a period of consolidation. Damage to the hippocampus usually results in profound difficulties in forming new memories (anterograde amnesia), and normally also affects access to memories prior to the damage (retrograde amnesia). Although the retrograde effect normally extends some years prior to the brain damage, in some cases older memories remain. This sparing of older memories leads to the idea that consolidation over time involves the transfer of memories out of the hippocampus to other parts of the brain. However, experimentation has difficulties in testing the sparing of older memories; and, in some cases of retrograde amnesia, the sparing appears to affect memories formed decades before the damage to the hippocampus occurred, so its role in maintaining these older memories remains controversial. Damage to the hippocampus does not affect some aspects of memory, such as the ability to learn new skills (playing a musical instrument, for example), suggesting that such abilities depend on a different type of memory (procedural memory) and different brain regions.

Role in Spatial Memory and Navigation

Some evidence implicates the hippocampus in storing and processing spatial information. Studies in rats have shown that neurons in the hippocampus have spatial firing fields. These cells are called place cells. Some cells fire when the animal finds itself in a particular location, regardless of the direction of travel, while most are at least partially sensitive to head direction and direction of travel. In rats, some cells, termed splitter cells, may alter their firing depending on the animal's recent past (retrospective) or expected future (prospective). Different cells fire at different locations, so that, by looking at the firing of the cells alone, it becomes possible to tell where the animal is. Place cells have now been seen in humans involved in finding their way around in a virtual reality town. The findings resulted from research with individuals that had electrodes implanted in their brains as a diagnostic part of surgical treatment for serious epilepsy.

The discovery of place cells led to the idea that the hippocampus might act as a cognitive map of a neural representation of the layout of the environment. Recent evidence has cast doubt on this perspective, indicating that the hippocampus might be crucial for more fundamental processes within navigation. Regardless, studies with animals have shown that an intact hippocampus is required for simple spatial memory tasks (for instance, finding the way back to a hidden goal). Without a fully-functional hippocampus, humans may not successfully remember the places they have been to and how to get where they are going. Researchers believe that the hippocampus plays a particularly important role in finding shortcuts and new routes between familiar places. Some people exhibit more skill at this sort of navigation than do others, and brain imaging shows that these individuals have more active hippocampi when navigating.

Hypothalamus

Whilst the Hippocampus is the main input; the Hypothalamus is the main output. In this regard, the hypothalamus makes no decisions about emotion. It has no role in analyzing external cues. It simply carries out the physiology. Once the amygdala and prefrontal cortex have analyzed the situation/stimulus, the amygdala projects to the appropriate hypothalamic nuclei and brainstem autonomic nuclei, resulting in the physiological responses. The hypothalamus is part of the limbic system. It is located in the internal portion of the brain under the thalamus. The hypothalamus controls the body's temperature, emotions, hunger, thirst, appetite, digestion and sleep. The hypothalamus is composed of several different areas and is located at the base of the brain. It is only the size of a pea (about $\frac{1}{300}$ of the total brain weight), but is responsible for some very important behaviours such as but not limited to controlling visceral functions, body temperature and behavioural responses such as feeding, drinking, sexual response, aggression and pleasure. The hypothalamic pituitary adrenal axis is also upset in depression.

As discussed above, exposure to stress and the stress hormone corticosterone has been shown to decrease the expression of growth factor modulators, such as BDNF, in rats, and leads to an eventual atrophy of the hippocampus if exposure is persistent. Similar atrophy has been shown to take place in humans suffering from chronic depression. In addition, rats bred to be heterozygous for BDNF, therefore reducing its expression, have been observed to exhibit similar hippocampal atrophy, suggesting that an etiological link between the development of depressive illness and regulation of BDNF exists. On the other hand, the excitatory neurotransmitter glutamate, voluntary exercise, caloric restriction, intellectual stimulation, and various treatments for depression (such as antidepressants and electroconvulsive therapy) strongly increase expression of BDNF in the brain, and have been shown to protect against this atrophy.

"Selective Sigma 1 Receptor Agonist(s)"

As used herein, the term "Selective Sigma 1 receptor agonist(s)" means an agonist which preferentially binds to or activates a Sigma 1 receptor as compared with a Sigma 2 receptor.

As used herein, the term "Sigma 1 receptor" refers to a transmembrane protein expressed in many different tissue types. It is particularly concentrated in certain regions of the central nervous system. The Sigma-1 receptor is a 26 kDa protein, and the gene encoding the receptor has been cloned. Hydropathy analysis suggested that the sigma-1 receptor has two transmembrane segments. Further, the sigma-1 receptors share no homology with any other known mammalian proteins. Subcellular distribution analyses indicate that the Sigma 1 receptor is present in different brain structures, such as the cortex, the hippocampus and olfactory bulb and it is localized on cell membranes, endoplasmic reticulum membranes, and mitochondrial membranes. (Alonso et al., Neuroscience, 97: 155-170 (2000). The significance of the different sub-cellular localizations of the sigma 1 receptor remains unknown.

Agonists/Antagonists

Agonists and antagonists are agents which recognize and bind to receptors, affecting (either initiating or blocking) biochemical/physiological sequences, by a process known as transduction.

The term "agonist" as used herein refers to a compound or a composition that can stimulate or positively influence the intracellular signaling pathways of a receptor, or can supplement, augment or act synergistically with the activity of any other compound or composition thereon. Thus, as used herein, the term "agonist" refers to any agent or entity capable of activating or enhancing the expression and/or functional activity of a target receptor, protein, polypeptide portion thereof, or polynucleotide. Thus, an agonist may operate to promote gene expression, for example promote gene transcription (by, for example, binding to a genetic sequence such as a transcriptional elements), translation, post-transcriptional or post-translational processing or otherwise activate the activity of the target receptor, protein, polypeptide or polynucleotide in any way, via either direct and/or indirect action and/or competitively and/or non-competitively (such as, for example, working at a site which is distal to receptor site itself). An agonist may for example be a nucleic acid, peptide, or any other suitable chemical compound or molecule or any combination of these. Additionally, it will be understood that indirectly promoting the activity of a target receptor, protein, polypeptide of polynucleotide, an agonist may affect the activity of the cellular molecules which may in turn act as regulators or the target receptor, protein, polypeptide or polynucleotide itself. Similarly, an agonist may affect the activity of molecules which are themselves subject to the regulation or modulation by the target receptor, protein, polypeptide of polynucleotide. An agonist also refers to any agent that is capable of causing an increase in the activity of a gene and/or gene product in a cell, whether it was present in the cell or absent in the cell prior to adding such an agent.

The term "activating" or "activates" or are used interchangeably herein, refers to the general increase in activity of a target receptor, protein, polypeptide portion thereof, or polynucleotide or a metabolic regulator of the present invention. Activation does not necessarily mean complete activation of expression and/or activity of the metabolic regulator, rather, a general or total increase in the expression or activity of the target receptor, protein, polypeptide or polynucleotide that is activated to an extent, and/or for a time, sufficient to produce the desired effect.

In one preferred embodiment, the agent increases the expression and/or functional activity of the expression product by at least 10%, 20%, 30%, 40%, 50%, 60%, 70%, 75%, 80%, 85%, 90%, 95% relative to the expression and/or functional activity in the absence of the agent.

The term "antagonist" as used herein refers to a compound or composition that can inhibit, suppress, block or negatively influence the intracellular signaling pathways of a target receptor, protein, polypeptide portion thereof or polynucleotide or a metabolic regulator of the present invention. Thus, as used herein, the term "antagonist" or "inhibitor" are used interchangeably herein, refers to any agent or entity capable of inhibiting or suppressing the expression or activity of a target receptor, protein, polypeptide portion thereof, or polynucleotide. Thus, the antagonist may operate to prevent transcription, translation, post-transcriptional or post-translational processing or otherwise inhibit the activity of the target receptor, protein, polypeptide or polynucleotide in any way, via either direct and/or indirect action and/or competitively and/or non-competitively (such as, for example, working at a site which is distal to receptor rather than at a receptor site itself). The antagonist may, for example, be a nucleic acid, peptide, or any other suitable chemical compound or molecule or any combination of these. Additionally, it will be understood that in indirectly impairing the activity of a target receptor, protein, polypeptide or polynucleotide, the antagonist may affect the activity of the cellular molecules which may in turn act as regulators or the target receptor, protein, polypeptide or the polynucleotide itself. Similarly, the antagonist may affect the activity of molecules which are themselves subject to the regulation or modulation by the target receptor, protein, polypeptide or polynucleotide.

The term "inhibiting" as used herein does not necessarily mean complete inhibition of expression and/or functional activity. Rather, expression and/or functional activity of the protein, polypeptide or polynucleotide or nucleic acid is inhibited to an extent, and/or for a time, sufficient to produce the desired effect.

In one preferred embodiment, the agent reduces the expression and/or functional activity of the expression product by at least 10%, 20%, 30%, 40%, 50%, 60%, 70%, 75%, 80%, 85%, 90%, 95% relative to the expression and/or functional activity in the absence of the agent.

Growth Factor Modulating Selective Sigma 1 or Dopamine D3 Receptor Agonist or a 5HT$_{2c}$ Receptor Ligand Typically, a growth factor modulating selective Sigma 1 or Dopamine D3 receptor agonist or a 5HT$_{2c}$ receptor ligand, such as Captodiamine, or pharmaceutically acceptable salts thereof or mixtures thereof will be prepared by chemical synthesis techniques. The growth factor modulating selective Sigma 1 or Dopamine D3 receptor agonist or a 5HT$_{2c}$ receptor ligand, such as Captodiamine, or pharmaceutically acceptable salts thereof or mixtures thereof or variants, homologues, derivatives, fragments, mimetics or analogs thereof may be produced using chemical methods to synthesize the agonist or ligand in whole or in part. Combinatorial libraries may be used to identify mimetics capable of acting in the same or a similar manner to the growth factor modulating selective Sigma 1 or Dopamine D3 receptor agonist or a 5HT$_{2c}$ receptor ligand, such as Captodiamine, or pharmaceutically acceptable salts thereof or mixtures thereof.

As used herein, the term "mimetic" relates to any chemical which includes, but is not limited to, a peptide, polypeptide, antibody or other organic chemical which has the same qualitative functional activity or effect as a growth factor modulating selective Sigma 1 or Dopamine D3 receptor agonist or a 5HT$_{2c}$ receptor ligand, or a compound of Formula I such as Captodiamine, or pharmaceutically acceptable salts thereof or mixtures thereof. That is, a mimetic may be a functional equivalent of a known compound, such as a growth factor modulating selective Sigma 1 or Dopamine D3 receptor agonist or a 5HT$_{2c}$ receptor ligand, such as Captodiamine, which is capable of inducing the improved pharmacological functional activity and/or effect and/or behavioural response in a given subject.

Formula 1 has the structure:

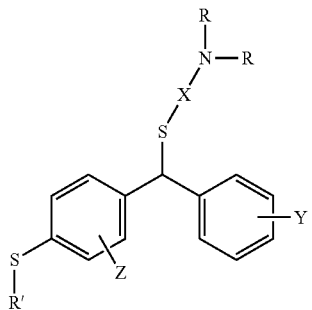

FORMULA I wherein
X is an ethylene, propylene, butylene or pentylene group;
R is $C_{1-9}$ alkyl, preferably $C_{1-5}$ alkyl;
R' is $C_{1-9}$ alkyl, alkenyl or alkynyl;
Y is hydrogen, halide such as chloro, fluoro, iodo or bromo, hydroxy$C_{1-4}$alkyl, amino, $C_{1-4}$alkylamino, acetylamino or thio; and
Z is hydrogen, halide such as chloro, fluoro, iodo or bromo, hydroxy$C_{1-4}$alkyl, amino, $C_{1-4}$alkylamino, acetylamino or thio, or a pharmaceutically acceptable salt thereof.

The term "derivative" or "derivatised" as used herein includes one or more chemical modifications of a growth factor modulating selective Sigma 1 or Dopamine D3 receptor agonist or a 5HT$_{2c}$ receptor ligand, or a compounds disclosed in Formulae I, such as Captodiamine or pharmaceutically acceptable salts thereof or mixtures thereof. That is, a "derivative" may be a functional equivalent of a known growth factor modulating selective Sigma 1 or Dopamine D3 receptor agonist or a 5HT$_{2c}$ receptor ligand, such as Captodiamine, which is capable of inducing the improved pharmacological functional activity and/or behavioural response in a given subject. Illustrative of such chemical modifications would be replacement of hydrogen by a halo group, an alkyl group, an acyl group or an amino group.

The chemical modification of a compound of Formula I or growth factor modulating selective Sigma 1 or Dopamine D3 receptor agonist or a 5HT$_{2c}$ receptor ligand, such as Captodiamine, or pharmaceutically acceptable salts thereof or mixtures thereof may either enhance or reduce hydrogen bonding interaction, charge interaction, hydrophobic interaction, Van Der Waals interaction or dipole interaction from the growth factor modulating selective Sigma 1 or Dopamine D3 receptor agonist or a 5HT$_{2c}$ receptor ligand, such as Captodiamine, and its target.

In one embodiment, the compound of Formula I or growth factor modulating selective Sigma 1 or Dopamine D3 receptor agonist or a 5HT$_{2c}$ receptor ligand, such as Captodiamine, or pharmaceutically acceptable salts thereof or mixtures thereof may act as a model (for example, a template) for the development of other derivative compounds which are a functional equivalent of a known compound of Formula I or growth factor modulating selective Sigma 1 or Dopamine D3 receptor agonist or a 5HT$_{2c}$ receptor ligand, such as Captodiamine, which is capable of inducing the improved pharmacological functional activity and/or effect and/or behavioural response in a given subject.

Agents having inhibitory, activating, or modulating activity can be identified using in vitro and in vivo assays for changes in growth factor modulating selective Sigma 1 or Dopamine D3, or 5HT$_{2c}$ receptor functional activity and/or expression. Such agents include but are not limited to ligands, agonists, antagonists, and their homologs and mimetics. The modulatory agents may be naturally occurring molecules such as peptides and proteins, for example antibodies, or they may be synthetic molecules. By way of example, the expression level and/or functional activity of a protein of the present invention may be reduced through use of anti-antigen-binding molecules (such as, for example, neutralising antibodies). The present invention also contemplates the use of antagonistic antigen-binding molecules with varying blocking capacities.

Preferred growth factor modulating selective Sigma 1 or Dopamine D3 receptor agonist or a 5HT$_{2c}$ receptor ligands for use according to the present invention include but are not limited to diphenhydramine derivative compounds and/or compounds represented by Formula I and variants, derivatives and mimetics thereof.

The compounds of Formula I or Formula II may be racemic compounds of Formula I or II and/or optically active isomers thereof. In this regard, some of the compounds of Formula I and the compound of Formula II can have asymmetric carbon atoms, and therefore, can exist either as racemic mixtures or as individual optical isomers (enantiomers). Compounds described herein that contain a chiral center include all possible stereoisomers of the compound, including compositions comprising the racemic mixture of the two enantiomers, as well as compositions comprising each enantiomer individually, substantially free of the other enantiomer. Thus, for example, contemplated herein is a composition comprising the S enantiomer of a compound substantially free of the R enantiomer, or the R enantiomer substantially free of the S enantiomer. If the named compound comprises more than one chiral center, the scope of the present disclosure also includes compositions comprising mixtures of varying proportions between the diastereomers, as well as compositions comprising one or more diastereomers substantially free of one or more of the other diastereomers. By "substantially free" it is meant that the composition comprises less than 25%, 15%, 10%, 8%, 5%, 3%, or less than 1% of the minor enantiomer or diastereomer(s). Methods for synthesizing, isolating, preparing, and administering various stereoisomers are known in the art. Separation of diastereoisomers or cis and trans isomers may be achieved by conventional techniques, such as, for example, by fractional crystallisation, chromatography or High Performance Liquid Chromatography (HPLC) of a stereoisomeric mixture of the agent or a suitable salt or derivative thereof. An individual enantiomer of a compound of Formulae I, such as Captodiamine, may also be prepared from a corresponding optically pure intermediate or by resolution, such as by HPLC of the corresponding racemate using a suitable chiral support or by fractional crystallisation of the diastereoisomeric salts formed by reaction of the corresponding racemate with a suitable optically active acid or base, as appropriate. In the context of the present invention, when reference to organic residues or moieties having a specific number of carbons is made, unless clearly stated otherwise, it intends all geometric and other isomers thereof. For example, "butyl" includes n-butyl, sec-butyl, isobutyl and t-butyl; "propyl" includes n-propyl and isopropyl.

It will be appreciated by those skilled in the art that a compound of Formula I or II of the present invention may be derived from a prodrug. Examples of prodrugs include entities that have certain protected group(s) and which may not possess pharmacological activity as such, but may, in certain instances, be administered (such as orally or parenterally) and thereafter metabolised in the body to form the agent of the present invention which are pharmacologically active.

It will be further appreciated that certain moieties known as "pro-moieties", for example as described in "Design of Prodrugs" by H. Bundgaard, Elsevier, 1985 (the disclosure of which is hereby incorporated by reference), may be placed on appropriate functionalities of the compound of the present invention. Such prodrugs are also included within the scope of the invention.

Typically the compound of Formula I, such as Captodiamine, or pharmaceutically acceptable salts thereof or mixtures thereof will be prepared by chemical synthesis techniques. The compound of Formula I, such as Captodiamine, or pharmaceutically acceptable salts thereof or mixtures thereof or variants, homologues, derivatives, fragments or mimetics thereof may be produced using chemical methods to synthesize the agent in whole or in part. Combinatorial libraries may be used to identify mimetics capable of acting in the same or a similar manner to the compound of Formula I, such as Captodiamine, or pharmaceutically acceptable salts thereof or mixtures thereof.

As used herein, the term "pharmaceutically acceptable salts" includes acid addition salts or addition salts of free bases. The term "pharmaceutically acceptable salts" of a growth factor modulating selective Sigma 1 or Dopamine D3 receptor agonist or a $5HT_{2c}$ receptor ligand, such as Captodiamine, is also meant to include within its scope all the possible isomers and their mixtures, and any pharmaceutically acceptable metabolite, bioprecursor and/or pro-drug. As used herein, the term "pro-drug" means a compound which has a structural formula different from a growth factor modulating selective Sigma 1 or Dopamine D3 receptor agonist or a $5HT_{2c}$ receptor ligand, such as Captodiamine, and yet is directly or indirectly converted in vivo into a growth factor modulating selective Sigma 1 or Dopamine D3 receptor agonist or a $5HT_{2c}$ receptor ligand, such as Captodiamine, upon administration to a subject, such as a mammal, particularly a human being.

As used herein, the term "subject" refers to vertebrates, particularly members of the mammalian species. The term includes but is not limited to domestic animals, sports animals, primates and humans. Examples of subjects include but are not limited to a cat, dog, horse, cow, pig, mouse, rat, or primate, including human. In one embodiment the subject is a human, for example a patient having or at risk of a condition with symptoms of anxiety and/or depression associated with an "affective" disorder; and/or (b) symptoms associated with a cognitive impairment disorder in a subject in need of same.

Affective Disorder

The invention relates to the use of growth factor modulating selective Sigma 1 or Dopamine D3 receptor agonist or a $5HT_{2c}$ receptor ligand to treat emotional, behavioural, neurological, and mental disorders, collectively referred to herein as "affective" disorders, all of which include anxiety and/or depression as a symptom. In this regard, anxiety may be present with or without other disorders such as depression. Mixed anxiety/depressive disorders include anxiety in the presence of depressive symptoms or exclude anxiety in the absence of depressive symptoms. The compounds and/or the compositions of the present invention are therefore useful in the treatment of symptoms of anxiety with or without the accompanying symptoms of depression. The present invention also relates to the use of growth factor modulating selective Sigma 1 or Dopamine D3 receptor agonist or a $5HT_{2c}$ receptor ligand as cognitive enhancers, for example, to enhance learning and memory. These affective disorders may also include symptoms of anxiety and decreased cognitive function (for example, decreased learning and memory). By way of example, an affective disorder may include a disorder with one or more attendant symptoms of anxiety, impaired learning, and impaired memory, and impaired cognition in a subject in need of such treatment. Other symptoms of the "affective" disorder can include but are not limited to anxiety, fear, impaired learning, impaired memory, apathy, delusions, anxiety, and autonomic changes, avoidance, increased arousal, depression, elevated mood, irritable mood, hallucinations, disorganized speech, and grossly disorganized behavior.

Depressive Disorders

As used herein, the term "depression" includes depressive disorders, for example, single episodic or recurrent major depressive disorders (MDD), and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias, seasonal affective disorder, or bipolar disorders or manic depression, for example, bipolar I disorder, bipolar II disorder and cyclothymic disorder.

Other mood disorders encompassed within the term "depression" include dysthymic disorder with early or late onset and with or without atypical features; dementia of the Alzheimer's type, with early or late onset, with depressed mood; vascular dementia with depressed mood, disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood.

"Major depressive disorder", or "MDD", as mentioned above is defined according to the criteria in DSM-IV and is incorporated herein by reference. The DSM-IV criteria may be used to diagnose patients as suffering from depression. The term also contemplates all diseases and conditions which are associated with MDD, including those classified in the IDC-10 (World Health Organization) and DSM-IV rating scales.

The antidepressant activity of the growth factor modulating selective Sigma 1 or Dopamine D3 receptor agonist or a $5HT_{2c}$ receptor ligand of the present invention may be determined by standard pharmacological tests including but not limited to the behavioral despair paradigm described by R. D. Porsolt in Arch. Int. Pharmacodun. 227, 327 (1997). The procedure comprises administering the agent of interest to a mouse (Male CD (Charles River), weighing 20-25 g) which is then placed in a plexiglass cylinder (25 cm high and 10 cm in diameter) containing 6 cm water of 25° C. one hour after injection. The mouse is left in the cylinder for 6 minutes and after the first two minutes observed for duration of mobility. Other tests to measure anti-depressant activity include but are not limited to the Force Swim Test (described below) where the time spent immobile is a measure of despair.

Anxiety Disorders

As used herein, the term "anxiety" disorders includes but is not limited to a generalized anxiety disorder (GAD), social anxiety disorder (SAD; alternatively knows as social phobia), panic disorder (with or without agoraphobia), posttraumatic stress disorder (PTSD), obsessive-compulsive disorder (OCD), separation anxiety disorder, mood disorders (such as, for example, depressive disorder, bipolar disorder) psychotic disorders (such as, for example, schizophrenia, schizoaffective disorder, delusional disorder), substance-related disorders (such as, for example, substance abuse, substance-induced disorder, substance withdrawal), cognitive disorders (such as, for example, dementia, delirium, Alzheimer's type dementia), affective disorder associated with neurological medical disorders (such as, for example, a seizure disorder, epilepsy), and affective disorders of childhood (such as, for example, attention disorder, attention deficit hyperactivity disorder, learning disorder, separation anxiety).

As used herein, the term "anxiety" includes anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalized anxiety disorders.

"Generalized anxiety" is typically defined as an extended period (such as, for example, at least six months) of excessive anxiety or worry with symptoms on most days of that period. The anxiety and worry is difficult to control and may be accompanied by restlessness, being easily fatigued, difficulty concentrating, irritability, muscle tension, and disturbed sleep.

"Panic disorder" is defined as the presence of recurrent panic attacks followed by at least one month of persistent concern about having another panic attack. A "panic attack" is a discrete period in which there is a sudden onset of intense apprehension, fearfulness or terror. During a panic attack, the individual may experience a variety of symptoms including palpitations, sweating, trembling, shortness of breath, chest pain, nausea and dizziness. Panic disorder may occur with or without agoraphobia.

"Phobias" includes agoraphobia, specific phobias and social phobias. "Agoraphobia" is characterized by an anxiety about being in places or situations from which escape might be difficult or embarrassing or in which help may not be available in the event of a panic attack.

Agoraphobia may occur without history of a panic attack. A "specific phobia" is characterized by clinically significant anxiety provoked by feared object or situation. Specific phobias include the following subtypes: animal type, cued by animals or insects; natural environment type, cued by objects in the natural environment, for example storms, heights or water; blood-injection-injury type, cued by the sight of blood or an injury or by seeing or receiving an injection or other invasive medical procedure; situational type, cued by a specific situation such as public transportation, tunnels, bridges, elevators, flying, driving or enclosed spaces; and other type where fear is cued by other stimuli. Specific phobias may also be referred to as simple phobias. "Asocial phobia" is characterized by clinically significant anxiety provoked by exposure to certain types of social or performance circumstances. Social phobia may also be referred to as social anxiety disorder.

Other anxiety disorders encompassed within the term "anxiety" include anxiety disorders induced by alcohol, amphetamines, caffeine, cannabis, cocaine, hallucinogens, inhalants, phencychdine, sedatives, hypnotics, anxiolytics and other substances, and adjustment disorders with anxiety or with mixed anxiety and depression.

The anxiolytic activity of the growth factor modulating selective Sigma 1 or Dopamine D3 receptor agonist or a $5HT_{2c}$ receptor ligand of the present invention may be determined by standard pharmacological tests including but not limited to the Open-Field Analysis test and the Elevated X Maze (XM) test which are described in more detail below. Briefly, the Open Field Analysis test measures the time spent in the centre of the open field as an indicator of potential anxiolytic-like behaviour. The Elevated X-Maze test also assesses potential anxiolytic activity by determining the amount of time spent in the unprotected/exposed elevated arm of the maze which is inversely related to the level of stress/anxiety felt by the animal.

Animal tests for anxiolytic activity are known in the art. For example, one test involves pairing a reward for which the animal must perform some behaviour, such as lever pressing, with an aversive stimulus, such as mild electric shock. Agents that increase the rate of responses punished with the shock tend to be anxiolytic in humans (see basic Neurochemistry, 6th ed. Siegel et al. editors). Other animal tests for anxiolytic activity include but are not limited to the Open Field Analysis Test and the Elevated X-Maze (XM) test as discussed in more detail below. Another indicator of anxiolytic activity is a compound's binding affinity for the GABA-A receptor.

Cognitive Function

In one embodiment the subject being treated is a mammal, including humans, in need of alleviation, or inhibition of symptoms of cognitive disorders.

As used herein, the term "cognitive" includes but is not limited to cognitive deficits such as deficits in different cognitive domains such as memory, visuospatial processing, attention, concept formation, and executive functions. Specific examples of cognitive disorders include but are not limited to autism, dyslexia, attention deficit hyperactivity disorder, anxiety, schizophrenia, obsessive compulsive disorders, psychosis, bipolar disorders, Tourette's syndrome, Mild Cognitive Impairment (MCI) and disorders of learning in children, adolescents and adults, Age Associated Memory Impairment, Age Associated Cognitive Decline, Down's Syndrome, HIV and vascular diseases. A range of cognitive impairment disorders are disclosed and described in U.S. Pat. No. 4,895,841, WO2001/066114 and EP1311272B1, all of which are incorporated by reference in their entirety.

The term "cognitive function" refers to mental processes of an animal or human subject relating to information gathering and/or processing; the understanding, reasoning, and/or application of information and/or ideas; the abstraction or specification of ideas and/or information; acts of creativity, problem-solving, and possibly intuition; and mental processes such as learning, perception, and/or awareness of ideas and/or information. The mental processes are distinct from those of beliefs, desires, and the like. In some embodiments, cognitive function may be assessed, and thus optionally defined, via one or more tests or assays for cognitive function.

Non-limiting examples of a test or assay for cognitive function include but are not limited to CANTAB (see for example Fray et al. "CANTAB battery: proposed utility in neurotoxicology." Neurotoxicol Teratol. 1996; 18(4):499-504), Stroop Test, Trail Making, Wechsler Digit Span, or the CogState computerized cognitive test (see also Dehaene et al. "Reward-dependent learning in neuronal networks for planning and decision making." Prog Brain Res. 2000; 126:217-29; Iverson et al. "Interpreting change on the WAIS-III/WMS-III in clinical samples." Arch Clin Neuropsvchol. 2001; 16(2): 183-91; and Weaver et al. "Mild memory impairment in healthy older adults is distinct from normal aging." Brain Cogn. 2006; 60(2): 146-55). Other tests for cognitive function include the Novel Object Recognition (NOR) test which evaluates the role of experimental manipulations on cognition and the Water Maze Spatial Learning test which is a measure of pre-cognitive action by evaluating information acquisition and consolidation by the subject animal under test. Human cognitive tests include but are not limited to Card Sort Tasks, Associative Memory Tasks, Context Memory Tasks and The Stroop Task. These tests are discussed in more detail below.

In one embodiment of the invention, the subject has normal cognitive function which is improved or enhanced. As used herein, improving or enhancing cognitive function means an improvement or enhancement in a mental function, such as learning or memory. It also includes "promoting" cognitive function (affecting impaired cognitive function in the subject so that it more closely resembles the function of an aged-matched normal, unimpaired subject, including affecting states in which cognitive function is reduced compared to a normal subject) and "preserving" cognitive function (affecting normal or impaired cognitive function such that it does not decline or does not fall below that observed in the subject upon first presentation or diagnosis, such as, for example, to the extent of expected decline in the absence of treatment).

In another embodiment the subject is a mammal which exhibits cognitive impairment associated with aging. In one embodiment the subject is a human with cognitive impairment associated with a disease or disorder. In a further embodiment the subject is a human exhibiting cognitive function impairment associated with disorders with symptoms of anxiety and/or depression associated with an "affective" disorder; and/or symptoms associated with a cognitive impairment disorder which are associated with "affective" disorders including but not limited to autism, dyslexia, attention deficit hyperactivity disorder, schizophrenia, obsessive compulsive disorders, psychosis, bipolar disorders, depression, Tourette's syndrome and disorders of learning in children, adolescents and adults, Age Associated Memory Impairment, Age Associated Cognitive Decline, Parkinson's Disease, Down's Syndrome, traumatic brain injury Huntington's Disease, Progressive Supranuclear Palsy (PSP), HIV, stroke, vascular diseases, Pick's or Creutzfeldt-Jacob diseases, multiple sclerosis (MS), other white matter disorders and drug-induced cognitive worsening. In another embodiment, the impairment of cognitive function is caused by, or attributed to, Alzheimer's disease. In yet another embodiment, the impairment of cognitive function is caused by, or attributed to, mild cognitive impairment (MCI).

For purposes of this invention, beneficial or desired clinical results include, but are not limited to an alleviation and/or diminishment and/or preventing a worsening of and/or a modulation of the symptoms of anxiety and/or depression associated with an "affective" disorder; and/or symptoms associated with a cognitive impairment disorder in a subject in need of same.

Preferably, treatment with a growth factor modulating selective Sigma 1 or Dopamine D3 receptor agonist or a $5HT_{2c}$ receptor ligand, such as Captodiamine, or a pharmaceutically acceptable salt thereof or mixtures thereof as disclosed is accompanied by no or fewer side effects than those that are commonly associated with administration of antipsychotic drugs, such as extrapyramidal side effects (such as rigidity, tremor), bradykinesia (slow movement), and bradyphrenia (slow thought), acute dystonia (such as involuntary muscle contraction), acute dyskinesia, and tardive dyskinesia (such as involuntary movements).

Combination Therapy

The growth factor modulating selective Sigma 1 or Dopamine D3 receptor agonist or a $5HT_{2c}$ receptor ligands of the present invention are also useful in association with or in combination with other agents and/or treatments that are useful in, for example, improving cognitive function in pathological conditions with symptoms associated with symptoms of anxiety and/or depression associated with an "affective" disorder; and/or symptoms associated with a cognitive impairment disorder in a subject in need of same.

The compositions of the present invention are especially useful for the treatment of symptoms of anxiety and/or depression associated with an "affective" disorder; and/or symptoms associated with a cognitive impairment disorder in a subject in need of same where the use of an antidepressant and/or an anxiolytic agent and/or a cognitive enhancing agent respectively, is generally prescribed. By the use of a combination of a growth factor modulating selective Sigma 1 or Dopamine D3 receptor agonist or a $5HT_{2c}$ receptor ligand, such as Captodiamine, or a pharmaceutically acceptable salt thereof or mixtures thereof and one or more antidepressant and/or anxiolytic and/or cognitive enhancing agents in accordance with the present invention, it is possible to treat symptoms associated with depression and/or anxiety and/or cognitive impairment in subjects/patients for whom conventional antidepressant and/or antianxiety and/or cognitive enhancing therapy might not be wholly successful or where dependence upon the antidepressant and/or antianxiety and/or cognitive enhancing therapy is prevalent.

The combination therapy may be of one of the above antidepressant and/or anxiolytic and/or cognitive enhancing agents with a growth factor modulating selective Sigma 1 or Dopamine D3 receptor agonist or a $5HT_{2c}$ receptor ligand, such as Captodiamine, or a pharmaceutically acceptable salt thereof or mixtures thereof as described herein to improve the condition of the subject or patient. Non-limiting examples of combination therapy include the use of lower dosages of the above additional agents, or combinations thereof, which reduce side effects of the agent or combination when used alone. For example, an anti-depressant agent like fluoxetine or paroxetine or sertraline may be administered at a reduced or limited dose, optionally also reduced in frequency of administration, in combination with a cognitive enhancing agent, which are used in combination with a growth factor modulating selective Sigma 1 or Dopamine D3 receptor agonist or a 5HT$_{2c}$ receptor ligand, such as Captodiamine, or a pharmaceutically acceptable salt thereof or mixtures thereof.

In light of the positive recitation (discussed both above and below) of combinations with alternative agents to treat conditions disclosed herein, the disclosure includes embodiments with the explicit exclusion of one or more of the alternative agents. As would be recognized by the skilled person, a description of the whole of a plurality of alternative agents necessarily includes and describes subsets of the possible alternatives, or the part remaining with the exclusion of one or more of the alternatives.

The present invention contemplates the use of a growth factor modulating selective Sigma 1 or Dopamine D3 receptor agonist or a 5HT$_{2c}$ receptor ligand, such as Captodiamine, or a pharmaceutically acceptable salt thereof or mixtures thereof in combination(s) with other agents to treat subjects suffering from symptoms of anxiety and/or depression associated with an "affective" disorder; and/or symptoms associated with a cognitive impairment disorder in a subject in need of same as described herein. By way of example, other therapeutics that may be administered with a growth factor modulating selective Sigma 1 or Dopamine D3 receptor agonist or a 5HT$_{2c}$ receptor ligand, such as Captodiamine, or a pharmaceutically acceptable salt thereof or mixtures include, but are not limited to: (i) an anti-depressant agent; (ii) an anxiolytic agent; and (iii) a cognitive enhancing agent. The growth factor modulating selective Sigma 1 or Dopamine D3 receptor agonist or a 5HT$_{2c}$ receptor ligand such as Captodiamine or a pharmaceutically acceptable salt thereof or mixtures thereof may also be used in combination with a behavioural therapy, voluntary exercise, caloric restriction, intellectual stimulation, electroconvulsive therapy, and excitatory neurotransmitter glutamate, and the like, any or all of which may act in a receptor specific and/or factor specific and/or region specific manner.

Behavioural Therapy

Examples of Behavioural therapy include but are not limited to Cognitive Behavioural Therapy and Dialectical Behavioural Therapy. Cognitive Behavioural Therapy (CBT) is a psychotherapy based on modifying cognitions, assumptions, beliefs and behaviours, with the aim of influencing disturbed emotions. The general approach, developed out of behaviour modification, Cognitive Therapy and Rational Emotive Behaviour Therapy, has become widely used to treat various kinds of neuroses and psychopathology, including mood disorders and anxiety disorders. The particular therapeutic techniques vary according to the particular kind of client or issue, but commonly include keeping a diary of significant events and associated feelings, thoughts and behaviours; questioning and testing cognitions, assumptions, evaluations and beliefs that might be unhelpful and unrealistic; gradually facing activities which may have been avoided; and trying out new ways of behaving and reacting. Relaxation and distraction techniques are also commonly included. CBT is widely accepted as an evidence- and empiricism-based, cost-effective psychotherapy for many disorders and psychological problems. It is sometimes used with groups of people as well as individuals, and the techniques are also commonly adapted for self-help manuals and, increasingly, for self-help software packages. The cognitive model especially emphasized in Aaron Beck's cognitive therapy says that a person's core beliefs (often formed in childhood) contribute to "automatic thoughts" that pop up in everyday life in response to situations. Cognitive Therapy practitioners hold that clinical depression is typically associated with negatively biased thinking and irrational thoughts.

Dialectical Behavioural Therapy (DBT) is based on a biosocial theory of borderline personality disorder. Linehan hypothesises that the disorder is a consequence of an emotionally vulnerable individual growing up within a particular set of environmental circumstances which she refers to as the 'Invalidating Environment'. An 'emotionally vulnerable' person in this sense is someone whose autonomic nervous system reacts excessively to relatively low levels of stress and takes longer than normal to return to baseline once the stress is removed. It is proposed that this is the consequence of a biological diathesis. The term 'Invalidating Environment' refers essentially to a situation in which the personal experiences and responses of the growing child are disqualified or "invalidated" by the significant others in her life. The child's personal communications are not accepted as an accurate indication of her true feelings and it is implied that, if they were accurate, then such feelings would not be a valid response to circumstances. Furthermore, an Invalidating Environment is characterised by a tendency to place a high value on self-control and self-reliance. Possible difficulties in these areas are not acknowledged and it is implied that problem solving should be easy given proper motivation. Any failure on the part of the child to perform to the expected standard is therefore ascribed to lack of motivation or some other negative characteristic of her character. (The feminine pronoun has been used throughout when referring to the patient since the majority of BPD patients are female and Linehan's work has focused on this subgroup).

Anti-depressant Agents

Suitable classes of antidepressant agents that may be used in the present invention include norepinephrine reuptake inhibitors, selective serotonin reuptake inhibitors (SSRIs), monoamine oxidase inhibitors (MAO1s), reversible inhibitors of monoamine oxidase (RIMA5), serotonin and noradrenaline reuptake inhibitors (SNR1s), corticotropin releasing factor (CRF) antagonists, α-adrenoreceptor antagonists and atypical antidepressants.

Another class of antidepressant agents that may be used in the present invention are noradrenergic and specific serotonergic antidepressants (NaSSAs). A suitable example of a NaSSA is mirtazapine.

Suitable norepinephrine reuptake inhibitors that may be used in the present invention include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof. Another norepinephrine reuptake inhibitor that may be used in the present invention is reboxetine.

Suitable selective serotonin reuptake inhibitors that may be used in the present invention include fluoxetine, fluvoxamine, paroxetine and sertratine, and pharmaceutical acceptable salts thereof.

Suitable monoamine oxidase inhibitors that may be used in the present invention include: isocarboxazid, phenelzine, tranylcypromine and selegiline, and pharmaceutically acceptable salts thereof.

Suitable reversible inhibitors of monoamine oxidase that may be used in the present invention include: moclobemide, and pharmaceutically acceptable salts thereof.

Suitable serotonin and noradrenaline reuptake inhibitors that may be used in the present invention include: venlafaxine, and pharmaceutical acceptable salts thereof.

Suitable CRF antagonists that may be used in the present invention include those compounds described in International Patent Specification Nos. WO 94/13643, WO 94/13644, WO 94/13661, WO 94/13676 and WO 94/13677.

Melatonin receptor agonists have also been shown to have positive effects on sleep disorders including sleeplessness or insomnia. In addition, melatonin agonists such as Valdoxan (also known as agomelatine) (N-[2-(7-methoxy-1-naphthyl)ethyl]acetamide), which is disclosed in U.S. Pat. No. 5,225,442, have been shown to be useful in the treatment of depression. See, e.g., Papp et al, Neuropsychopharmacology 2003 April; 28(4):694-703. By way of background information, the antidepressant agent, agomelatine, behaves as an agonist at melatonin receptors and as an antagonist at serotonin (5-HT) 2C receptors. Besides being an effective antidepressant, Valdoxan has shown particular advantages in improving the often disrupted sleep patterns of depressed patients, without affecting daytime vigilance.

Suitable atypical antidepressants that may be used in the present invention include: bupropion, lithium, nefazodone, trazodone and viloxazine, and pharmaceutical acceptable salts thereof. Another suitable atypical antidepressant is sibutramine.

Other antidepressants that may be used in the present invention include adinazolam, alaproclate, amineptine, amitriptyline/chlordiazepoxide combination, atipamezole, azamianserin, bazinaprine, befuraline, bifemelane, binodaline, bipenamol, brofaromine bupropion, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, tofenacin, tofisopam, toloxatone, tomoxetine, veralipride, viqualine, zimelidine and zometrapine, and pharmaceutical acceptable salts thereof, and St. John's wort herb, or Hypericuin perforatum, or extracts thereof.

Anxiolytics

As used herein, the term "anxiolytic" means a substance capable of reducing anxiety in a subject (whether human or animal). Anxiolytics are compounds that relieve anxiety.

Known anxiolytic compounds include GABA-A agonists such as the benzodiazepines, which are the prototypic anti-anxiety compounds. Benzodiazepines interact with binding sites which are largely defined by the alpha subunit of the GABA-A receptor complex. In older literature, the GABA-A receptor complex was referred to as the "benzodiazepine receptor" or BZR. More than two-dozen benzodiazepines are in clinical use in the United States. Among these are Alprzolam (Xanax), chlordiazepoxide (Librium), and diazepam (Valium).

Suitable benzodiazepines that may be used in the present invention include but are not limited to: alprazolam, chlordiazepoxide, clonazepam, chlorazepate, diazepam, halazepam, lorazepam, oxazepam and prazepam, and pharmaceutically acceptable salts thereof. In addition to benzodiazepines, other suitable classes of antianxiety agent are non-benzodiazepine sedative-hypnotic drugs such as zolpidem; mood-stabilzing drugs such as clobazam, gabapentin, lamotrigine, loreclezole, oxcarbamazepine, stiripentol and vigabatrin; and barbiturates.

Other examples of anxiolytic compounds are neurohormones such as 3-alpha, 5-alpha-pregnanolone (THPROG), muscimol, 5-HTIA agonists or antagonists, especially 5-HTIA partial agonists, compounds having muscarinic cholinergic activity, corticotropin releasing factor (CRF) antagonists and one or more neuropeptide agents.

Suitable CRF antagonists that may be used in the present invention include those compounds described in International Patent Application Nos. WO 94/13643, WO 94/13644, WO 94/13661, WO 94/13676 and WO 94/13677.

A number of other neuropeptides are also believed to be involved in the pathophysiology of anxiety, including, for example, cholecytokinin (CCK), corticotropin-releasing factor and neuropeptide Y. Gastrin releasing peptide (GRP) is known as a potent satiety agent (see Merali, Z. et al. 1994). GRP antagonists are also known in the field of cancer research for their use in inhibiting tumor growth. Gamma-aminobutyric acid (GABA), along with norepinephrine and serotonin, is also known to be important in the regulation of anxiety. GABA is the major inhibitory neurotransmitter in the mammalian central nervous system (CNS) and is utilized for intercellular communication by approximately one-third of all synapses in the CNS. There are two classes of GABA receptors, A and B. The GABA-A receptor is comprised of five peptide subunits (alpha, beta, gamma, delta, and rho) which form a chloride-permeable ion channel coupled to a G-protein. Each of the five subunits may have multiple isoforms. For example, there are six alpha, four beta, three gamma, one delta, and two rho subunits known presently.

5HTA receptor partial agonists have useful anxiolytic and other psychotropic activity and less likelihood of sedation and dependence. Suitable 5-HTA receptor agonists or antagonists that may be used in the present invention include, in particular, the 5-HTA receptor partial agonists buspirone, flesinoxan, gepirone and ipsapirone, and pharmaceutical acceptable salts thereof. An example of a compound with 5-HTIA receptor antagonist/partial agonist activity is pindolol.

Another class of anti-anxiety agent that may be used in the present invention are compound having muscarinic cholinergic activity. Suitable compounds in this class include m1 muscarinic cholinergic receptor agonists such as those compounds described in European Patent Application Nos. 0 709 093, 0 709 094 and 0 773 021, and International Patent Application No. WO 96/12711.

Another class of anti-anxiety agent that may be used in the present invention are compounds acting on ion channels. Suitable compounds in this class include carbamazepine, lamotrigine and valproate, and pharmaceutical acceptable salts thereof.

Neurosteroids are steroids that are synthesized in the brain from sterol precursors (Baulieu, 1981). Neurosteroids include but are not limited to progesterone (PROG), 5a-pregnane-3p-ol-20-one (allopregnanolone), -pregnenolone (PREG), -dehydroepiandrosterone (DHEA), and -PREG and DHEA sulfate esters (PREGS and DHEAS respectively). Apart from their well-known effects on the control of gene expression, neurosteroids modulate several neurotransmission systems, in an excitatory or inhibitory way (Rupprecht et al. 1996). PREGS and DHEAS act as excitatory neurosteroids, since they antagonize the activation of γ-aminobutyric acid type A (GABAA) receptors, whereas they potentiate the activation of the N-methyl-D-aspartate (NMDA)-type of glutamatergic receptors.

Other neurosteroids including PROG and allopregnanolone act as inhibitory neurosteroids, being very potent agonists of GABAA receptors with affinities comparable to those of benzodiazepines. Neurosteroids are involved in several physiopathological events, such as response to stress, depression, anxiety, sleep, epilepsy and memory formation (for a review, see Schumacher et al. 1997). The interaction between neurosteroids and the sigma 1 receptor have been uncovered in binding studies (Maurice et al. 1996; Su et al. 1988; Yamada et al. 1994), then reported in physiological studies regarding several neuronal responses (Bergeron et al. 1994; Debonnel et al. 1996; Monnet et al. 1995). However the exact nature of this interaction, and how it can be used to influence disease states, still remained to be determined.

Specific examples of anti-depressants and anti-anxiety agents that may be used in the methods and pharmaceutical compositions and further uses of this invention are the following compounds citalopram; Disclosed. in EP 347, 066 on Dec. 20, 1989. fluoxetine; Disclosed in U.S. Pat. No. 4,018, 895 on Apr. 19, 1977. sertraline; Disclosed in U.S. Pat. No. 4,536,518 on Aug. 20, 1985. paroxetine; Disclosed in WO 97/24323 on Jul. 10, 1997 nefazadone; Disclosed in Neuropharmacology (1986) 25 (127, 1301-1306). bupropion; Disclosed in U.S. Pat. No. 3,885,046 on Jun. 20, 1975. escitalopram; Disclosed in EP 347,066 on Dec. 20, 1989. zimelidine; Disclosed in EP 303,961 on Feb. 22, 1989. fluvoxamine; Disclosed in WO 96/41633 on Dec. 27, 1996. duloxetine; Disclosed in EP 457,559 on Nov. 21, 1991. milnacipran; Disclosed in FR 2, 581, 060 on Oct. 31, 1986. venlafaxine; Disclosed in EP 112,669 on Jul. 4, 1984. trazodone; Disclosed in U.S. Pat. No. 3,381,009 on Apr. 30, 1968. mirtazapine; Disclosed in GB 1, 543, 171 on Mar. 28, 1979. amitriptyline; Disclosed in BE 634,372 on Jan. 2, 1964. imipramine; Disclosed in FR 5218 on Aug. 7, 1967. lubazodone hydrochloride; Disclosed in WO 94/18182 on Feb. 8, 1994. [Morpholine, 2-[[(7-fluoro-2,3-dihydro-1H-inden-4-yl)oxy]methyl]-, hydrochloride, (2S)-(9c1]; 2-Benzofurancarboxamide, 5-[4-[4-(5-cyano-1H-indol-3-yl)butyl]-1-piperazinyl]-(9CI); mianserin; Disclosed in DE 2, 505, 239 on Aug. 14, 1975. tianeptine; Disclosed in JP 53, 005, 661 on Mar. 1, 1978. minaprine; Disclosed in GB 1, 345,880 on Feb. 6, 1974. phenelzine (MAO-I); Disclosed in U.S. Pat. No. 3,334,017 on Aug. 1, 1967 isocarboxazid (MAO-I); Disclosed in EP 563, 507 on Oct. 6, 1993. tranylcypromine (MAO-I) Disclosed in U.S. Pat. No. 4,016,204 on Apr. 5, 1997 and St John's Wort; Disclosed in WO 99/66914 on Dec. 29, 1999.

Cognitive Enhancing Agents

Examples of cognition-enhancing agents include but are not limited to acetylcholinesterase inhibitors (e.g. donepezil (Donepezil hydrochloride, or Aricept® is described in U.S. Pat. No. 4,895,841, WO2001/066114 and EP1311272B1) and galantamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which inhibit the secretion of Aβ (including γ-secretase inhibitors, β-secretase inhibitors, and GSK-3α inhibitors), compounds which inhibit the aggregation of Aβ, and antibodies which selectively bind to Aβ. Such additional compounds also include growth hormone secretagogues, as disclosed in WO 2004/110443. By way of example, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, Nature, 423 (2003), 435-9.

Combination Therapy

As used herein, the term "Combination therapy" includes for example, separate, simultaneous or sequential delivery of the two active agents.

In one preferred embodiment, the term "combination therapy" refers to the treatment of a subject with a growth factor modulating selective Sigma 1 or Dopamine D3 receptor agonist or a 5HT$_{2c}$ receptor ligand, such as Captodiamine, or a pharmaceutically acceptable salt thereof or mixtures thereof and one or more other anti-depressant agents, such as Valdoxan (agromelatine).

Preferred combinations of (1) a growth factor modulating selective Sigma 1 or Dopamine D3 receptor agonist or a 5HT$_{2c}$ receptor ligand such as Captodiamine or a pharmaceutically acceptable salt thereof or mixtures thereof; and (2) an additional agent selected from the group consisting of: (i) an anti-depressant agent; (ii) an anxiolytic agent; and (iii) a cognitive-enhancing agent as described herein are "synergistic", meaning that the therapeutic effect of co-administering compounds selected from (1) and (2) as defined above is greater than additive. Thus, co-administering both therapeutic agents produces an effect which is greater than the sum of the effects of each agent administered alone. Such synergy is advantageous in that it allows for each therapeutic agent typically to be administered in an amount less than if the combined therapeutic effects were additive. Thus, therapy can be effected for subjects who, for example, do not respond adequately to the use of one component at what would be considered a maximal strength dose. Additionally, by administering the components in lower amounts relative to the case where the combined effects are additive, side effects such as those described above can be minimized or avoided in many cases. Such synergy can be demonstrated by the tests disclosed and described both above and below.

The synergy of such preferred combinations is provided as a further feature of the invention, and accordingly the invention provides a method for achieving a synergistic therapeutically effective level of treatment of symptoms of anxiety and/or depression associated with an "affective" disorder; and/or (b) symptoms associated with a cognitive impairment disorder in a subject in need of same comprising co-administering to a mammal in need of such treatment (1) a growth factor modulating selective Sigma 1 or Dopamine D3 receptor agonist or a 5HT$_{2c}$ receptor ligand, such as Captodiamine, or a pharmaceutically acceptable salt thereof or mixtures thereof; and (2) an additional agent selected from the group consisting of: (i) an anti-depressant agent; (ii) an anxiolytic agent; and (iii) a cognitive-enhancing agent wherein the amount of the first compound alone and the amount of the second agent alone are each insufficient to achieve the synergistic therapeutically effective level of behavioural response treatment and/or pharmacological functional activity (such as, for example, cognitive function), but wherein the combined effect of the amounts of the first and second compounds is greater than the sum of the levels of therapeutic effects of behavioural response treatment and/or pharmacological functional activity, achievable with the individual amounts of the first compound and second agent.

Additional preferred combinations include those which can be taken "on demand", as opposed to needing to be taken chronically.

Additional preferred combinations include those which are "fast acting", meaning that the time taken from administration to the point at which the behavioural response can be modulated is less than about two hours, preferably less than about one hour, more preferably on the order of a half hour or less, and even more preferably within 10 or 15 minutes.

As used herein, the term "Combination therapy" is intended to embrace administration of these therapeutic agents and/or treatments in a separate, sequential manner or simultaneously. In this regard, the term "combination therapy" can cover the co-administration of more than one compound separately but as part of the same therapeutic treatment program or regimen, and it is contemplated that separate administration of each compound, at different times and by different routes, will sometimes be recommended. Thus, two or more compounds need not necessarily be administered at essentially the same time. In a preferred embodiment, administration is timed so that the peak pharmacokinetic effect of one compound coincides with the peak pharmacokinetic effect for the other. If co-administered separately, it is also preferred, so that, for example, two compounds may be administered in an oral dosage form.

Simultaneous administration can be accomplished, for example, by administering to the subject a single capsule having a fixed ratio of each therapeutic agent or in multiple, single capsules for each of the therapeutic agents. In some embodiments, the growth factor modulating selective Sigma 1 or Dopamine D3 receptor agonist or a $5HT_{2c}$ receptor ligand, such as Captodiamine, or a pharmaceutically acceptable salt thereof or mixtures thereof and an additional therapeutic agent(s) are administered nearly simultaneously. These embodiments include those in which the compounds are in the same administrable composition, that is, a single tablet, pill, or capsule, or a single solution for intravenous injection, or a single drinkable solution, or a single dragee formulation or patch, which contains the compounds. The embodiments also include those in which each compound is in a separate administrable composition, but the subject or patient is directed to take the separate compositions nearly simultaneously, such as, for example, when one pill is taken right after the other or that one injection of one compound is made right after the injection of another compound.

Sequential or substantially simultaneous administration of each therapeutic agent can be effected by any appropriate route including, but not limited to oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Sequential administration can also be achieved, for example, using a single dosage form, for example a dosage form such as an oral tablet that has two different layers with different release profiles for the two active ingredients. One of ordinary skill in the art will appreciate that various other forms of administration and application patterns are conceivable within the context of the present disclosure, all of which form subject matter of the invention.

As most of the compounds disclosed herein are orally available and are normally administered orally, oral administration of any drug combination is preferred. In this regard, the compounds may be administered together, in a single dosage form, or may be administered separately. However, oral administration is not the only route or even the only preferred route. For example, transdermal administration may be very desirable for patients who are forgetful or petulant about taking oral medicine. In this regard, any one of the compounds disclosed herein may be administered by one route, such as oral, and the other(s) may be administered by the transdermal, percutaneous, intravenous, intramuscular, intranasal or intrarectal route, in particular circumstances. The route of administration may be varied in any way, limited by the physical properties of the drugs and the convenience of the patient and the caregiver.

In other embodiments, one of a growth factor modulating selective Sigma 1 or Dopamine D3 receptor agonist or a $5HT_{2c}$ receptor ligand, such as Captodiamine, or a pharmaceutically acceptable salt thereof or mixtures thereof and an additional therapeutic compound is administered first and then the other one of the growth factor modulating selective Sigma 1 or Dopamine D3 receptor agonist or a $5HT_{2c}$ receptor ligand such as Captodiamine or a pharmaceutically acceptable salt thereof or mixtures thereof is administered second. In these embodiments, the subject or patient may be administered a composition comprising one of the compounds and then at some time, a few minutes or a few hours later, be administered another composition comprising the other one of the compounds. Also included in these embodiments are those in which the subject or patient is administered a composition comprising one of the compounds on a routine or continuous basis while receiving a composition comprising the other compound occasionally.

In some instances, the term "combination therapy" may encompass the administration of two or more therapeutic compounds as part of separate monotherapy regimens that incidentally and arbitrarily result in the combinations contemplated by the present invention.

Administration of these therapeutic compounds in combination typically is carried out over a defined time period (usually minutes, hours, days or weeks depending upon the combination selected).

Alternatively, for example, all therapeutic compounds may be administered orally or all therapeutic agents may be administered by intravenous injection. The sequence in which the therapeutic agents are administered is not narrowly critical.

The term "Combination therapy" also can embrace the administration of the therapeutic compounds as described above in further combination with other biologically active ingredients and non-drug therapies (such as, for example, surgery or radiation treatment and/or behavioural response treatment, such as but not limited to Cognitive Behavioural Therapy (CBT) and/or Dialectical Behavioural Therapy (DBT) or the like, such as but not limited to voluntary exercise, caloric restriction, intellectual stimulation, and various other treatments for depression (such as electroconvulsive therapy). Where the combination therapy further comprises a non-drug treatment, the non-drug treatment may be conducted at any suitable time so long as a beneficial effect from the combination of the therapeutic agents and non-drug treatment is achieved.

In one embodiment of the invention, the subject, such as a mammal, has cognitive function which is further deteriorated by the administration of another agent. In that case the growth factor modulating selective Sigma 1 or Dopamine D3 receptor agonist or a $5HT_{2c}$ receptor ligand, such as Captodiamine, or a pharmaceutically acceptable salt thereof or mixtures thereof is given in combination with such agent.

The term "antidepressant effective amount", as used herein, refers to an amount that is effective in treating depression.

The terms "anxiolytic effective amount" and "antianxiety effective amount", as used herein, refer to an amount that is effective in treating anxiety.

Pharmaceutical Compositions

In one aspect, the invention includes a growth factor modulating selective Sigma 1 or Dopamine D3 receptor agonist or a $5HT_{2c}$ receptor ligand, such as Captodiamine, or a pharmaceutically acceptable salt thereof or mixtures thereof according to the present invention administered as the active ingredient of a pharmaceutically acceptable composition, having activity in the treatment of symptoms of anxiety and/or depression associated with an "affective" disorder; and/or symptoms associated with a cognitive impairment disorder in a subject in need of same. This pharmaceutical composition can be prepared by conventional procedures, for instance by mixing the active agent with a pharmaceutically acceptable, therapeutically inert organic and/or inorganic carrier, diluents or excipient materials (including combinations thereof). The pharmaceutical compositions may be for human or animal usage in human and veterinary medicine and will typically comprise any one or more of a pharmaceutically acceptable diluent, carrier, or excipient.

As used herein, a "pharmaceutically acceptable" carrier, diluents or excipient is one that is suitable for use with humans and/or animals without undue adverse side effects (such as toxicity, irritation, and allergic response) commensurate with a reasonable benefit/risk ratio. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice.

The following present some non-limiting examples of formulations.

Formulation 1: A tablet is prepared using the following ingredients:

|  | Weight/mg |
|---|---|
| Agent | 250 |
| Cellulose, microcrystalline | 400 |
| Silicon dioxide, fumed | 10 |
| Stearic acid | 5 |
| Total | 665 |

The components are blended and compressed to form tablets each weighing 665 mg.

Formulation 2: An intravenous formulation may be prepared as follows:
Agent 100 mg
Isotonic saline 1,000 ml
Modes of Administration The invention further provides a growth factor modulating selective Sigma 1 or Dopamine D3 receptor agonist or a $5HT_{2c}$ receptor ligand, such as Captodiamine, or a pharmaceutically acceptable salt thereof or mixtures thereof for use in the treatment of (a) symptoms of anxiety and/or depression associated with an "affective" disorder; and/or (b) symptoms associated with a cognitive impairment disorder in a subject in need of same by for example, administering to an individual a growth factor modulating selective Sigma 1 or Dopamine D3 receptor agonist or a $5HT_{2c}$ receptor ligand such as Captodiamine or a pharmaceutically acceptable salt thereof or mixtures thereof.

As used herein, the term "administered" includes but is not limited to delivery by a mucosal route, for example, as a nasal spray or aerosol for inhalation or as an ingestable solution such as by an oral route, or by a parenteral route where delivery is by an injectable form, such as, for example, by a rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) transdermal, intraperitoneal, intracranial, intracerebroventricular, intracerebral, intravaginal, intrauterine, or parenteral (e.g., intravenous, intraspinal, intracavernosal, subcutaneous, transdermal or intramuscular) route.

Preferably the compositions (or component parts thereof) of the present invention are administered orally.

The growth factor modulating selective Sigma 1 or Dopamine D3 receptor agonist or a $5HT_{2c}$ receptor ligand, such as Captodiamine, or a pharmaceutically acceptable salt thereof or mixtures thereof may also be administered parenterally, for example, intravenously, intra-arterially, intraperitoneally, intrathecally, intraventricularly, intraurethrally, intrasternally, intracranially, intramuscularly or subcutaneously, or it may be administered by infusion techniques. For such parenteral administration it is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The growth factor modulating selective Sigma 1 or Dopamine D3 receptor agonist or a $5HT_{2c}$ receptor ligand, such as Captodiamine, or a pharmaceutically acceptable salt thereof or mixtures thereof can also be administered intranasally or by inhalation.

Alternatively, the growth factor modulating selective Sigma 1 or Dopamine D3 receptor agonist or a $5HT_{2c}$ receptor ligand, such as Captodiamine, or a pharmaceutically acceptable salt thereof or mixtures thereof may be administered in the form of a suppository or pessary, or it may be applied topically in the form of a gel, hydrogel, lotion, solution, cream, ointment or dusting powder.

In one variation, the growth factor modulating selective Sigma 1 or Dopamine D3 receptor agonist or a $5HT_{2c}$ receptor ligand, such as Captodiamine, or a pharmaceutically acceptable salt thereof or mixtures thereof is administered to a subject as a sustained release form or as part of a sustained release system.

A desired duration may be at least the drug elimination half life of the administered compound and may be, for example, at least about 6 hours or at least about 12 hours or at least about 24 hours or at least about 30 hours or at least about 48 hours or at least about 72 hours or at least about 96 hours or at least about 120 hours or at least about 144 or more hours, and can be at least about one week, at least about 2 weeks, at least about 3 weeks, at least about 4 weeks, at least about 8 weeks, or at least about 16 weeks or more.

Routes of administration of a growth factor modulating selective Sigma 1 or Dopamine D3 receptor agonist or a $5HT_{2c}$ receptor ligand, such as Captodiamine, or a pharmaceutically acceptable salt thereof or mixtures thereof are typically oral or parenteral.

Dosage

The dosage of the growth factor modulating selective Sigma 1 or Dopamine D3 receptor agonist or a $5HT_{2c}$ receptor ligand, such as Captodiamine, or a pharmaceutically acceptable salt thereof or mixtures thereof of the present invention will depend on the disease state or condition being treated and other clinical factors including subject age, weight, diet and condition and response of the individual and the route and time of administration of the compound. Depending upon the half-life of the compound in the particular subject, the agent can be administered from several times per day to once a week. It is to be understood that the present invention has application for both human and veterinary use. The methods of the present invention contemplate single as well as multiple administrations, given either simultaneously or over an extended period of time. By way of example, suitable treatment may be given 1 or 2 or 3 times daily, depending upon clearance rate.

For use herein, unless clearly indicated otherwise, the compounds may be administered to the individual by any available dosage form.

Preferably the pharmaceutical composition is administered as a once daily dosage form.

In one variation, the compound is administered to the individual as a conventional immediate release dosage form.

By way of example, in one embodiment, the pharmaceutical composition of the present invention comprising a growth factor modulating selective Sigma 1 or Dopamine D3 receptor agonist or a $5HT_{2c}$ receptor ligand, such as Captodiamine, or a pharmaceutically acceptable salt thereof or mixtures thereof may contain, per dosage unit form, such as, for example, a capsule, tablet, powder injection, teaspoonful, suppository and the like form, from about 20 to 7000 mg of the active ingredient.

In another embodiment, an amount of a growth factor modulating selective Sigma 1 or Dopamine D3 receptor agonist or a $5HT_{2c}$ receptor ligand, such as Captodiamine, or a pharmaceutically acceptable salt thereof or mixtures thereof in a delivery form may be any effective amount, which may be from about 10 ng to about 1500 mg or more.

In one variation, a delivery form, such as a sustained release system, may comprise less than about 30 mg of a growth factor modulating selective Sigma 1 or Dopamine D3 receptor agonist or a $5HT_{2c}$ receptor ligand, such as Captodiamine, or a pharmaceutically acceptable salt thereof or mixtures thereof. In another variation, a delivery form, such as a single sustained release system capable of multi-day administration, comprises an amount of compound such that the daily dose of compound is less than about 30 mg of a growth factor modulating selective Sigma 1 or Dopamine D3 receptor agonist or a $5HT_{2c}$ receptor ligand, such as Captodiamine, or a pharmaceutically acceptable salt thereof or mixtures thereof.

In another embodiment, the desired dose may be presented in a single dose or as divided doses administered at appropriate intervals, for example, two to four or more sub-doses per day. By way of example, a useful intravenous dose is typically from about 5 and 50 mg and a useful oral dosage is typically from about 50 to 600 mg, preferably from about 20 and 200 mg.

In a further embodiment, the subject in need of the above mentioned treatment is administered a dose of a growth factor modulating selective Sigma 1 or Dopamine D3 receptor agonist or a $5HT_{2c}$ receptor ligand, such as Captodiamine, or a pharmaceutically acceptable salt thereof or mixtures thereof as above defined which ranges from about 0.3 to about 100 mg/kg of body weight per day.

In yet another embodiment, a growth factor modulating selective Sigma 1 or Dopamine D3 receptor agonist or a $5HT_{2c}$ receptor ligand, such as Captodiamine, or a pharmaceutically acceptable salt thereof or mixtures thereof is administered orally as a tablet or capsule comprising about 100 mg of N-desmethylclozapine. Thus, for example, about 100 mg capsules may be administered twice daily to achieve an about 200 mg per day dose. To achieve a 400 mg per day dose, two about 100 mg capsules may be administered twice daily (totaling 4 capsules over the day).

In some embodiments, a growth factor modulating selective Sigma 1 or Dopamine D3 receptor agonist or a $5HT_{2c}$ receptor ligand, such as Captodiamine, or a pharmaceutically acceptable salt thereof or mixtures thereof is administered orally in an amount totaling about 200 mg per day or about 400 mg per day. In some such embodiments, a growth factor modulating selective Sigma 1 or Dopamine D3 receptor agonist or a $5HT_{2c}$ receptor ligand, such as Captodiamine, or a pharmaceutically acceptable salt thereof or mixtures thereof is advantageously administered twice daily (e.g., about 100 mg twice daily or about 200 mg twice daily). While not being bound by any particular theory, twice daily administration is believed to attenuate fluctuations in blood levels and improve tolerability.

In yet further embodiments, the dose which is administered to a subject is titrated to the final dose. For example, in some embodiments, a final dose of about 200 mg per day dose is achieved by first administering about 100 mg per day (e.g., about 50 mg twice daily) for a certain period of time followed by administering about 200 mg per day (e.g., about 100 mg twice daily). In some embodiments, a final dose of about 400 mg per day dose is achieved by first administering about 100 mg per day (e.g., about 50 mg twice daily) for a certain period of time, followed by administering about 200 mg per day (e.g., about 100 mg twice daily) for a certain period of time, followed by administering about 300 mg per day (e.g., about 150 mg twice daily) for a certain period of time, followed by administering the final about 400 mg per day (e.g., about 200 mg twice daily). Prior to each dose escalation, a physician may evaluate the patient to determine if a continued dose escalation is warranted. In some cases, the physician may decide to extend the amount of time that a lower dose is administered prior to escalation. In some embodiments, the physician may decide to not increase the dosage any further, thereby choosing as a final dose a dose less than the originally planned final dose. In other embodiments described above, the desired administration doses may be achieved by administering a single capsule or tablet. Alternatively, the doses may be achieved by administering multiple capsules or tablets simultaneously or in sequence. In further embodiments, all doses are achieved using tablets or capsules containing 50 mg or 100 mg of a growth factor modulating selective Sigma 1 or Dopamine D3 receptor agonist or a $5HT_{2c}$ receptor ligand, such as Captodiamine, or a pharmaceutically acceptable salt thereof or mixtures thereof or combinations thereof.

Preferably the maintenance dose of the pharmaceutical composition of a growth factor modulating selective Sigma 1 or Dopamine D3 receptor agonist or a $5HT_{2c}$ receptor ligand, such as Captodiamine, or a pharmaceutically acceptable salt thereof or mixtures thereof is a unit oral dosage form, which comprises from about 20 mg and 50 mg Captodiamine.

In some embodiments, suitable dosages of a growth factor modulating selective Sigma 1 or Dopamine D3 receptor agonist or a $5HT_{2c}$ receptor ligand, such as Captodiamine, or a pharmaceutically acceptable salt thereof or mixtures thereof are typically about 0.05 to about 50 mg/day, for example about 0.1 to about 40 mg/day or about 0.2 to about 20 mg/day, preferably about 4 to about 20 mg/day. Optionally, gradually increasing dosages can be administered. That is, treatment can optionally start with relatively low doses which are incrementally increased until a maintenance dose is reached In preferred embodiments, a growth factor modulating selective Sigma 1 or Dopamine D3 receptor agonist or a $5HT_{2c}$ receptor ligand, such as Captodiamine, or a pharmaceutically acceptable salt thereof or mixtures thereof may be administered in a single daily dose, or the total daily dosage may be administered as a plurality of doses, (e.g., divided doses two, three or four times daily). Furthermore, a growth factor modulating selective Sigma 1 or Dopamine D3 receptor agonist or a $5HT_{2c}$ receptor ligand, such as Captodiamine, or a pharmaceutically acceptable salt thereof or mixtures thereof may be administered in intranasal form via topical use of suitable intranasal vehicles, or via transdermal routes, or via topical use of ocular formulations, or using those forms of transdermal skin patches well known to persons skilled in the art.

Dosage Regimen

The growth factor modulating selective Sigma 1 or Dopamine D3 receptor agonist or a $5HT_{2c}$ receptor ligand, such as Captodiamine, or a pharmaceutically acceptable salt thereof or mixtures thereof may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

In one embodiment, a treatment regimen involving a dosage form of compound, whether immediate release or a sustained release system, may involve administering the compound to the individual in dose of from about 0.1 and about 10 mg/kg of body weight, at least once a day and during the period of time required to achieve the therapeutic effect. In other variations, the daily dose (or other dosage frequency) of a compound of Formula I as described herein is from about 0.1 to about 8 mg/kg; or from about 0.1 to about 6 mg/kg; or from about 0.1 to about 4 mg/kg; or from about 0.1 to about 2 mg/kg; or from about 0.1 to about 1 mg/kg; or from about 0.5 to about 10 mg/kg; or from about 1 to about 10 mg/kg; or from about 2 to about 10 mg/kg; or from about 4 to about 10 mg/kg; or from about 6 to about 10 mg/kg; or from about 8 to about 10 mg/kg; or from about 0.1 to about 5 mg/kg; or from about 0.1 to about 4 mg/kg; or from about 0.5 to about 5 mg/kg; or from about 1 to about 5 mg/kg; or from about 1 to about 4 mg/kg; or from about 2 to about 4 mg/kg; or from about 1 to about 3 mg/kg; or from about 1.5 to about 3 mg/kg; or from about 2 to about 3 mg/kg; or from about 0.01 to about 10 mg/kg; or from about 0.01 to 4 mg/kg; or from about 0.01 mg/kg to 2 mg/kg; or from about 0.05 to 10 mg/kg; or from about 0.05 to 8 mg/kg; or from about 0.05 to 4 mg/kg; or from about 0.05 to 4 mg/kg; or from about 0.05 to about 3 mg/kg; or from about 10 kg to about 50 kg; or from about 10 to about 100 mg/kg or from about 10 to about 250 mg/kg; or from about 50 to about 100 mg/kg or from about 50 to about 200 mg/kg; or from about 100 to about 200 mg/kg or from about 200 to about 500 mg/kg; or a dosage over about 100 mg/kg; or a dosage over about 500 mg/kg. In some embodiments, a daily dosage of Meparfynol is administered, such as a daily dosage which may include but is not limited to, a daily dosage of about 0.05 mg/kg.

Dosage Frequency

In one embodiment, the dosing frequency can be about a once weekly dosing. In other embodiments, the dosing frequency can be about a once daily dosing. The dosing frequency can be more than about once weekly dosing. The dosing frequency can be less than three times a day dosing. The dosing frequency can be less than about three times a day dosing. The dosing frequency can be about three times a week dosing. The dosing frequency can be about a four times a week dosing. The dosing frequency can be about a two times a week dosing. The dosing frequency can be more than about once weekly dosing but less than about daily dosing. The dosing frequency can be about a once monthly dosing. The dosing frequency can be about a twice weekly dosing. The dosing frequency can be more than about once monthly dosing but less than about once weekly dosing. The dosing frequency can be intermittent (e.g., once daily dosing for 7 days followed by no doses for 7 days, repeated for any 14 day time period, such as about 2 months, about 4 months, about 6 months or more). The dosing frequency can be continuous (e.g., once weekly dosing for continuous weeks). Any of the dosing frequencies can employ any of the compounds described herein together with any of the dosages described herein, for example, the dosing frequency can be a once daily dosage of less than 0.1 mg/kg or less than about 0.05 mg/kg of a growth factor modulating selective Sigma 1 or Dopamine D3 receptor agonist or a $5HT_{2c}$ receptor ligand, such as Captodiamine, or a pharmaceutically acceptable salt thereof or mixtures thereof.

Psycho-Pharmacological Tests

The usefulness of a growth factor modulating selective Sigma 1 or Dopamine D3 receptor agonist or a $5HT_{2c}$ receptor ligand, such as Captodiamine, or a pharmaceutically acceptable salt thereof or mixtures thereof for use in the treatment of symptoms of anxiety and/or depression associated with an "affective" disorder; and/or symptoms associated with a cognitive impairment disorder in a subject in need of same is demonstrated in standard pharmacological test procedures, some of which are outlined below as follows: By way of example, compounds of the present invention may be screened in-vivo to determine, their capacity, after administration, to affect the behavioural characteristics of the treated subject.

Open Field Test

The open field test is designed to measure behavioural responses such as locomotor activity, hyperactivity, and exploratory behaviors. Open field is also used as a measure of anxiety. Rats and mice tend to avoid brightly illuminated, novel, open spaces, so the open field environment acts as an anxiogenic stimulus and allows for measurement of anxiety-induced locomotor activity and exploratory behaviors. Like the elevated maze test described below, open field testing is a one trial test with little or no impact on the animal's subsequent behavior. The apparatus for the open field test was a square (100 cm by 100 cm) made of white Perspex. Each rat is placed in a corner of the field and its behavior recorded for five minutes. All activity is recorded by a video camera mounted above the open field and scored in real-time (or digitized and scored later) by the advanced motion-recognition software package Ethovision by Noldus, that detects and analyzes the movements of the rat or mouse. The total distance, average speed, rearing/elongation behavior, and time spent in various parts of the field (such as, for example, the border areas vs. the open, middle area) is measured and analysed. Testing is carried out in a temperature, noise and light controlled room.

Novel Object Recognition (NOR) Test

This test is useful for evaluating the role of experimental manipulations on cognition. The recognition test is based on the natural tendency of rodents to investigate a novel object instead of a familiar one. The choice to explore the novel object reflects the use of learning and (recognition) memory processes. Novel Object Recognition (NOR) is based on the premise that rodents will explore a novel object more than a familiar one, but only if they remember the familiar one. This tendency is actually shared by humans, as looking time is often used to make inferences about an infant's memory in the absence of explicit, verbal recognition.

Description I

Before training the animals with objects, they are first allowed to acclimatize to the testing environment, a white Perspex box (30 cm by 20 cm) equipped with an overhead camera. After an acclimation session, the animals are ready for the training stage. This stage involves the introduction of two identical objects (Lego Duplo) to the environment before allowing the rodent to explore for a period of five minutes: Following the training period, the rodent is removed from the environment for a delay period which can range from 5 minutes to 24 hours, depending on the type of memory being tested. After the delay, the rodent is returned to the arena, where one of the original objects has been replaced by a new one, such as a glass container.

Description II

In the two-trial novel object recognition task, a rodent is placed in an enclosure and exposed for a set length of time to two identical objects that are located a specified distance from each other. The rodent is then removed from the environment and a predetermined amount of time is allowed to pass. The subject is then retested in the same environment except that one of the two previously used (familiar) objects is replaced with a novel object that differs from the familiar object in shape, texture and appearance (such as, for example, plastic block is replaced with a metal ball), and the rodent's behavior is recorded.

The amount of time that the rodents spends exploring each object can be calculated by hand or by using a computer program receiving input from the overhead camera. The literature describes a variety of methods for analyzing results. One technique involves dividing the time spent exploring the novel object by the total time spent exploring either object, yielding % novel exploration. An alternative technique is used to calculate the discrimination ratio, defined as the difference in exploration time for the objects divided by total exploration time. The method of analysis should be suited to the specific experimental setup.

Though simple by design, NOR is actually quite flexible. For instance, changing the duration of the delay period allows one to selectively test short-term or long-term memory. Alternatively, the NOR protocol can be used to selectively test the effects of an acute drug treatment on a specific stage of memory formation. The experimenter can manipulate memory encoding, consolidation or retrieval by injecting the drug prior to the training, delay or testing period, respectively. The desired result is a reduced exploratory time and enhanced spatial learning in response to a test agent in the novel object recognition test.

Pre-Pulse Inhibition Test

The overall goal of this test is to evaluate the effect of an agent on sensory processing (which is a form of working memory).

Prepulse inhibition is a procedure whereby a preceding stimulus attenuates the startle response. The reduced ability to filter out irrelevant auditory stimulation is a characteristic which is thought to contribute to certain manifestations of conditions including inattention, distractibility, and cognitive deficits. The test is quite useful for evaluating transgenic models of schizophrenia as well as to screen potential antipsychotic drugs.

Prepulse Inhibition (PPI) is a neurological phenomenon in which a weaker prestimulus (prepulse) inhibits the reaction of an organism to a subsequent strong startling stumulus (pulse). The stimuli are usually acoustic, but tactile, light, airpuff stimuli are also used. The reduction of the amplitude of startle reflects the ability of the nervous system to temporarily adapt to a strong sensory stimulus when a preceding weaker signal is given to warn the organism. PPI is detected in numerous species ranging from mice to human. Although the extent of the adaptation affects numerous systems, the most comfortable to measure are the muscular reactions, which are normally diminished as a result of the nervous inhibition.

Prepulse inhibition is a cross-species phenomenon (that is, it is present in mammals ranging from mice to humans), yet it is relatively absent among schizophrenic patients and, more recently discovered, among patients with Alzheimer's disease and in people under the influence of drugs, surgical manipulations, mutations. Human studies of PPI have been summarised in a review by Braff et al. in 2001 *Human studies of prepulse inhibition of startle: normal subjects, patient groups, and pharmacological studies*. Psychopharmacology 2001; 156:234-258). Disruptions of PPI are studied in humans and many other species. The most studied are deficits of PPI in schizophrenia, although this disease is not the only one to cause such deficits. They have been noted in panic disorder (Ludewig, et al., 2005), schizotypal personality disorder (Cadenhead K S, Geyer M A, Braff D L. *Impaired startle prepulse inhibition and habituation in patients with schizotypal personality disorder*. Am J Psychiatry. 1993 December; 150(12):1862-7), obsessive-compulsive disorder (Swerdlow et al., 1993), Huntington's disease (Swerdlow N R, Paulsen J, Braff D L, Butters N, Geyer M A, Swenson M R. *Impaired prepulse inhibition of* acoustic and tactile startle response in patients with Huntington's Disease. *J Neurol Neurosur Psychiatry* 1995; 58: 192-200), nocturnal enuresis and attention deficit disorder (Ornitz et al. 1992), and Tourette's syndrome (Swerdlow et al. 1994; Castellanos et al. 1996). According to one study, people who have temporal lobe epilepsy with psychosis also show decreases in PPI, unlike those who have TLE without psychosis (Morton, N., Gray, N. S., Mellers, J., Toone, B., Lishman, W. A., & Gray, J. A. (1994). *Prepulse inhibition in temporal lobe epilepsy*. Schizophrenic Research, 15, 191). Therefore, PPI deficits are not typical to specific disease, but rather tell of disruptions in a specific brain circuit.

PPI deficits represent a well-described finding in schizophrenia, with the first report dating back to 1978 (Braff D, Stone C, Callaway E, Geyer M, Glick I, Bali L. *Prestimulus effects on human startle reflex in normals and schizophrenics*. Psychophysiology. 1978 July; 15(4):339-43. The abnormalities are also noted in unaffected relatives of the patients. In one study, patients failed to show increased PPI to attended prepulses. Dopamine, which plays a major role in schizophrenia, had been shown to regulate sensorimotor gating in rodent models. These findings fit to the dopamine hypothesis of schizophrenia. In theory, PPI disruption in schizophrenia may be related to the processes of sensory flooding and cognitive fragmentation.

Antipsychotic medications have been shown to increase PPI in patients, with atypical antipsychotics having more effect. Patients display the same gender difference in PPI as healthy people: males have higher PPI compared to females. One notable finding is that patients are specifically deficient in PPI with 60 ms prepulse intervals relative to intervals of other lengths; this remains so even under antipsychotic treatment (see Swerdlow N R, Light G A, Cadenhead K S, Sprock J, Hsieh M H, Braff D L. (2006) *Startle gating deficits in a large cohort of patients with schizophrenia*. Arch Gen Psych. December, 2006; 63:1325-1335).

Testing for PPI

Murine models are widely used to test hypotheses linking genetic components of various diseases with sensorimotor gating. While some of the hypotheses stand to the test, others are not, as some mice models show unchanged or increased PPI contrary to the expectations, as in the tests of COMT-deficient mice. Certain surgical procedures also disrupt PPI in animals, helping to unravel the underlying circuitry. Many animal studies of PPI are undertaken in order to understand and model the pathology of schizophrenia. Schizophrenia-like PPI disruption techniques in rodents have been classified in one review into four models which are described as follows: (i) PPI impairment driven by dopamine-receptor agonists, most validated for antipsychotic studies; (ii) PPI impairment by 5-HT2 receptor agonists; (iii) PPI impairment by NMDAR antagonists; and (iv) PPI impairment by developmental intervention (isolation rearing, maternal deprivation). Diverse chemical compounds are tested on animals with such deficits. Compounds that are able to restore PPI could be further investigated for their potential antipsychotic role.

An example of one way of testing for PPI: In the prepulse inhibition (PPI) procedure, the rodent is placed in a small chamber and exposed to a brief pulse of noise. The test is used to assess the subject's ability to "gate" or filter environmental information. In the acoustic (startle model) of sensorimotor gating, a weak acoustic stimulus (ie, the prepulse) decreases the reflexive flinching response (startle) produced by a second, more intense, stimulus (the pulse).

The main three parts of the procedure are prepulse, startle stimulus, and startle reflex. Different prepulse-to-pulse intervals, or lead intervals, are used: 30, 60, 120, 240 and 480 ms. Lead interval counts from the start of prepulse to the start of the pulse. With the interval exceeding 500 ms, prepulse facilitation, such as increased response, is most likely to follow. Burst of white noise is usually used as acoustic startle stimulus. Typical durations are 20 ms for prepulse and 40 ms for pulse. Background noise with 65-70 dB is used in human studies, and 30-40 dB in rodent experiments. Prepulse is typically set 3-12 dB louder than background. Startle response is measured in rodents using the so-called automated "startle chambers" or "stabilimeter chambers", with detectors recording whole-body reaction. In humans, the movements of oculomotor muscles ("eye-blink reflex" or "eye-blink response" assessed using electromyographic recording of orbicularis oculi muscle and by oculography) could be used as a measure. Pulse-alone results are compared to prepulse-plus-pulse, and the percentage of the reduction in the startle reflex represents prepulse inhibition. Possible hearing impairment must be taken into account, as, for example, several strains of mice develop high frequency hearing loss when they mature.

Elevated X-Maze Test

The elevated X-Maze, otherwise known as the Elevated Plus Maze is a test that relies on the inherent conflict between exploration of a novel area and avoidance of its aversive features. The test may be used in male or female rats or mice or male gerbils. It is reliable in a wide range of strains and in group-housed or isolated animals. The maze consists of four arms in the form of an x or plus: two open arms and two arms of the same size, also with an open roof but enclosed by walls. The two open arms are opposite each other and converge into a central platform. The animal under investigating is observed by a video camera and its movements scored by the tracking software Ethovision by Noldus. During the experiment the animal is placed in the central platform of the maze facing an open arm and is observed for 5 minutes with the following being measured: number of entries into open arms, number of entries into closed arms, time spent in open arms, time spent in closed arms and finally the time spent in the central square (File et al., Current Protocols in Neuroscience (2004) 8.3.1-8.3.22).

Forced Swim Test

The Behavioural Despair Test (also called the Porsolt test or Forced Swimming Test) is a test used to measure the effect of antidepressant drugs on the behaviour of laboratory animals (typically rats or mice). The experimental procedure for the Forced Swim Tests differs between rats and mice. Rats are subjected to two trials during which they are forced to swim in an acrylic glass cylinder filled with water, and from which they cannot escape. The first trial lasts 15 minutes. Then, after 24-hours, a second trial is performed that lasts 5 minutes. Mice only require a single experimental session and a single drug administration. The time that the test animal spends without moving in the second trial is measured. This immobility time is decreased by antidepressants. Porsolt R D, Bertin A, Jalfre M. (1977). "Behavioral despair in mice: a primary screening test for antidepressants". *Archives Internationales de Pharmacodynamie et de Therapie* 229 (2): 327-336. Petit-Demouliere B, Chenu F, Bourin M. (2005). "Forced swimming test in mice: a review of antidepressant activity.". *Psychopharmacology (Berl)* 177 (3): 245-255.

Forced Swim Test (FST) in Mice:

Day 1:

1. Fill a 12 cm diameter glass cylinder to 10 cm with 22° C. water.
2. Place two animals simultaneously in individual side-by-side cylinders separated by an opaque screen.
3. Place mice in the cylinders for 6 minutes.
4. Observe the behaviour of the mice for the last 4-minutes of the 6-minute experimental session.
5. Sessions are videotaped and scored blind, Immobility is scored by summing the time spent immobile; movements necessary to maintain the animals head above water were not scored with data from treated groups compared with data from the control group using nonpaired Student's t tests (two tailed).
6. Animals are dried with paper towels and heat lamps.

FST in Rats:

Habituation Session (Day 1)

1. On Day 1, 25 hr prior to testing, place the animals in the experimental room 60 min before the beginning of the habituation session. Randomly assign animals to a drug treatment, but give all animals within a cage the same treatment. Make food and water available throughout the experiment.
2. Weigh two animals individually, then place one rat in each of the two cylinders (20 cm in diameter×40 cm high) containing water (25° C.) for 15 min (habituation session). No scoring of immobility is performed during the habituation session. This session is needed to habituate the rats to the experimental situation and to induce a stable, high level of immobility during the actual test. Individual weights are used to calculate the dose per animal and for documentation purposes
3. Remove the rats from the cylinders, dry them with a cloth towel, and place them into a cage.

Day 2:
1. Repeat day 1 set up.
2. Two animals simultaneously placed in individual side-by-side cylinders separated by an opaque screen and are videotaped. Observe their behavior for 5 min.
3. Score animals for immobility, swimming, and climbing by using a sampling technique to rate the predominant behavior over a 5 second interval (therefore 120 total counts over 10 minutes).
4. Immobility is defined as absence of all movement except motions required to keep the head above the water. Climbing is defined as thrashing movements along the sides of the water tank while swimming behavior consists of horizontal motion moving from one quadrant of the water tank to another.

Water Maze Spatial Learning Test

The Morris Water Maze (MWM) is a test of spatial learning for rodents that relies on distal cues to navigate from start locations around the perimeter of an open swimming arena to locate a submerged escape platform. Spatial learning is assessed across repeated trials and reference memory is determined by preference for the platform area when the platform is absent.

The test apparatus consists of a large circular pool (1 m diameter, 80 cm high, temperature 26° C.) with a platform (11 cm diameter) submerged 1.5 cm below the surface. Both the pool and the platform were constructed of black polyvinyl plastic, which offered no intra-maze cues. The experimental room contained several extra-maze visual cues. During training the platform was hidden in the same quadrant 30 cm away from the edge of the maze. There were five trials, each of them beginning with the rat facing the wall of the maze in one of three different locations. The time taken for the rat to find the platform within a 90 s period was recorded. Probe trials where the platform was removed from the maze and the time the animal spent in the target quadrant were also performed.

Reversal and shift trials enhance the detection of spatial impairments. Trial-dependent, latent and discrimination learning can be assessed using modifications of the basic protocol. Search-to-platform area determines the degree of reliance on spatial versus non-spatial strategies. Cued trials determine whether performance factors that are unrelated to place learning are present. Escape from water is relatively immune from activity or body mass differences, making it ideal for many experimental models. The MWM has proven to be a robust and reliable test that is strongly correlated with hippocampal synaptic plasticity and NMDA receptor function.

As the Examples demonstrate, the combined effect of Captodiamine on open-field behaviour and performance in the elevated X-maze suggests it to have anxiolytic actions that most likely contribute to its precognitive actions in water maze spatial paradigm and antidepressant actions in the forced swim test.

Human Equivalents of the Novel Object Recognition Test

Novel object recognition (NOR) is a memory test based on the on the differential exploration of familiar and new objects. According to the authors who originally devised the test (Ennaceur and Delacour, 1988 A new one-trial test for neurobiological studies of memory in rats. 1, Behavioral data. Behavioural Brain Research 31, 47-59), it has several interesting characteristics: (a) It is similar to visual recognition tests widely used in subhuman primates, this allows interspecies comparisons; (b) It is entirely based on the spontaneous behavior of rats and can be considered as a 'pure' working-memory test completely free of reference memory component; and (c) It does not involve primary reinforcement such as food or electric shocks; this makes it comparable to memory tests currently used in man. For our interpretation of NOR test, we focused primarily on its ability to evaluate the effect a drug has on working memory. There are several tests used to evaluate working memory in humans, some of the main one are outlined below:

Visuo-spatial Delayed Response Tasks

This task involves presentation of a visual cue (a black dot) on a computer screen. The cue is removed for a delay of either 0 or 8 seconds. After the delay period, the subjects indicate the screen location of the cue with a fine-pointed light pen. Improvements in working memory can be assessed by checking the accuracy of pin-pointing the location of cue after 8 seconds.

Card Sorting Tasks

These tasks assess a persons ability to 'set shift' i.e. the ability to display flexibility in the face of changing schedules of reinforcement. A well-known version of this task is known as the Wisconsin Card Sorting Test or WCST. A WCST deck is made up of 128 response cards, and 4 stimulus cards. Each stimulus card has a different number, colour, and shape of symbol: a red triangle, two green stars, three yellow crosses, and four blue circles. The response cards each have a different combination of those parameters, one has four red crosses, another has two yellow circles, and so forth. At the beginning of the test, the experimenter places the four stimulus cards on the table, and tells the subject that he is to sort the cards in the response deck on to each pile. This is purposefully ambiguous in order to make sure the subject will make incorrect placements, making it possible to tell how well the subject is picking up sorting rules during the game. The subject is also warned that the rules of sorting will change during the experiment. From then on the experimenter answers only "right" or "wrong" to each card placement by the subject. Since there are only three possible characteristics to judge by (number, colour, and shape), the experimenter can only change sorting rules twice. With each change of sorting rule, the experimenter watches to see how long it takes the subject to figure out the rules have changed, how long it takes him to learn the new rules, and what mistakes he makes while learning them.

Associative Memory Tasks

There are several types of associative memory test performed in psychological testing, a sample test would be the fan effect paradigm. Is this test subjects have to memorize a series of sentences which encode conflicting information about the associations among various elements (e.g. 'The doctor is in the house' and 'The doctor is in the park'). This task measures susceptibility to interference in memory, as well as the ability to maintain associations under conditions of interference.

Context Memory Tasks

The ability to associate items in memory has been linked to prefrontal function in a variety of context memory studies. A typical context memory task is where subjects are shown two lists of words, and later have to remember on which of the two lists each word has originally appeared The Stroop Task In psychology, the Stroop effect is a demonstration of interference in the reaction time of a task. When a word such as blue, green, red, etc. is printed in a colour differing from the colour expressed by the word's semantic meaning (e.g. the word "red" printed in blue ink), a delay occurs in the processing of the word's colour, leading to slower test reaction times and an increase in mistakes. This can be used to assess working memory as it is or by modifying the test by adding conditions. A typical test could include two conditions: such as naming the color of a series of color blocks, and naming the color of a series of conflicting colour words (e.g. 'red' printed in blue ink). The difference in time to complete the two tasks was can be used as a measure of interference.

Cognitive Function Tests in Humans

Where a neurodegenerative disorder affects a cognitive ability, a subject can be diagnosed by any one of a number of standardized cognitive assays, e.g., the Mini-Mental State Examination, the Blessed Information Memory Concentration assay, or the Functional Activity Questionnaire. See, e.g., Adelman et al. (2005), Am. Family Physician, 71(9):1745-1750. Indeed, in some cases a subject can also be diagnosed as having a high risk of developing a chronic neurodegenerative condition (e.g., Alzheimer's disease), even in the absence of overt symptoms. For example, the risk of Alzheimer's disease in a subject can be determined by detecting a decrease in the volumes of the subject's hippocampus and amygdala, using magnetic resonance imaging. See, e.g., den Heijer et al. (2006), Arch Gen Psychiatry, 63(1):57-62. Assay of prognostic biomarkers in a sample from a subject are also useful in prognosis or diagnosis of a chronic neurodegenerative condition. For example, where the chronic neurodegenerative condition is Alzheimer's disease, prognostic biomarkers include, but are not limited to, total tau protein, phospho-tau protein, $\beta$-amyloid$_r$.4$_2$ peptide, $\beta$-amyloidi-$_{40}$ peptide, complement component 1, q subcomponent (C1q) protein, interleukin 6 (IL-6) protein, apolipoprotein E (APOE) protein, o-1-antichymo trypsin protein, oxysterol (e.g., 24S-hydroxycholesterol), isoprostane (e.g., an F2-isoprostane), 3-nitrotyrosine, homocysteine, or cholesterol, or any combination thereof, e.g., the ratio of $\beta$-amyloidi.42 peptide to $\beta$-amyloidt.40 peptide.

Psycho-Pharmacological Functional Activity

The functional pharmacological activity of a growth factor modulating selective Sigma 1 or Dopamine D3 receptor agonist or a 5HT$_{2c}$ receptor ligand, such as Captodiamine, or a pharmaceutically acceptable salt thereof or mixtures thereof at a given receptor can be achieved by a variety of in-vitro methodologies. A currently favored assay is the Receptor Selection and Amplification Technology (R-SAT) assay disclosed in U.S. Pat. No. 5,707,798, the content of which is hereby incorporated by reference in its entirety. Another currently favored assay is the PI Hydrolysis assay (see, for example, the description of the PI Hydrolysis assay in Barker et al (1994) J Biol Chem 269 (16); 11687-11690. Defining the ability of a growth factor modulating selective Sigma 1 or Dopamine D3 receptor agonist or a 5HT$_{2c}$ receptor ligand, such as Captodiamine, or a pharmaceutically acceptable salt thereof or mixtures thereof to penetrate the blood brain barrier and elicit a meaningful biological response can be achieved by a variety of methodologies. A currently favored assay is the hippocampal MAP kinase activation assay.

The suitability of any particular growth factor modulating selective Sigma 1 or Dopamine D3 receptor agonist or a 5HT$_{2c}$ receptor ligand, such as Captodiamine, or a pharmaceutically acceptable salt thereof or mixtures thereof can be readily determined by evaluation of its potency and selectivity using literature methods followed by evaluation of various pharmacological studies which include but are not limited toxicity, absorption, distribution, metabolism, excretion (ADME) and pharmacokinetic studies which are carried out in accordance with standard pharmaceutical practice.

Selectivity ratios may readily be determined by the skilled person in the art. For some applications, preferably a growth factor modulating selective Sigma 1 or Dopamine D3 receptor agonist or a 5HT$_{2c}$ receptor ligand, such as Captodiamine, or a pharmaceutically acceptable salt thereof or mixtures thereof has at least about a 25, 50, 75, 100 fold selectivity for the desired target, preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

Receptor affinity is a good starting point for determining the mechanism of a particular compound. Receptor affinity may readily be determined by the skilled person in the art. For most applications, preferably the growth factor modulating selective Sigma 1 or Dopamine D3 receptor agonist or a 5HT$_2$, receptor ligand, such as Captodiamine, or a pharmaceutically acceptable salt thereof or mixtures thereof has an affinity, such as a preferential binding affinity, for its target of at least $10^{-7}$M, preferably $10^{-8}$M, preferably $10^{-9}$M.

In this regard, IC50 values and EC50 values for any particular growth factor modulating selective Sigma 1 or Dopamine D3 receptor agonist or a 5HT$_2$. receptor ligand, such as Captodiamine, or a pharmaceutically acceptable salt thereof or mixtures thereof may be determined using established literature methodology.

As used herein, the term "IC50" means the concentration of drug that is required to inhibit the action, binding, or activity of some other drug by 50%.

As used herein, the term "EC50" is the dosage at which the desired response is present for 50 percent of the population. It is commonly used as a measure of drug potency.

For some applications, preferably the growth factor modulating selective Sigma 1 or Dopamine D3 receptor agonist or a 5HT$_{2c}$ receptor ligand, such as Captodiamine, or a pharmaceutically acceptable salt thereof or mixtures thereof has an EC50 value of less than 300 nM, 250 nM, 200 nM, 150 nM, preferably less than about 100 nM, preferably less than about 75 nM, preferably less than about 50 nM, preferably less than about 25 nM, preferably less than about 20 nM, preferably less than about 15 nM, preferably less than about 10 nM, preferably less than about 5 nM.

Animal Models

In vivo models may be used to investigate and/or design therapies and/or therapeutic agents to treat symptoms of anxiety and/or depression associated with an "affective" disorder; and/or symptoms associated with a cognitive impairment disorder in a subject in need of same. The models could be used to investigate the effect of various tools/lead compounds on a variety of parameters which indicate the psycho-pharmacological behavioural response as defined, for example, in any one or more of the above described psycho-pharmacological tests.

The invention further provides transgenic nonhuman animals capable of expressing a nucleotide sequence encoding, for example, a specific protein linked with symptoms of anxiety and/or depression associated with an "affective" disorder; and/or symptoms associated with a cognitive impairment disorder in a subject in need of same. By way of example, it has recently been shown that genetic variation in the ABCB 1 gene can account for some of the differences in antidepressant efficacy (See Nature Review Drug Discovery, published online 15 Feb. 2008; doi10.1038/nrd2535 and Uhr M et al "polymorphisms in the drug transport gene ABCB1 predict antidepressant response in depression (2008) Neuron 57: 203-209). In addition, transport molecules on the endothelial cells that line cerebral capillaries, such as P-glycoprotein (P-gp; encoded by ABCB1) determine the intracerebral concentration of certain drugs and thus, could be critical for the clinical response of Central Nervous System (CNS) targeted drugs.

Expression of such a nucleotide sequence is usually achieved by operably linking the nucleotide sequence to a promoter and optionally an enhancer, and microinjecting the construct into a zygote. See Hogan et al., "Manipulating the Mouse Embryo, A Laboratory Manual," Cold Spring Harbor Laboratory. Inactivation of such a nucleotide sequence may be achieved by forming a transgene in which a cloned nucleotide sequence is inactivated by insertion of a positive selection marker. See, for example, Capecchi, Science 244, 1288-1292 (1989). The transgene is then introduced into an embryonic stem cell, where it undergoes homologous recombination with an endogenous variant gene. Mice and other rodents are preferred animals. Such animals provide screens and/or screening systems for identifying compounds capable of modulating the psycho-pharmacological behavioural response, as defined, for example, in any one or more of the above described psycho-pharmacological tests.

Testing in Humans

Preferred combinations of (1) a growth factor modulating selective Sigma 1 or Dopamine D3 receptor agonist or a $5HT_{2c}$ receptor ligand, such as Captodiamine, or a pharmaceutically acceptable salt thereof or mixtures thereof; and (2) one or more of an anti-depressant agent; (ii) an anxiolytic; and (iii) a cognitive enhancing agent useful herein can also be tested clinically, typically orally, in humans as well as in an animal model. Each component is administered singly at different times to a population of human subjects, each component being administered in an amount which produces little or no response, typically less than a 50% response. By administering each component singly, it is meant that one component is administered, followed at a later time by the second component after having allowed an appropriate time for washout of the first component. After the washout period for each component administered singly, the components are co-administered in a manner such that both components co-operate pharmacokinetically, preferably such that the peak pharmacokinetic effect due to each coincides. Co-administration is evaluated according to the parameters mentioned above and by questionnaires, thereby providing a basis for comparison of the effects of co-administration with that for each single administration.

BRIEF DESCRIPTION OF THE FIGURES

The invention is now further described only by way of example in which reference is made to the following Figures.

EXAMPLES

The following Examples are provided to illustrate but not to limit the invention.

Captodiamine

The drug with the IUPAC classification of 2-[(4-butylsulfanylphenyl)-phenyl-methyl]sulfanyl-N,N-dimethyl-ethanamin, is known under the non-proprietary name, Captodiamine, was taken as representative of the compounds described herein.

The chemical formula for Captodiamine is $C_{21}H_{29}NS_2$ and its CAS number is 486-17-9. The compound is also known under the following synonyms: 2-[(p-(Butylthio)-alpha-phenylbenzyl)thio)-N,N-dimethylethylamine, 4-06-00-06672 (Beilstein Handbook Reference), 486-17-9, BRN 2625367, Captodiame, Captodiamin, Captodiamine, Captodiamo [INN-Spanish], Captodiamum [INN-Latin], Captodramin, Captodramine, Covatin, Covatix, EINECS 207-629-1, Ethanamine, 24(4-(butylthio)phenyl)phenylmethyl)thio)-N,N-dimethyl-(9CI), Ethanamine, 2-[[[4-(butylthio)phenyl]phenylmethyl]thio]-N,N-dimethyl-, ETHYLAMINE, 2-[(p-(BUTYLTHIO)-alpha-PHENYLBENZYL)THIO)-N,N-DIMETHYL-, Kaptodiamin [Czech], N 68, p-Butylmercaptobenzhydryl-beta-dimethylamino-ethylsulphide, VUFB2350

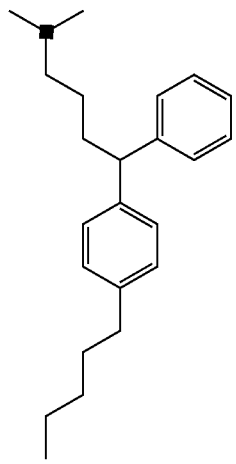 [SMILES: CCCCCc1ccc(C(CCCC(C)C)c2ccccc2)cc1]

Captodiamine

Experimental protocol employed in the behavioural evaluation of Captodiamine.

Example 1

Materials and Methods I

Figure 7:
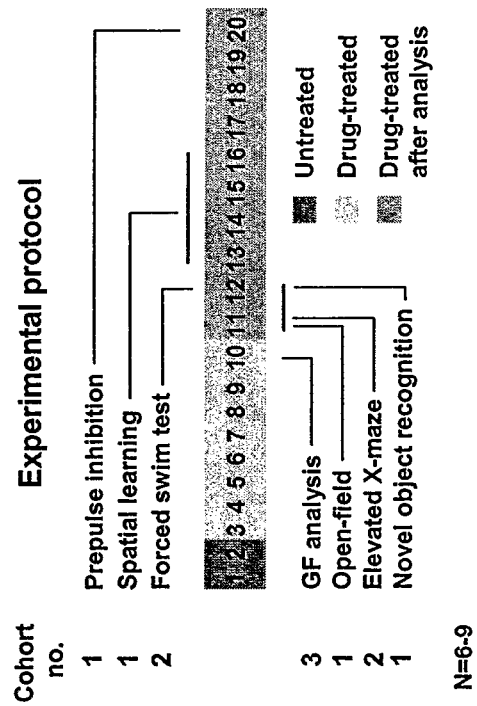
FIG. 7 provides a schematic diagram which shows the experimental protocol employed in the behavioural evaluation of Captodiamine.
Figure 8:
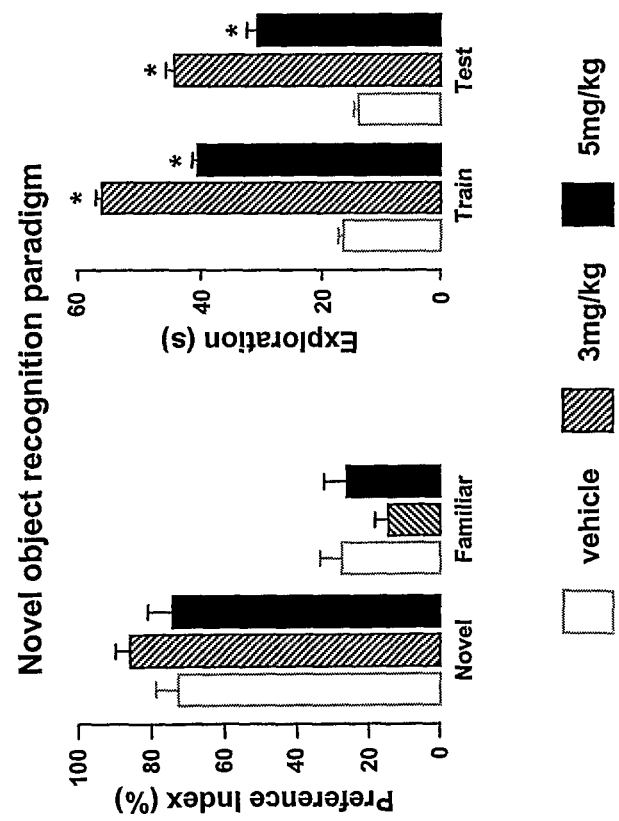
FIG. 8 provides graphs which show the influence of Captodiamine during the Novel Object Recognition (NOR) test in mice. During the training phase (day 1), animals are presented with two identical objects, and the % exploratory time spent at each object computed as a preference index (PI). During the recall or testing phase, on day 2, a novel object and familiar object are presented with a bias for the novel object expected (left hand panel). Captodiamine treated animals also spend more time exploring objects in both the training (day 1) and testing phases (day 2) (right hand panel)

The Experimental protocol employed in the behavioural evaluation of Captodiamine is outlined in FIG. 7. Two separate cohorts of C57B16 mice were employed. Cohort 1 was used to evaluate the drug effect on prepulse inhibition, open-field and novel object recognition and spatial learning. Cohort 2 was used to evaluate drug effects on the Forced Swim Test and the Elevated X-Maze test. The behavioural tests were administered in sequence as per day number indicated in the bar. The drug was administered by the intraperitoneal route and on the day of training the drug was administered after the behavioural analysis. Captodiamine/UCD-0620 was administered at doses of 3 and 5 mg/kg. The compound was administered once daily, via the intraperitoneal route, for 7 days prior to testing and the animals were drug-free at time of training.

Psycho-Pharmacological Tests

Neurobehavioural Screening Methods

A modified SHIRPA protocol was adopted in order to provide an in vivo drug profile. The SHIRPA protocol is used in both academic and industrial environments for an initial behavioural characterisation of potential psychopharmaceuticals. The first behavioural tier analysis of our modified screen comprised open-field, novel object recognition (NOR), elevated X-maze (XM), and pre-pulse inhibition (PPI) paradigms (FIGS. 3 to 5 and 8). These psycho-pharmacological tests are described in more detail below:

First Behavioural Tier Analysis

Open Field Analysis—Potential Anxiolytic Behaviour

Open-field analysis was used to indicate drug effects on locomotion, grooming and rearing activities. Furthermore, by determining how much time is spent in the centre of the open-field potential anxiolytic-like behaviour could be identified.

Novel Object Recognition (NOR)

Novel object recognition was used to assess drug influence on visual recognition memory and attention. It is also useful in evaluating the role of experimental manipulation on cognition.

Pre-Pulse Inhibition—Sensory Processing (Working Memory)

Pre-pulse inhibition was used to evaluate drug effects on sensory processing, a form of working memory.

Second Behavioural Tier Analysis

Elevated X-maze (XM)—Potential Anxiolytic Activity

This determines potential anxiolytic (elevated X-maze; XM) activity. The elevated X-maze determines the time spent in the unprotected elevated arm of the maze.

Forced Swim Test (FST)—Potential Antidepressant

This determines potential antidepressant (forced swim test; FST) actions. The forced swim tests the time spent immobile as a measure of despair.

Third Behavioural Tier Analysis Phase

Water Maze Spatial Learning

Finally, drugs inducing neurobehavioural profile are evaluated in the water maze spatial learning paradigm, a robust task of information acquisition and consolidation—a measure of pro-cognitive action.

Captodiamine

Materials and Methods I

The Experimental protocol employed in the behavioural evaluation of Captodiamine is set out as follows: Three separate cohorts of C57B16 mice were employed in the behavioural evaluation of Captodiamine (see FIG. 7). Cohort 1 was used to evaluate the drug effect on prepulse inhibition, spatial learning, open-field and novel object recognition. Cohort 2 was used to evaluate drug effects on the forced swim test and the elevated X-maze. The behavioural tests were administered in sequence as per day number indicated in the bar of FIG. 7. The drug was administered by the intraperitoneal route and on the day of training the drug was administered after the behavioural analysis. Cohort 3 was used for analysis of growth factor (GF) expression (such as, for example, Brain Derived Neurotrophic Factor (BDNF and Glial Derived Neurotrophic Factor (GDNF). The brains were removed immediately after sacrifice, the relevant brain areas dissected, homogenised and stored at −80° C. until analysis. Captodiamine/UCD-0620 was administered at doses of 3 and 5 mg/kg. The compound was administered once daily, via the intraperitoneal route, for 7 days prior to testing and the animals were drug-free at time of training.

Materials and Methods II

Figure 6:
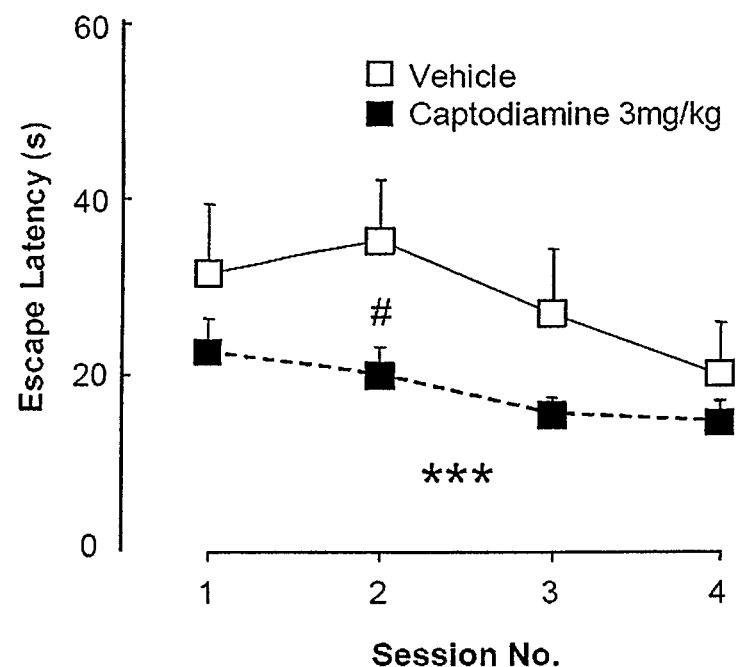
FIG. 6 is a graph which shows the performance of Captodiamine treated animals in the water maze. The water maze is used as a test of spatial memory and cognitive function. In it, animals learn the location of a hidden platform in a circular pool of water. Multiple sessions of training in the water maze are directed at detecting drug effects on behaviour and cognition across many trials of the paradigm.
Figure 6:
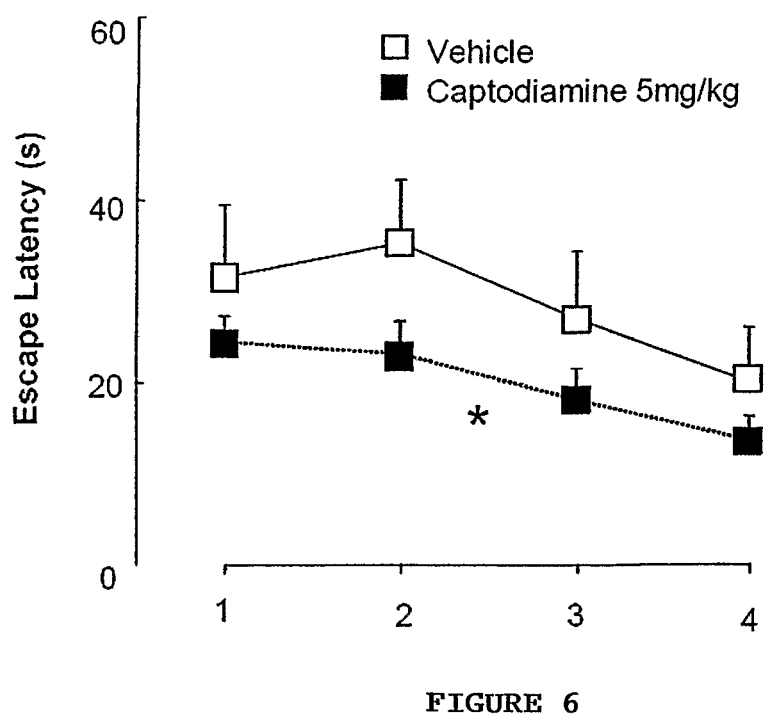

The influence of Captodiamine on open-field behaviour (FIG. 3), novel object recognition (FIG. 8), forced swim test (FIGS. 10A and 10B) and water maze spatial learning (FIG. 6). Captodiamine was administered by the intraperitoneal route at the doses indicated and as per details outlined in FIG. 7. Values were analysed using a two way ANOVA and Student t-test and those with a p values<0.05 were accepted as significant and where appropriate are indicated with an asterisk.

Materials and Methods III

The Structure (FIG. 9A), receptor affinity (FIG. 9B), pharmacokinetics (FIG. 9C) and growth factor modulation (FIG. 9D) of Captodiamine are provided. Analysis of receptor affinities was performed by Novascreen™ and those displacing >20% of the natural ligand are indicated by the filled boxes. Blood levels of Captodiamine were determined by GC mass spectroscopy. In separate samples taken from a cannulated jugular at increasing time intervals following a single intraperitoneal injection of tha drug (5 mg/kg). Growth factor analysis was performed using tissue homogenates and ELISA assays specific for each growth factor (Promega). Values were analysed using a Student t-test and those with a p value<0.05 were accepted as significant and are indicated with an asterisk.

Intravenous Administration/Multiple Time Point Procedure for Rats

This protocol employs a traditional pharmacokinetic approach. Groups of animals are dosed with the compound of interest, blood samples are obtained, and animals are sacrificed at predetermined times for brain tissue analysis.

NOTE: This procedure involves rodent survival surgery. Sterile surgical procedures must be employed, as specified by prevailing animal care regulations. All surgical instruments and consumable items used for surgery must be sterile.

Pharmacokinetics

A. Prepare Rat for Surgery

1. Anesthetize a 200- to 350-g laboratory rat with an appropriate anesthetic to maintain proper anesthesia for a surgical procedure of ≦1 hr.
2. Administer appropriate antibiotic to the animal.
3. Place anesthetized rat right side up (lying on its belly) on a warming pad. Shave the fur from its back, between the shoulder blades, using an animal fur shaver. Clean the surgical area with an iodine solution. Using a pair of 4.5-in. operating scissors, make a small incision (0.3 cm long) between or slightly ahead of the shoulder blades.
4. Reposition the rat so that it is upside down (lying on its back) on the warming pad with its head located towards the surgeon and its tail away from the surgeon.
5. Shave the fur from its neck and shoulder areas. Wash surgical area with an iodine solution and cover area with sterile drapes, leaving only the surgical site exposed.

B. Perform Surgery

6. Using a scalpel, make a 2- to 3-cm-long incision over the skin site where pulsation of the right jugular vein can be observed.
7. Using a pair of 4-in. full or strongly curved microdissecting forceps, bluntly separate the subcutaneous and muscle tissues to expose a section of the jugular vein.
8. Using the forceps, carefully clean the vessel of connective tissue from the point of the chest muscle penetration (towards the heart) to a point where it bifurcates into two smaller vessels.
9. Using a sterile 4.0 suture without needle, ligate the vein shut at the point of the bifurcation (towards the snout).
10. Subcutaneously tunnel a 6-in. eye probe from the incision in the back (between the shoulder blades) to the incision in the neck and shoulder area. Insert a jugular vein catheter into the eye of the probe. Pull the probe out so that the catheter is subcutaneously tunneled under the skin, such that the catheter end extends out from the incision on the back and the silastic tubing end extends from the jugular vein incision.
11. Position the catheter so that it lies comfortably in the jugular vein incision site. Cut the silastic tubing such that the free end is <0.5 cm short of the midline of the front paws and the silastic-PESO junction rests over the jugular vein. Make a beveled cut at the end of the silastic tubing.
12. Connect the PESO tubing of the catheter to a 22-G hypodermic needle with the beveled end cut off, affixed to a 3-ml syringe containing prewarmed sterile saline. Fill the catheter with sterile saline.
13. Place two or three more pieces of 4.0 suture under the jugular vein, towards the heart. These pieces will be used to secure the catheter in the vein once the catheter is properly positioned.
14. Using a pair of 3-in. Vannas spring scissors, make a small, nicking incision in the jugular vein. Be careful not to cut through the vein.
15. Insert one point of a pair of Dumont no. 7 microdissecting forceps into the jugular vein incision. Slide the beveled end of the catheter along the probe into the incision. Continue inserting and guiding the catheter into the vein until the cut end of the vein covers the juncture of the silastic and PESO tubing.
16. To test for catheter patency, inject 0.3 ml sterile saline and then slowly pull back on the syringe plunger to withdraw blood.
17. Clear the catheter of blood by flushing with 0.5 ml sterile saline.
18. Anchor the catheter to the vein by tying the 4.0 sutures (step 13) securely (but not too tightly) around the vein and the PESO tubing.
19. Suture the catheter to the muscle bed using a 5.5-in. Olsen-Hegar needle holder and sterile 4.0 suture with needle.
20. Close the internal incision by suturing the muscle and subcutaneous tissues with 4.0 sutures.
21. Close the skin incision using a sterile 2.0 suture with needle.
22. Place anesthetized animal right side up (on its belly). Suture the exteriorized catheter to the skin and then close the incision on the back using 2.0 suture.

23. Trim the exteriorized PE50 tubing so that no more than 2.5 to 3 cm is exposed. Plug the open end of the catheter with a sterile piece of 22-G stainless steel wire.
24. Apply topical antibiotics to all incision sites and allow animal to recover from the anesthetic using approved postoperative care protocols.
25. Slowly flush the jugular vein catheter with 0.5 to 1.0 ml sterile 10 U/ml heparinized saline each day to maintain patency.

At least 7 Days are allowed to elapse between the surgery and experimental study.

C. Prepare Experimental Equipment

26. Label an appropriate number of 1.5-ml microcentrifuge tubes with caps for the number of desired blood samples per rat.
27. Fill a 1-, 3-, or 5-ml syringe (depending on the dosing volume) with prewarmed test compound solution for each animal to be studied. To each syringe attach a 22-G hypodermic needle with the beveled end cut off. Keep the syringe and its contents warm by wrapping it in a preheated warming pad.
28. Prepare an appropriate number of 1-ml syringes filled with 1 ml prewarmed sterile saline.
29. Prepare an appropriate number of empty 1-ml syringes for blood collection.

D. Perform Experimental Study

30. Transfer the catheterized rat to an appropriate animal holding cage.
31. Connect one end of a 20-cm-long piece of PE50 tubing to a 1-ml saline-filled syringe using a 22-G hypodermic needle with the beveled end cut off. Fill tubing with sterile saline and connect the free end of the saline-filled PE50 tubing to the exteriorized jugular vein catheter using a 22-G stainless steel connector. Gently flush catheter with 0.3 ml saline.
32. Withdraw a predose blood sample (blank; time zero) by gently pulling back the syringe plunger so that the luer-lock needle hub is filled with blood. Attach a fresh syringe (step 30) to the luer-lock hub and collect a 0.1- to 0.15-ml blood sample.
35. Remove the sample syringe, transfer sample to the prepared vial (step 27), and reattach the first syringe (filled with saline and possibly mixed with blood) to the needle hub. Flush the PE50 line and refill it with 0.3 to 0.5 ml sterile saline. Replace the initial syringe with a fresh syringe containing sterile saline.
36. Attach the test compound dosing syringe (step 28) to the PE50 tubing. Administer the dose intravenously over 30 to 60 sec. Remove the dosing syringe and attach a saline-filled syringe to the PE50 line. Flush the residual dose intravenously with saline and refill the tubing with sterile saline. Retain a 0.25-ml aliquot of the test compound solution for later analysis.
37. Withdraw blood samples at predetermined time intervals.
38. Withdraw the last blood sample from about 30 to 60 sec before sacrifice, quickly anesthetize the rat, and decapitate it.

Materials and Methods IV

Influence of Captodiamine on the Rat Pyloric Region

Inhibition of pyloric relaxation by administration of captodiamine was performed as described in Kashyap P., Micci M., Pasricha S., Pasricha P., The D2/D3 Agonist PD 128907 (R-(+)-trans-3,4a,10b-Tetrahydro-4-Propyl-2H,5H-[1]Benzopyrano[4,3-b]-1,4-Oxazin-9-ol) Inhibits Stimulated Pyloric Relaxation and Spontaneous Gastric Emptying, 2007, Digestive Diseases and Sciences.

Male Wistar rats were killed by cervical dislocation and decapitation. The stomach was removed and placed in oxygenated Krebs buffer (118 mM NaCl, 4.7 mM KCl, 1.2 mM $KH_2PO_4$, 1.2 mM $MgSO_4$, 4.2 mM $NaHCO_3$, 2 mM $CaCl_2$, 10 mM glucose, 200 µM sulphinpyrazone and 10 mM Hepes, pH 7.4). The pyloric region was dissected by cutting the stomach superior to the antral pyloric border and the remaining mesenteric and duodenal tissue was removed. The tissue was cut longitudinally along the mesenteric border and trimmed to 2 mm in width. At one end, the tissue was mounted onto an L-shaped electrode and placed into a 25 ml chamber containing Krebs buffer, maintained at 37° C. and continuously bubbled with 95% $O_2$/5% $CO_2$. The other end of the tissue was attached to an isometric force transducer using string sutured to tissue. Tension was monitored, recorded and analyzed by a digital recording device (PowerLab and Chart 5, ADInstruments). The tissue was allowed to equilibrate under tension (1 g) for 60 min and the buffer was changed intermittently. Spontaneous contraction of the pyloric strips were observed and recorded following the equilibration phase. Electrical field stimulation (90 V, 2-16 Hz, 1-ms pulse for duration of 1 min) was applied at which time relaxation of the tissue was observed (FIG. 1A). The tissue was treated for 10 min with varying concentrations of captodiamine (10 µM-100 µM), at which stage relaxation was attenuated (FIG. 1B). The strips were washed with Krebs buffer between the different doses. Maximal tissue contraction was induced by treating with Krebs buffer with KCl at the end of the experiment. The weight of the tissue was measured at the end of each session.

Discussion of Results I and II

Figure 3:
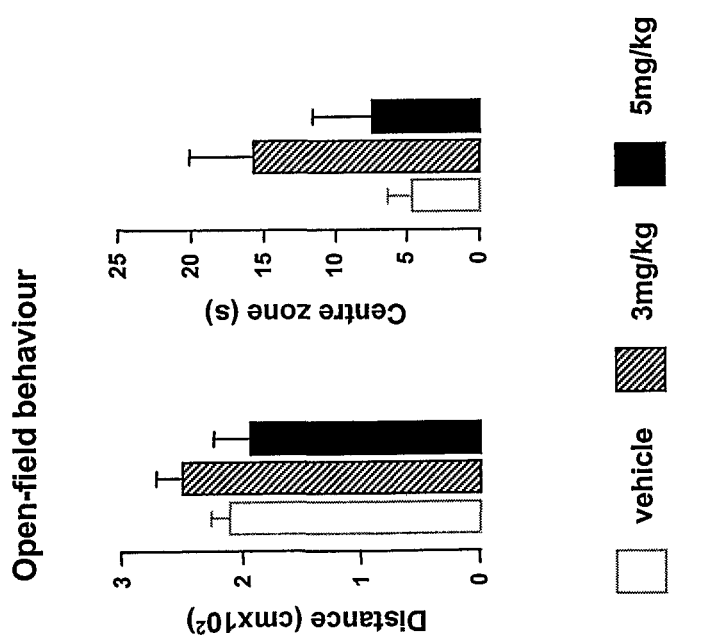
FIG. 3 is a graph which shows the influence of Captodiamine (3 mg/kg and 5 mg/kg) on locomotor activity and the amount of time spent in the centre of the open-field arena.
Figure 4:
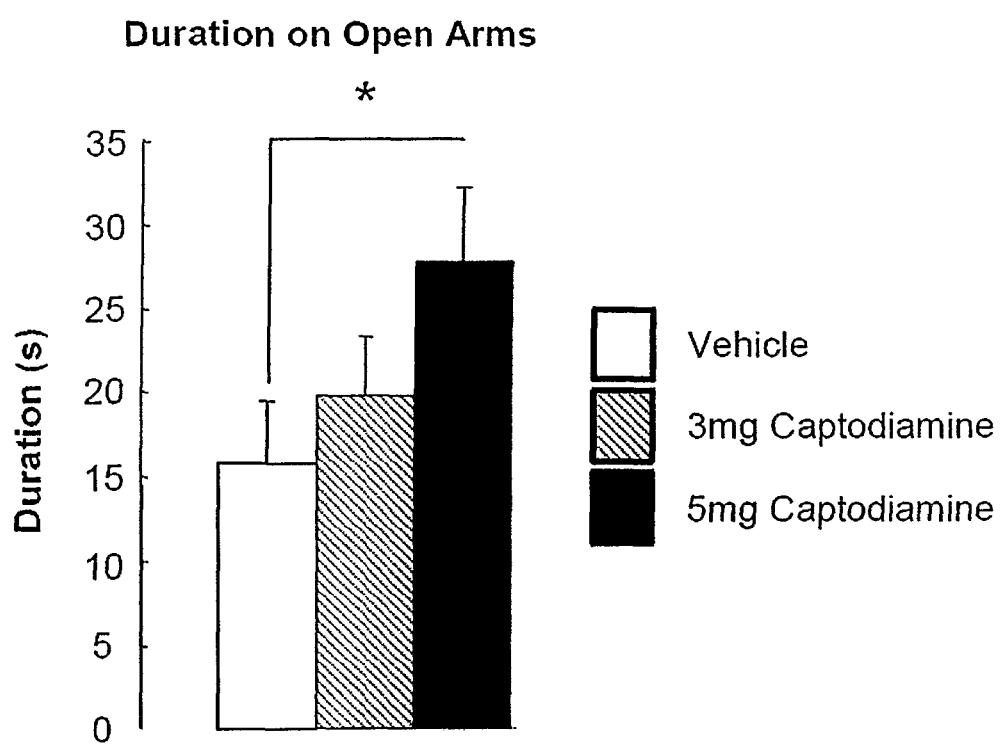
FIG. 4 is a graph which shows the influence of Captodiamine (3 mg/kg and 5 mg/kg) in the elevated X-Maze. The elevated X-maze has strong claims to validity as an animal model of anxiety and is of great utility in evaluating putative anxiety modulating drugs. The test is based on rodents' natural fear of heights and open spaces. The apparatus consists of 4 raised flat runways extending from a central platform, two enclosed, two exposed. The time spent exploring the exposed arms of the maze is inversely related to the level of stress/anxiety felt by the animal.
Figure 5:
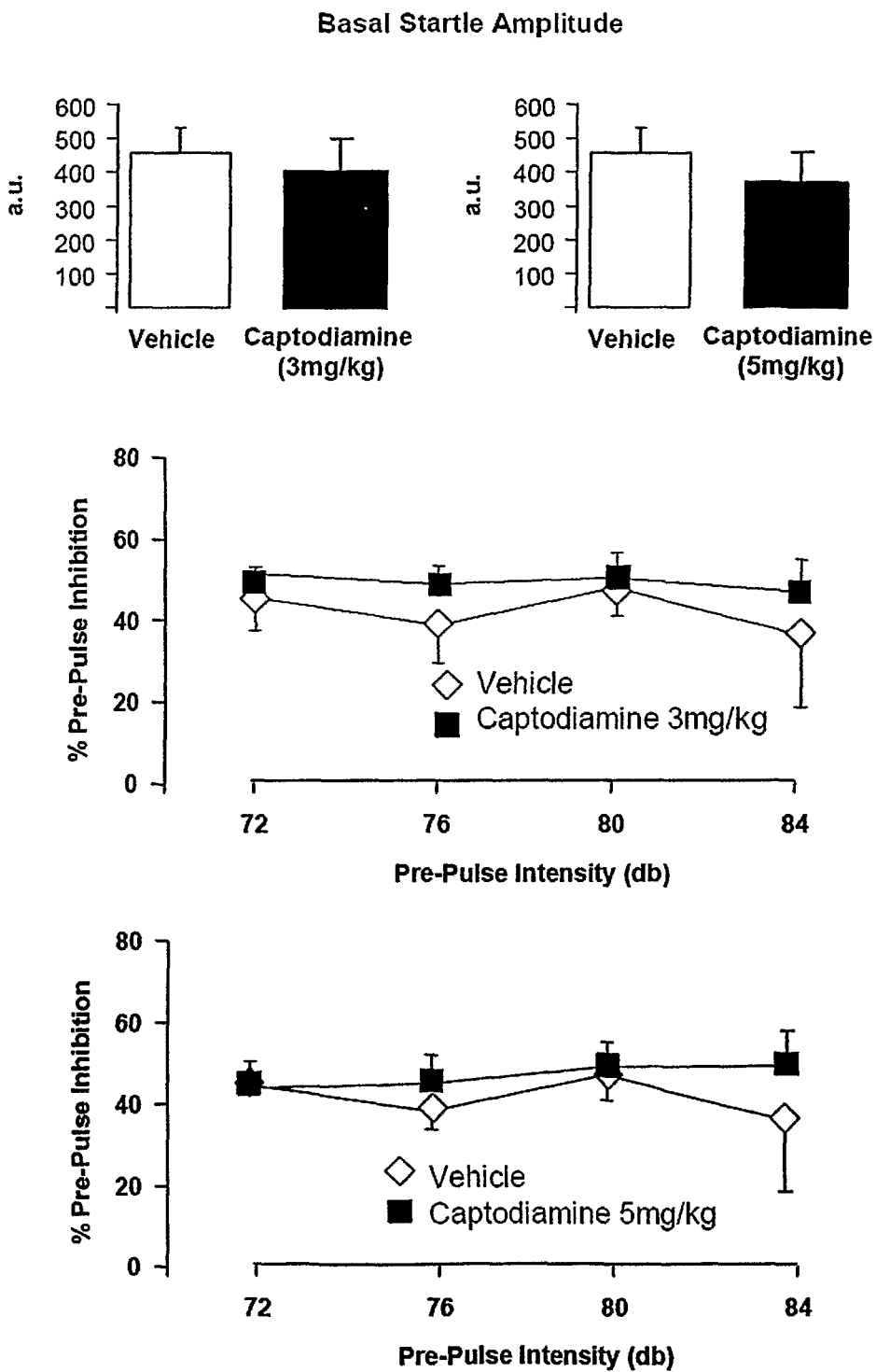
FIG. 5 is a graph which shows the influence of Captodiamine on pre-pulse inhibition (PPI) of the startle response. The startle response is the contraction of the whole-body musculature in response to a sudden, loud noise. The magnitude of the response can be reduced when preceded by a weak noise (pre-pulse). This reduction or inhibition of startle is not observed in patients, such as schizophrenic patients.

Captodiamine had no influence on basal locomotion in the open-field paradigm (FIG. 3). However, animals tended to spend significantly more time in the centre of the centre of the arena, suggesting that Captodiamine exerts an anxiolytic action. This anxiolytic action was confirmed using the elevated X-maze in which the treated animal spent a significantly longer periods exploring the open arms of the maze (FIG. 4).

Figure 10A:
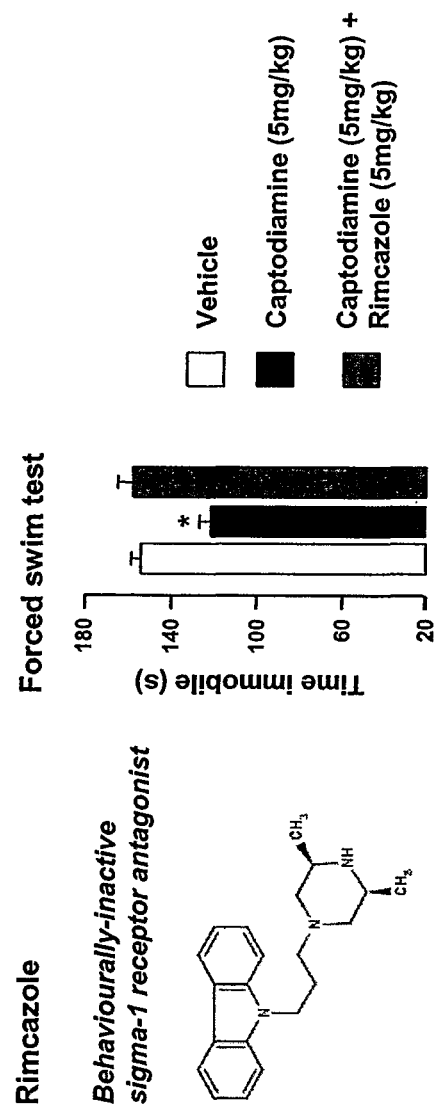
FIG. 10A is a graph which shows the influence of a combination of Captodiamine and Rimcazole (a Sigma-1 receptor antagonist) on behavioural activity in the Forced Swim Test.
Figure 10B:
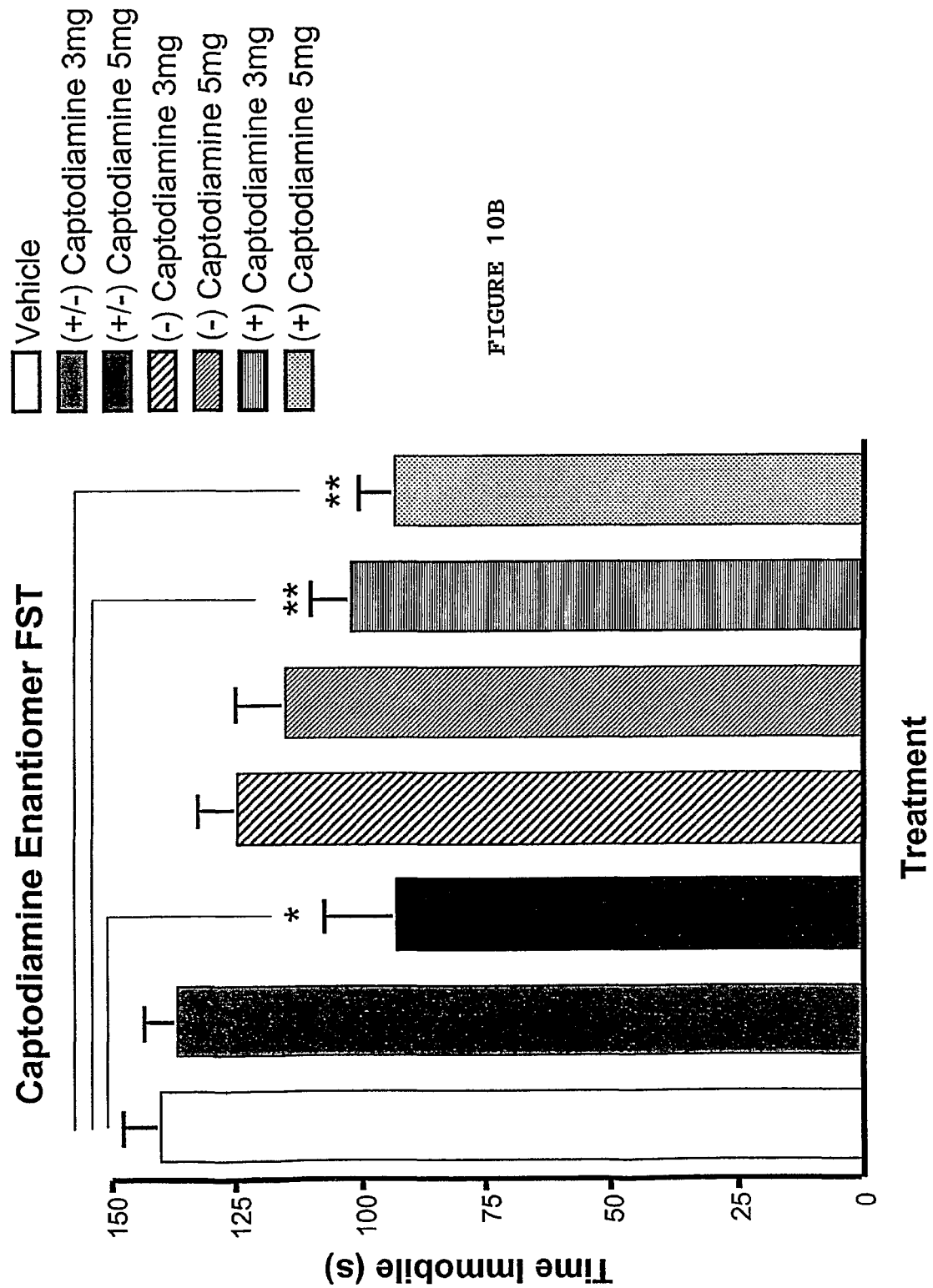
FIG. 10B shows the influence of racemic Captodiamine (+/−), dextrorotary Captodiamine (+) and levorotary Captodiamine (−) at concentrations of 3 mg/kg and 5 mg/kg on the duration of time spent immobile during the forced swim test. Values are expressed as mean±S.E.M (n=8). Statistical difference was determined using a Mann Whitney non-parametric U-test. Values significant at p<0.05 are denoted by a single asterisk and p values<0.005 are denoted by a double asterisk.
Figure 11:
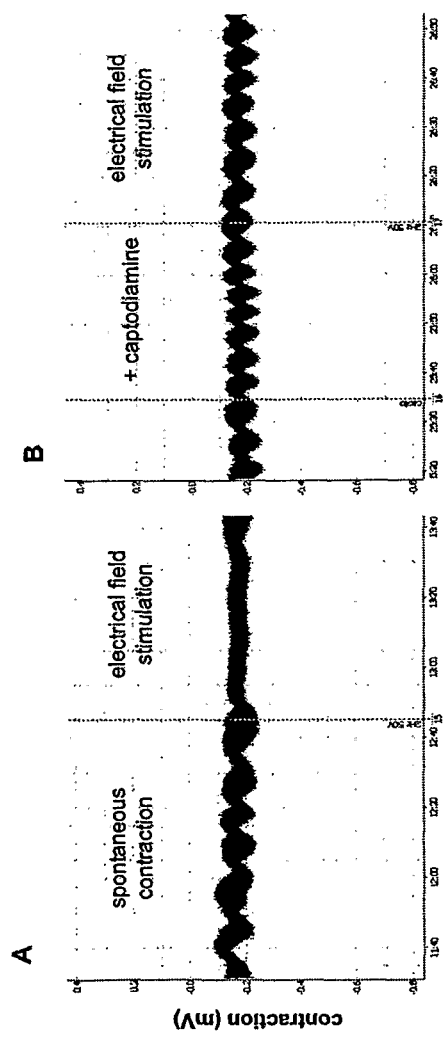
FIG. 11 shows the response of pyloric contractility to captodiamine. Panel (A) demonstrates the electrical field stimulation (EFS)-mediated relaxation of the rat pyloric muscle. Panel (B) demonstrates attenuation of the EFS-mediatated relaxation by addition of 25 μM Captodiamine.
Figure 12:
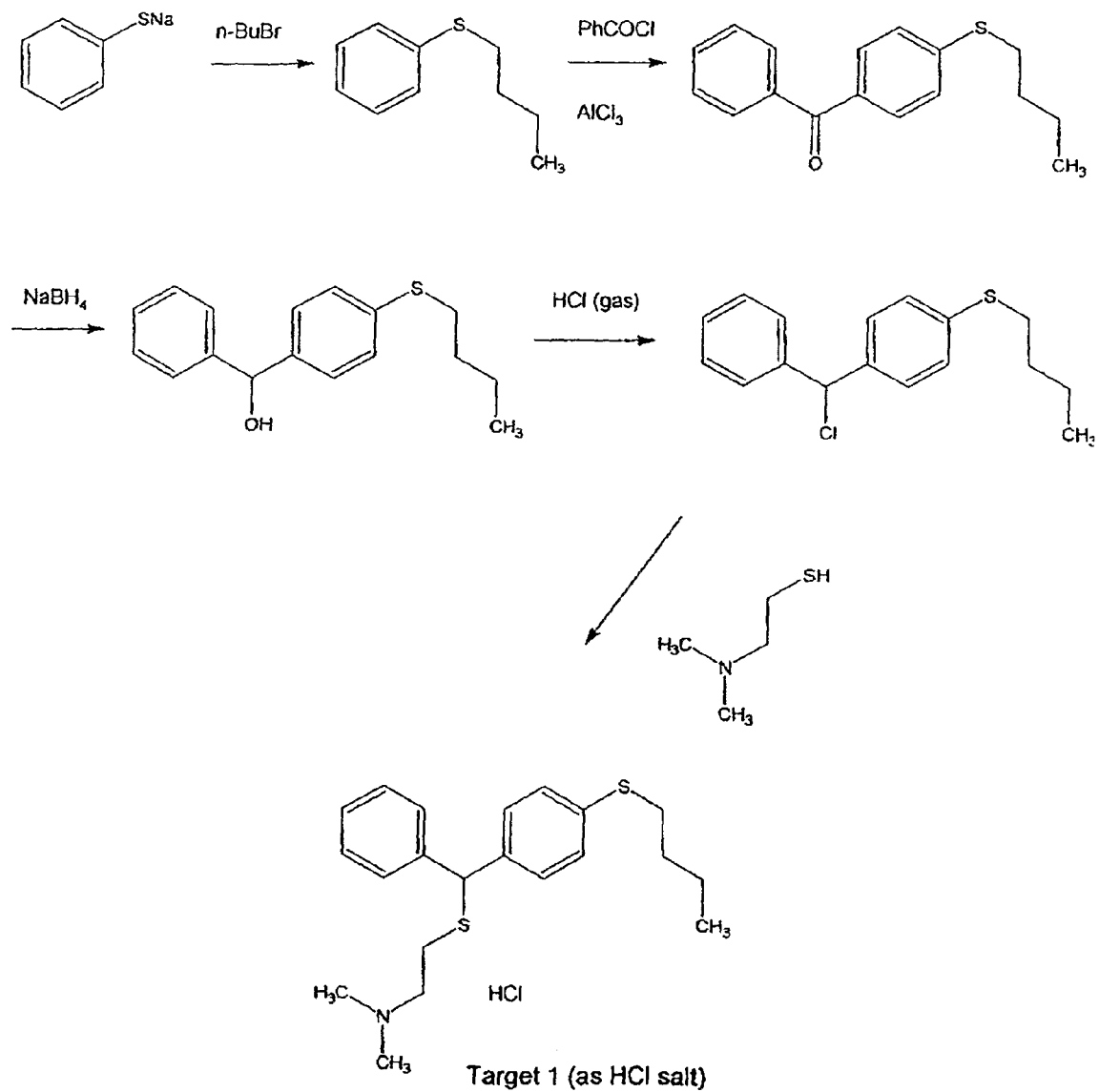
FIG. 12 shows a method of making Captodiamine.

Captodiamine exhibited no effect on the pre-pulse inhibition paradigm (FIG. 5) clearly demonstrating it to have little or no effect on mechanisms of sensory processing. In contrast, Captodiamine treated animals, at the 3 mg/kg dose, spent significantly longer investigating objects during the training phase, as measured by the one-tailed t-test in the Novel Object Recognition Task (FIG. 10B). Captodiamine was also further differentiated by its significant pro-cognitive action in the water maze spatial learning task (FIG. 6). The marked anxiolytic action of Captodiamine also prompted a determination of its potential as an antidepressant. This action was confirmed by the significant increase on time to immobility that was observed in the forced swim test (FIGS. 10A and 10B). The combined effect of Captodiamine on openfield behaviour and performance in the elevated X-maze suggests it to have anxiolytic actions that most likely contribute to its procognitive actions in water maze spatial paradigm and antidepressant actions in the forced swim test.

Results III—Receptor Affinity and Pharmacokinetics for Captodiamine

Figure 9:
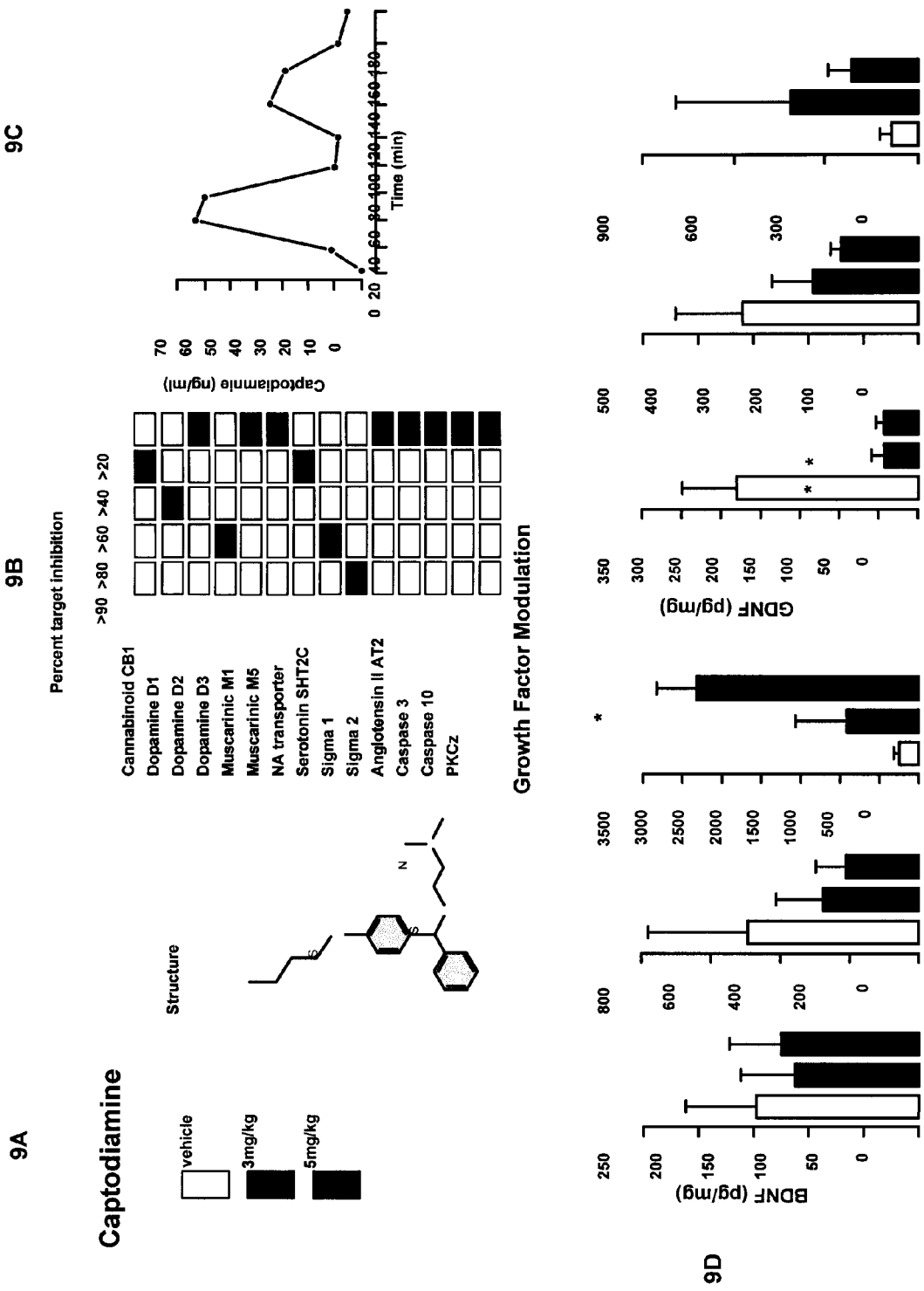
FIG. 9A displays the two dimensional chemical structure of Captodiamine.
FIG. 9B displays the top ranking receptors for which Captodiamine displayed affinity. Affinities were determined by having a 1 μM concentration of Captodiamine compete for receptor binding with a reference ligand (a compound with a known affinity for the receptor in question). The amount of reference ligand that is prevented from binding to a particular receptor is measured and this gives rise to the "percent target inhibition" value that is displayed in this panel.
FIG. 9C displays the pharmacokinetic data for Captodiamine. This panel displays the blood concentration of the drug (in ng/ml) at increasing time points (the time points were 20 mins apart) following a single injection of the compound at a dose of 5 mg/kg into the intraperitoneal cavity. The drug concentration in the blood samples was determined using GC mass spectroscopy.
FIG. 9D displays the effect that a sub-chronic (7 day treatment of injection per day) administration of Captodiamine has on the levels of neurotrophic factors BDNF (Brain-derived neurotrophic factor) and GDNF (Glial cell derived neurotrophic factor) in three particular brain regions—the prefrontal cortex, the hippocampus and the hypothalamus. Neurotrophic factor concentration was determined by using an ELISA purchased from Promega Inc.

FIG. 9B displays the top ranking receptors for which Captodiamine displayed affinity. Affinities were determined by allowing a 1 µM concentration of Captodiamine compete for receptor binding with a reference ligand (a compound with a known affinity for the receptor in question). The amount of reference ligand that is prevented from binding to a particular receptor is measured and this gives rise to the "percent target inhibition" value that is displayed in FIG. 9B. The higher the target inhibition value, the greater the affinity Captodiamine has for this particular receptor as it displaces a greater proportion of the reference ligand. This assay is an automated high throughput assay performed on cell lines that express only one type of receptor and was carried out by Novascreen (www.novascreen.com). Receptor affinity is a good starting point for determining the mechanism of action for a particular compound. In this case a greater than 90% inhibition value for the Sigma 1 receptor and the greater than 80% inhibition value for the dopamine D3 and serotonin $5HT_{2c}$ receptor would suggest that the effects of Captodiamine are predominantly mediated through these receptors. In contrast, Captodiamine only demonstrates a greater than 20% inhibition value for the Sigma 2 receptor Both the Dopamine D3 receptor and the $5HT_{2c}$ receptor show a greater than 80% inhibition value, demonstrating that some of the effects of Captodiamine are mediated through these receptors.

FIG. 9C displays the pharmacokinetic data for Captodiamine. This panel displays the blood concentration of the drug (in ng/ml) at increasing time points (the time points were 20 mins apart) following a single injection of the compound at a dose of 5 mg/kg into the intraperitoneal cavity. The drug concentration in the blood samples was determined using GC mass spectroscopy;

FIG. 9D displays the effect that a sub-chronic (7 day treatment of injection per day) administration of Captodiamine has on the levels of neurotrophic factors BDNF (Brain-derived neurotrophic factor) and GDNF (Glial cell derived neurotrophic factor) in three particular brain regions—the prefrontal cortex, the hippocampus and the hypothalamus. Neurotrophic factor concentration was determined by using an ELISA purchased from Promega Inc;

Growth Factor Modulation

FIG. 9D demonstrates that Captodiamine has no effect on Brain Derived Neurotrophic Factor (BDNF) expression levels and/or activity in either the prefrontal cortex or the hippocampus. However, Captodiamine significantly increased the levels of expression of BDNF in the hypothalamus part of the brain. In contrast, Captodiamine significantly decreased levels of expression of GDNF in the prefrontal cortex of the brain but not in either the hippocampus or the hypothalamus. The mechanism by which sigma-1 receptors modulate GDNF levels remains to be determined. However, several factors are likely involved due to the complex nature of the responses observed in our system.

Without wishing to be bound by theory, the significant increase in the levels of expression of BDNF in the hypothalamus part of the brain after administration of Captodiamine may compensate for the decrease in expression and/or functional activity of BDNF and eventual atrophy of the hippocampus (if stress exposure is persistent) which may be seen in humans suffering from anxiety and/or depression, such as chronic depression. Thus, treatment with a selective Sigma 1 or Dopamine D3 receptor agonist or a $5HT_{2c}$ receptor ligand, such as Captodiamine, may help to overcome the development of an illness, such as an anxiety and/or a depressive illness by modulation of BDNF expression and/or functional activity. Captodiamine may be used in combination with other treatments for anxiety and/or depression which include but are not limited to excitatory neurotransmitter glutamate, voluntary exercise, caloric restriction, intellectual stimulation, and various treatments for depression (such as antidepressants and electroconvulsive therapy) which strongly increase expression of BDNF in the brain, and have been shown to protect against atrophy of the hippocampus.

Anti Depressant Activity

FIG. 10A is a graph which shows the influence of Captodiamine alone and a combination of Captodiamine and Rimcazole (a Sigma-1 receptor antagonist) on behavioural activity in the Forced Swim Test. The combination Captodiamine and Rimcazole (a Sigma-1 receptor antagonist) yield approximately the same result as the control vehicle indicating that the anti-depressant action of Captodiamine as measured by the Forced Swim Test must be mediated via the Sigma 1 receptor.

Figure 1:
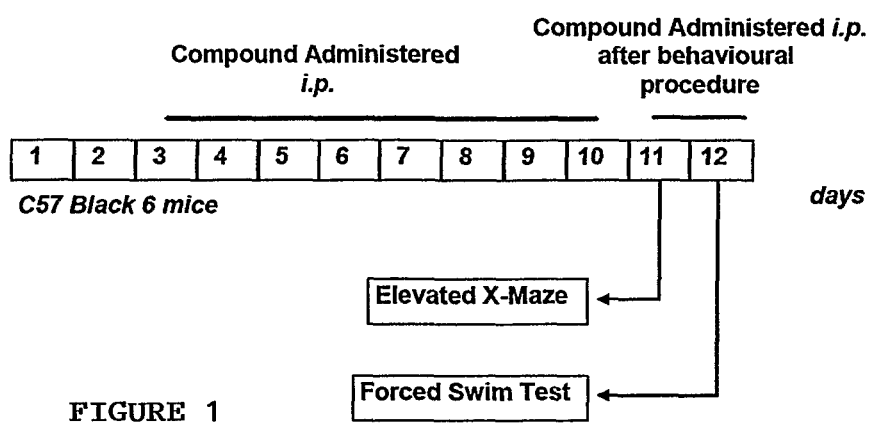
FIG. 1 provides a schematic diagram of the administration regime for the compound of Formula I under investigation.
Figure 2:
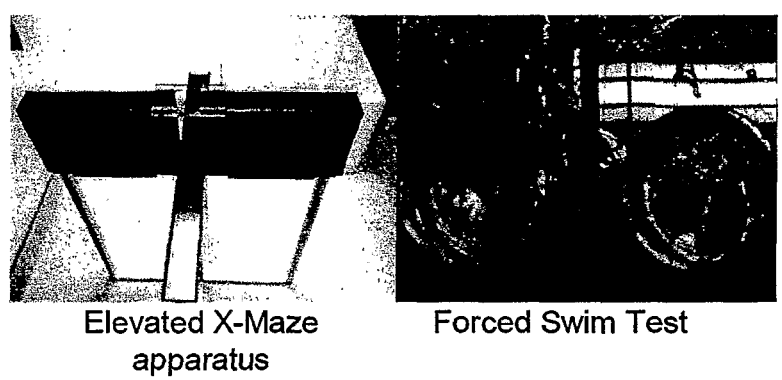
FIG. 2 provides a pictorial image of an Elevated X-Maze apparatus and the set-up for the Forced Swim Test.

The structures of the two enantiomers of Captodiamine are shown in FIG. 15 and FIG. 10B shows the results of a forced swim test in a control (vehicle), using the racemate and using the separated dextrorotary (+) and levorotary (−) enantiomers. The influence of (+/−) Captodiamine (racemate), (+) Captodiamine and (−) Captodiamine at concentrations of 3 mg/kg and 5 mg/kg on the duration of time spent immobile during the forced swim test is shown. Values are expressed as mean±S.E.M. (n=8). Statistical difference was determined using a Mann Whitney non-parametric U-test. Values significant at p<0.05 are denoted by a single asterisk and p values<0.005 are denoted by a double asterisk. The administration regime used in this experiment is shown in FIG. 1. The results shown in FIG. 10B suggest that the dextrorotary (+) enantiomer retains the antidepressant biologic activity.

Influence of Captodiamine on the Rat Pyloric Region

Figure 13:
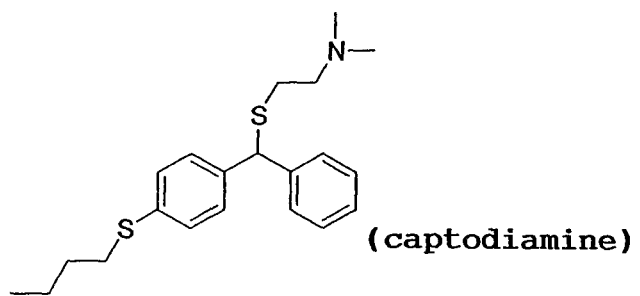
FIG. 13 provides Formulae I and II.
Figure 13:
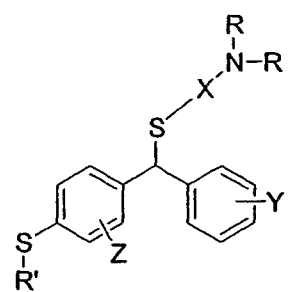
Figure 14:
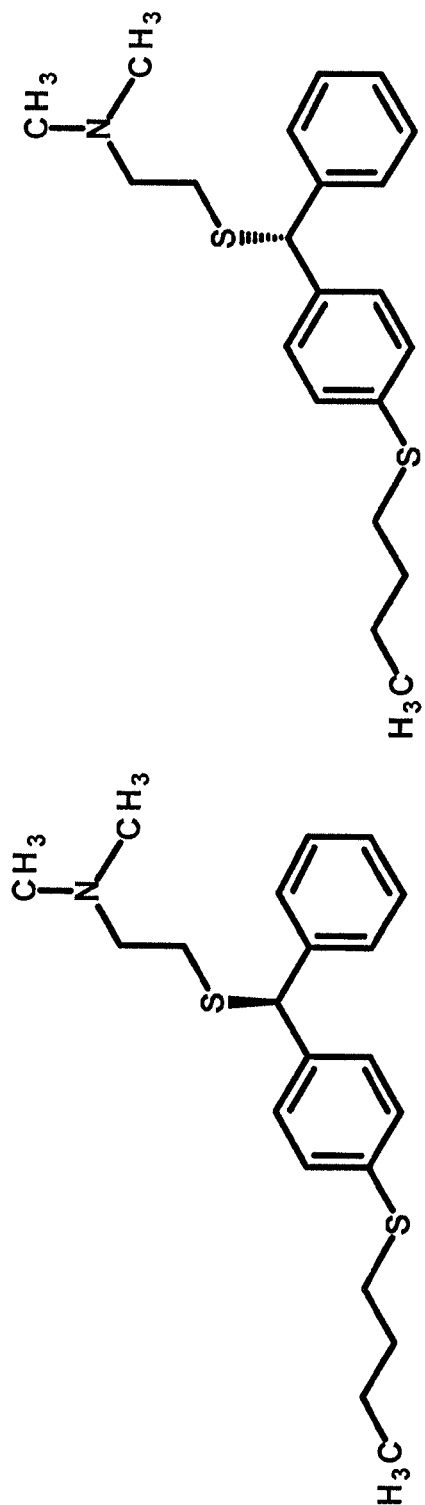
FIG. 14 shows the two enantiomers of Captodiamine.

Receptor affinity studies shown in FIG. 9B revealed a high affinity interaction between Captodiamine and the Dopamine (D) 3 receptor. As D3 agonists are known to inhibit electric field stimulated Pyloric muscle relaxation (Kashyap P., Micci M., Pasricha S., Pasricha P., The D2/D3 Agonist PD128907 (R-(+)-trans-3,4-a,10b-Tetrahydro-4-Propyl-2H,5H-[1]Benzopyrano[4,3-b]-1,4-Oxazin-9-ol) Inhibits Stimulated Pyloric Relaxation and Spontaneous Gastric Emptying, 2007, Digestive Diseases and Sciences), this action was used to characterise if Captodiamine was an agonist at the D3 receptor. FIG. 13A demonstrates the electrical field stimulation (EFS)-mediated relaxation of the rat pyloric muscle. Panel (B) demonstrates attenuation of the EFS-mediatated relaxation by addition of Captodiamine, indicating the drug to exert D3 receptor agonism.

Dopamine in Depression

There has emerged a hypothesis that depression is a result of a deficiency in mesolimbic dopamine (Dhir and Kulkarni, 2007). Like the monoamine hypothesis this has emerged mainly as a result of pharmacological evidence, drugs which increase dopamine levels in the brain by inhibiting re-uptake or agonism at dopamine receptors are potent antidepressants (Dhir and Kulkarni, 2007). Some biochemical evidence also exists. Patients with depression have been shown to have a significant decrease in the levels of dopamine and its metabolite HVA in their CSF (Dhir and Kulkarni, 2007). D3 receptors are found at high density in the limbic system, the hypothalamus and the anterior pituitary and are much less abundant than D1 or D2 receptors (Dhir and Kulkarni, 2007). These are areas of the brain which have been implicated in the pathology of depression (Mello et al., 2003).

Dopamine and Growth Factor Modulation

It was found that treatment of primary cells with D3 selective agonists resulted in a significant increase in both GDNF and BDNF synthesis/release (Du et al., 2005). It is known that administration of D3 selective agonists causes proliferation and differentiation of dopaminergic neurons and also protects against dopaminergic neuronal death following treatment with the neuro-toxin 6-OH-DA (Collo et al., 2008). This again suggests that they act by increasing neurotrophic factors thus promoting neuronal survival, proliferation and differentiation. Therefore, the effects of Captodiamine on growth factor modulation shown in FIG. 9D may be partly due to the agonistic actions of Captodiamine at the D3 receptor.

5HT2C and Depression

Receptor affinity studies shown in FIG. 9B revealed a high affinity interaction between Captodiamine and the serotonin $5HT_{2C}$ receptor. Serotonin is a monoamine neurotransmitter and has been implicated in the pathology and treatment of depression since the monoamine hypothesis of depression was proposed in 1965 (Coppen, 1967). Classic antidepressants are drugs which increase levels of monoamines in the brain such as fluoextine (Berton and Nestler, 2006). Fluoextine is a selective serotonin re-uptake inhibitor and it has been suggested that in part the mechanism of action of these drugs may be mediated by 5-HT2c receptor agonism (Martin et al., 1998). Thus serotonin and its receptors have been heavily implicated in depression. 5-HT2c receptors are expressed at high levels in the pre-frontal cortex and in limbic brain structures (Martin et al., 1998). This again implicates these receptors in the pathology of depression due to the presence of symptoms which are thought to be pre-frontal in origin such as inability to concentration.

Overall Summary

In summary, the treatment of the symptoms of anxiety and/or depression appear to be receptor specific (via a selective Sigma 1 or Dopamine D3 receptor agonist or a $5HT_{20}$ receptor ligand), factor specific (via a Growth Factor such as BDNF and/or GDNF) and region specific (via either the hypothalamus and/or the pre-frontal cortex of the brain).

The marked anxiolytic action of Captodiamine prompted a determination of its potential as an antidepressant. This antidepressant action was confirmed by the significant increase on time to immobility that was observed in the forced swim test (FIGS. 10A and 10B). The combined effect of Captodiamine on open-field behaviour and performance in the elevated X-maze suggests it to have anxiolytic actions that most likely contribute to its precognitive actions in water maze spatial paradigm and antidepressant actions in the forced swim test. In the forced swim test, we have shown in the results set out in FIG. 10B that there is an enantiomer-specific effect. In particular, our results indicate that the dextrorotary (+) enantiomer is biologically active in this test.

References

Casellas P, Galiegue S, Bourrie 8, Ferrini J B, Jbilo 0 and Vidal H (2004) SR31747A: a peripheral sigma ligand with potent antitumor activities. Anticancer Drugs 15:113-118.

Hayashi T and Su T P (2003) Sigma-I receptors (sigma(I) binding sites) form raft-like microdomains and target lipid droplets on the endoplasmic reticulum: roles in endoplasmic reticulum lipid compartmentalization and export. J Pharmacol Exp Ther 306:718-725.

Walker J M, Bowen W D, Walker F O, Matsumoto R R, De Costa B and Rice K C (1990) Sigma receptors: biology and function. Pharmacol Rev 42:355-402.

Bowen W D (2000) Sigma receptors: recent advances and new clinical potentials. Pharm Acta Hely 74:211-218.

Takahashi H, Kirsch J R, Hashimoto K, London E D, Koehler R C and Traystman R J (1996) PPBP [4-phenyl-1-(4-phenylbutyl)piperidine] decreases brain injury after transient focal ischemia in rats. Stroke 27:2120-2123.

Lockhart B P, Soulard P, Benicourt C, Privat A and Junien J L (1995) Distinct neuroprotective profiles for sigma ligands against N-methyl-D-aspartate (NMDA), and hypoxia-mediated neurotoxicity in neuronal culture toxicity studies. BrainRes 675:110-120.

Senda T, Matsuno $K_5$ Okamoto K, Kobayashi T, Nakata K and Mita S (1996) Ameliorating effect of SA4503, a novel sigma I receptor agonist, on memory impairments induced by cholinergic dysfunction in rats. Evr J Pharmacol 315: 1-10.

Hiramatsu M, Mizuno N and Kanematsu K (2006) Pharmacological characterization of the ameliorating effect on learning and memory impairment and antinociceptive effect of KT95 in mice. Behav Brain Res 167:219-225.

Matsumoto R R, Hemstreet M K, Lai N L, Thurkauf A, De Costa B R, Rice K $C_5$ Hellewell S B, Bowen W D and Walker J M (1990) Drug specificity of pharmacological dystonia. Pharmacol Biochem Behav 36:151-155.

McCracken K A, Bowen W D and Matsumoto R R (1999) Novel sigma receptor ligands attenuate the locomotor stimulatory effects of cocaine. Eur J Pharmacol 365:35 38.

Hanner M, Moebius F F, Flandorfer A, Knaus H G, Striessnig J, Kempner E and Glossmann H (1996) Purification, molecular cloning, and expression of the mammalian sigmal-binding site. Proc. Natl. Acad. Sci. U.S.A 93: 8072-8077.

*Langa F, Codony X, Tovar V, Lavado A, Giménez E, Cozar P, Cantero M, Dordal A, Hernandez E, Pérez R, Monroy X, Zamanillo D, Guitart X, Montoliu L*. Generation and phenotypic analysis of sigma receptor type I (sigma 1) knock-out mice. Eur J Neurosci. 2003 October; 18(8):2188-96.

Vilner B J and Bowen W D (2000) Modulation of cellular calcium by sigma-2 receptors: release from intracellular stores in human SK-N-SH neuroblastoma cells. J Pharmacol Exp Ther 292:900-911.

Ukai M, Maeda H, Nanya Y, Kameyama T, Matsuno K (1998) Beneficial effects of acute and repeated administrations of sigma receptor agonists on behavioral despair in mice exposed to tail suspension. Pharmacol Biochem Behav 61: 247-52

Matsuno K, Kobayashi T, Tanaka M K, Mita S (1996) sl receptor subtype is involved in the relief of behavioral despair in the mouse forced swimming test. Eur J Pharmacol 312: 267-71

Tottori K, Kikuchi T, Uwahodo Y, Yamada S, Oshiro Y, Koga N (1997) Antidepressant effect of OPC-14523 in the forced swimming test. Jpn J Pharmacol 73SI: 59P Kinsora J J, Corbin A E, Snyder B J, Wiley J N, Meltzer L T, Heffner T G (1998) Effects of igmesine in preclinical antidepressant tests. Soc Neurosci Abstr 24: 744

Hayashi T, Kagaya $A_3$ Takebayashi M, Shimizu M, Uchitomi Y, Motohashi N and Yamawaki S (1995) Modulation by sigma ligands of intracellular free Cai-+ mobilization by N-methyl D-aspartate in primary culture of rat frontal cortical neurons. J Pharmacol Exp Ther 275:207-214.

Monnet F P, Morin-Suwn M P, Leger J and Combettes L (2003) Protein kinase C-dependent potentiation of intracellular calcium influx by sigmal receptor agonists in rat hippocampal neurons. J Pharmacol Exp Ther 307:705-712.

Nishikawa H, Hashino A, Kume T, Katsuki H, Kaneko S and Akaike A (2000) Involvement of direct inhibition of NMDA receptors in the effects of sigma-receptor ligands on glutamate neurotoxicity in vitro. EurJ Pharmacol 404: 41-48.

Kume T, Nishikawa H, Taguchi R, Hashino A, Katsuki H, Kaneko S, Minami M, Satoh M and Akaike A (2002) Antagonism of NMDA receptors by sigma receptor ligands attenuates chemical ischemia-induced neuronal death in vitro. Eur J Pharmacol 455:91-100.

Sircar R, Rappaport M, Nichtenhauser R and Zukin S R (1987) The novel anticonvulsant MK801: a potent and specific ligand of the brain phencyclidine/sigma-receptor. Brain Res 435:235-240.

M M. Leyritz, Le Bezu and Azoulay, 1956 Ann. Med. Psychol., Par. 2(5) 856.

Bowman W C, Rand M J (1980) Textbook of Pharmacology, Blackwell ($2^{nd}$ Ed), pp 15.1-15.3.

Grebe R ([Ed.] 1959) Handbook of Toxicology, Volume IV, Tranquilizers. WADC Technical Report 55-16, p 12.

Dhir, A. and Kulkarni S. K. 2007. Involvement of dopamine (DA)/serotonin (5-HT)/sigma (σ1) receptor modulation in mediating the antidepressant action of ropinirole hydrochloride, a D2/D3 dopamine receptor agonist. Brain Research Bulletin 74: 58-65.

Mello, A. A. F., Mello, M. F., Carpenter L. L. and Price, L. H. 2003. Update on stress and depression: the role of the hypothalamic-pituitary-adrenal (HPA) axis. Rev Bras Psiquiatr 2003; 25(4):231-38.

Du, F., Li, R., Huang, Y., Li, X. and Le, W. 2005. Dopamine D3 receptor-preferring agonists induce neurotrophic effects on mesencephalic dopamine neurons. European Journal of Neuroscience 22: 2422-2430.

Collo, G., Zanetti, S., Missale, C. and Spano, P. F. 2008. Dopamine D3 receptor-preferring agonists increase dendrite arborization of mesencephalic dopaminergic neurons via extracellular signal-regulated kinase phosphorylation. European Journal of Neuroscience 28: 1231-1240.

Coppen, A. 1967. The biochemistry of affective disorders. Br J Psychiat. 113: 1237-1264.

Berton, O. and Nestler, E. 2006. New approaches to antidepressant therapy drug discovery: beyond the monoamines. Nat Rev Neurosci. 7: 137-151.

Martin, J. R., Bos, M., Jenck, F., Moreau, J. L., Mutel, V., Sleight, A. J., Wichmann, J., Andrews, J. S., Berendsen, H. H. G., Nroekkamp, C. L. E., Ruigt, G. S. F., Kohler, C. and van Delft, A. M. L. 1998. 5-HT2c Receptor Agonists: Pharmacological Characteristics and Therapeutic Potential. J. Pharmacol and Exp. Ther. 286: 913-923.

All references, patents, patent applications publications mentioned in the above specification, and references cited in said publications, are herein incorporated by reference (and cross-reference) in their entireties. By cross reference herein to compounds contained in patents and patent applications which can be used in accordance with invention, we mean the pharmaceutically active compounds as defined in the claims (in particular of claim 1) and the specific examples (all of which is incorporated herein by reference). Various modifications and variations of the described methods and uses of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method of treating depression associated with an affective disorder comprising administering a composition comprising an effective amount of a $5HT_2$ receptor ligand 2-[(4-butylsulfanylphenye)-phenylmethyl]sulfanyl-N,N-dimethylethanamine (Captodiamine) or a pharmaceutically acceptable salt thereof to a subject in need thereof.

2. The method of claim 1, wherein said composition further comprises agomelatine (Valdoxan).

3. A method of treating symptoms of depression associated with an affective disorder; and/or symptoms associated with a cognitive impairment disorder in a subject in need of same comprising administering a composition comprising an effective amount of a $5HT_{2c}$ receptor ligand 2-[(4-butylsulfanylphenyl)-phenylmethyl]sulfanyl-N,N-dimethylethanamine (Captodiamine) or a pharmaceutically acceptable salt thereof to a subject in need thereof.

4. The method of claim 3, wherein said composition further comprises agomelatine (Valdoxan).

\* \* \* \* \*